United States Patent
Dhar et al.

(10) Patent No.: US 8,309,730 B2
(45) Date of Patent: Nov. 13, 2012

(54) NONSTEROIDAL COMPOUNDS USEFUL AS MODULATORS OF GLUCOCORTICOID RECEPTOR AP-1 AND/OR NF-KAPPAB ACITIVITY AND USE THEREOF

(75) Inventors: T. G. Murali Dhar, Princeton, NJ (US); Hai-Yun Xiao, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 40 days.

(21) Appl. No.: 12/741,597

(22) PCT Filed: Oct. 30, 2008

(86) PCT No.: PCT/US2008/081702
§ 371 (c)(1),
(2), (4) Date: Feb. 14, 2011

(87) PCT Pub. No.: WO2009/058944
PCT Pub. Date: May 7, 2009

(65) Prior Publication Data
US 2011/0263494 A1    Oct. 27, 2011

Related U.S. Application Data

(60) Provisional application No. 60/984,515, filed on Nov. 1, 2007.

(51) Int. Cl.
*A61K 31/438* (2006.01)
*A61K 31/4375* (2006.01)
*C07D 471/10* (2006.01)
*C07D 487/04* (2006.01)
*C07D 491/22* (2006.01)
*C07D 471/04* (2006.01)

(52) U.S. Cl. ............ 546/85; 546/86; 546/18; 514/278; 514/291

(58) Field of Classification Search ............ 546/85, 546/86
See application file for complete search history.

(56) References Cited

FOREIGN PATENT DOCUMENTS
WO    WO 03/086294    10/2003
WO    WO 2004/046145    6/2004

OTHER PUBLICATIONS

Colagiuri et al., American Journal of Public Health, Sep. 2006, vol. 96, No. 9, pp. 1562-1569.*
Bruno et al., Expert Opinion Emerging Drugs, (2005), 10(4), pp. 747-771.*
Park, Diabetes Research and Clinical Practice 66S (2004), S33-S35.*
Curtis et al., The Journal of the American Board of Family Practice, vol. 18, pp. 37-43, (2005).*

* cited by examiner

*Primary Examiner* — Laura L. Stockton
(74) *Attorney, Agent, or Firm* — Burton Rodney

(57) ABSTRACT

Disclosed are compounds of Formula (I) wherein: one of A and D is —N— and the other of A and D is —C—; or enantiomers, diastereomers, or pharmaceutically-acceptable salts thereof. Also disclosed are methods of using such compounds to modulate the function of glucocorticoid receptor activity and pharmaceutical compositions comprising such compounds.

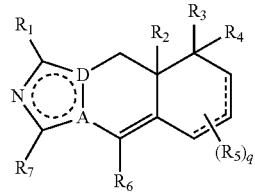

7 Claims, No Drawings

NONSTEROIDAL COMPOUNDS USEFUL AS MODULATORS OF GLUCOCORTICOID RECEPTOR AP-1 AND/OR NF-KAPPAB ACITIVITY AND USE THEREOF

FIELD OF THE INVENTION

The present invention relates to new non-steroidal compounds that are modulators of the glucocorticoid receptor AP-1 and/or NF-κB activity, to methods of using such compounds in the treatment of diseases such as inflammatory or immune associated diseases, and obesity and diabetes, and to pharmaceutical compositions comprising the compounds.

BACKGROUND OF THE INVENTION

The transcription factors NF-κB and AP-1 are involved in regulating the expression of a number of genes involved in mediating inflammatory and immune responses. NF-κB regulates the transcription of genes including TNF-α, IL-1, IL-2, IL-6, adhesion molecules (such as E-selectin) and chemokines (such as Rantes), among others. AP-1 regulates the production of the cytokines TNF-α, IL-1, IL-2, as well as, matrix metalloproteases. Drug therapies targeting TNF-α, a gene whose expression is regulated by both NF-κB and AP-1, have been shown to be highly efficacious in several inflammatory human diseases including rheumatoid arthritis and Crohn's disease. Accordingly, NF-κB and AP-1 play key roles in the initiation and perpetuation of inflammatory and immunological disorders. See Baldwin, A. S., *Journal of Clin. Investigation*, 107:3 (2001); Firestein, G. S., and Manning, A. M., *Arthritis and Rheumatism*, 42:609 (1999); and Peltz, G., *Curr. Opin. in Biotech.*, 8:467 (1997).

There are many signaling molecules (kinases and phosphatases) upstream of AP-1 and NF-κB that are potential therapeutic drug targets. The kinase JNK plays an essential role in regulating the phosphorylation and subsequent activation of c-jun, one of the subunits which constitute the AP-1 complex (fos/c-jun). Compounds that inhibit JNK have been shown to be efficacious in animal models of inflammatory disease. See Manning, A. M. and Davis, R. J., *Nature Rev. Drug Disc.*, 2:554 (2003). A kinase critical to the activation of NF-κB is the IκB kinase (IKK). This kinase plays a key role in the phosphorylation of IκB. Once IκB is phosphorylated it undergoes degradation leading to the release of NF-κB which can translocate into the nucleus and activate the transcription of the genes described above. An inhibitor of IKK has been shown to be efficacious in animal models of inflammatory disease. See Burke, J. R., *Curr. Opin. Drug Discov. Devel.*, 6(5):720-728, (September 2003).

In addition to inhibiting signaling cascades involved in the activation of NF-κB and AP-1, the glucocorticoid receptor has been shown to inhibit the activity of NF-κB and AP-1 via direct physical interactions. The glucocorticoid receptor (GR) is a member of the nuclear hormone receptor family of transcription factors, and a member of the steroid hormone family of transcription factors. Affinity labeling of the glucocorticoid receptor protein allowed the production of antibodies against the receptor which facilitated cloning the glucocorticoid receptors. For results in humans see Weinberger et al., *Science*, 228:740-742 (1985); Weinberger et al., *Nature*, 318:670-672 (1986) and for results in rats see Miesfeld, R., *Nature*, 312:779-781 (1985).

Glucocorticoids that interact with GR have been used for over 50 years to treat inflammatory diseases. It has been shown that glucocorticoids exert their anti-inflammatory activity via the inhibition by GR of the transcription factors NF-κB and AP-1. This inhibition is termed transrepression. It has been shown that the primary mechanism for inhibition of these transcription factors by GR is via a direct physical interaction. This interaction alters the transcription factor complex and inhibits the ability of NF-κB and AP-1 to stimulate transcription. See Jonat, C. et al., *Cell*, 62:1189 (1990); Yang-Yen, H. F. et al., *Cell*, 62:1205 (1990); Diamond, M. I. et al., *Science* 249:1266 (1990); and Caldenhoven, E. et al., *Mol. Endocrinol.*, 9:401 (1995). Other mechanisms such as sequestration of co-activators by GR have also been proposed. See Kamei, Y. et al., *Cell*, 85:403 (1996); and Chakravarti, D. et al., *Nature*, 383:99 (1996).

In addition to causing transrepression, the interaction of a glucocorticoid with GR can cause GR to induce transcription of certain genes. This induction of transcription is termed transactivation. Transactivation requires dimerization of GR and binding to a glucocorticoid response element (GRE).

Recent studies using a transgenic GR dimerization defective mouse which cannot bind DNA have shown that the transactivation (DNA binding) activities of GR could be separated from the transrepressive (non-DNA binding) effect of GR. These studies also indicate that many of the side effects of glucocorticoid therapy are due to the ability of GR to induce transcription of various genes involved in metabolism, whereas transrepression, which does not require DNA binding, leads to suppression of inflammation. See Reichardt, H. M. et al., *Cell*, 93:531 (1998) and Reichardt, H. M., *EMBO J.*, 20:7168 (2001).

Compounds that modulate AP-1 and NF-κB activity would be useful in the treatment of inflammatory and immune diseases and disorders such as osteoarthritis, rheumatoid arthritis, multiple sclerosis, asthma, inflammatory bowel disease, transplant rejection and graft vs. host disease.

Also, with respect to the glucocorticoid receptor pathway, it is known that glucocorticoids are potent anti-inflammatory agents. However their systemic use is limited by side effects. Compounds that retain the anti-inflammatory efficacy of glucocorticoids while minimizing the side effects such as diabetes, osteoporosis and glaucoma would be of great benefit to a very large number of patients with inflammatory diseases.

Additionally concerning GR, the art is in need of compounds that antagonize transactivation. Such compounds may be useful in treating metabolic diseases associated with increased levels of glucocorticoid, such as diabetes, osteoporosis and glaucoma.

Additionally concerning GR, the art is in need of compounds that cause transactivation. Such compounds may be useful in treating metabolic diseases associated with a deficiency in glucocorticoid. Such diseases include Addison's disease.

SUMMARY OF THE INVENTION

The present invention relates to new non-steroidal compounds which are effective modulators of the glucocorticoid receptor, and/or AP-1, and/or NF-κB activity and thus are useful in treating diseases such as inflammatory or immune associated diseases, and/or obesity and diabetes, and to a method for using such compounds to treat these and related diseases.

Described herein are compounds of Formula (I):

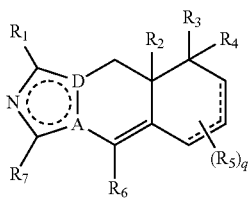

or enantiomers, diastereomers, or pharmaceutically-acceptable salts thereof, wherein:
--- is a single bond or double bond;
one of A and D is —N— and the other of A and D is —C—;
$R_1$ is hydrogen, $C_{1-3}$alkyl, $C_{2-3}$alkenyl, $C_{2-3}$alkynyl, cyclopropyl, halogen, —$CH_2F$, $CHF_2$, —$CF_3$, —CN, $C_{1-3}$alkoxy, —$NR_dR_e$, —C(O)$OR_d$, or —C(O)$NR_dR_e$;
$R_2$ is hydrogen or $C_{1-3}$alkyl;
$R_3$ is hydrogen, OH, F, Cl, or $C_{1-3}$alkyl;
$R_4$ is
  i) hydrogen,
  ii) $C_{1-3}$alkyl is optionally substituted with OH, F, or phenyl,
  iii) $C_{2-4}$alkenyl or $C_{2-4}$alkynyl,
  iv) aryl or aryl substituted with one or more of halogen, $C_{1-3}$alkyl, methoxy, and/or —CN,
  v) —$CR_aR_bR_c$, —C(O)$R_c$, —$(CH_2)_pC(O)NHR_c$, —$(CH_2)_pNHR_c$, —$(CH_2)_pNHC(O)OR_c$, or —$(CH_2)_pNHC(O)NHR_c$, wherein p is zero, 1, 2, or 3, or
  vi) —$CR_aR_bR_c$ wherein $R_b$ and $R_c$ together with the carbon atom to which they are attached form a 1- or 2-ring heterocycle having at least one heteroatom selected from N, O, and S;
or $R_3$ and $R_4$ together with the carbon atom to which they are attached, form a 5- to 7-membered saturated heterocyclic ring having 1 to 2 heteroatoms independently selected from N, O, and S;
each $R_5$ is independently $C_{1-4}$alkyl, $C_{1-4}$haloalkyl, $C_{3-6}$cycloalkyl, $C_{2-4}$alkenyl, $C_{2-4}$alkynyl, F, Cl, —CN, $C_{1-3}$alkoxy, and/or —$OCF_3$;
$R_6$ is hydrogen, $C_{1-4}$alkyl, $C_{1-4}$haloalkyl, $C_{3-6}$cycloalkyl, $C_{2-4}$alkenyl, $C_{2-4}$alkynyl, F, Cl, —CN, $C_{1-3}$alkoxy, or —$OCF_3$;
$R_7$ is aryl or heterocyclo optionally substituted with one or more of $C_{1-3}$alkyl, $C_{1-3}$haloalkyl, $C_{1-3}$alkoxy, CN, and/or halogen;
$R_a$ is hydrogen, $C_{1-3}$alkyl, or $C_{1-3}$alkyl substituted with OH or F;
$R_b$ is hydrogen, OH, $C_{1-3}$alkyl, $C_{1-3}$alkoxy, or $C_{1-3}$alkyl substituted with OH or F;
$R_c$ is:
  i) $C_{1-5}$alkyl optionally substituted with OH, aryl, or haloaryl,
  ii) $C_{1-3}$haloalkyl, $C_{3-6}$cycloalkyl, or $C_{2-4}$alkenyl,
  iii) $C_{2-4}$alkynyl optionally substituted with aryl,
  iv) aryl optionally substituted with one or more of halogen, methoxy, —S(O)($C_{1-3}$alkyl), —S(O)$_2$($C_{1-3}$alkyl), —CN, $C_{1-3}$alkyl, $C_{1-3}$hydroxyalkyl, $C_{1-3}$haloalkyl, saturated heterocyclo, and/or —S—($C_{1-3}$alkyl), or
  v) 1- or 2-ring aryl or heteroaryl optionally substituted with one or more of $C_{1-4}$alkyl, halogen, —C(O)OH, —C(O)O($C_{1-3}$alkyl), —C(O)NH($C_{1-3}$alkyl), or —C(O)N($C_{1-3}$alkyl)$_2$;
$R_d$ is hydrogen or $C_{1-3}$alkyl;
$R_e$ is hydrogen or $C_{1-3}$alkyl; and
q is zero, 1, 2, or 3.

Further described herein is at least one pharmaceutical composition comprising at least one compound of Formula (I) or an enantiomer, a diastereomer, or a pharmaceutically-acceptable salt thereof; and at least one pharmaceutically acceptable carrier and/or diluent.

Even further described herein is a method of modulating the function of AP-1 and/or NF-κB activity, comprising administering to a patient in need thereof, an effective amount of at least one compound of Formula (I) or an enantiomer, a diastereomer, or a pharmaceutically-acceptable salt thereof.

Yet even further described herein is at least one method treating a condition or disorder comprising administering to a mammalian species in need thereof, a therapeutically effective amount of at least one compound of Formula (I) or an enantiomer, a diastereomer, or a pharmaceutically-acceptable salt thereof.

DETAILED DESCRIPTION OF THE INVENTION

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof.

Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

All stereoisomers and geometric isomer(s) of the compounds of Formula (I), such as, for example, stereoisomer(s) that exist due to asymmetric carbons on various substituents, either in admixture or in pure or substantially pure form are further contemplated herein. In one embodiment, all enantiomers, tautomers, and diastereomers of the compounds of Formula (I), as well as mixtures, compounds, racemic compounds, racemic mixtures, and racemates produced therefrom are contemplated herein. In another embodiment, all optically active isomers of the compounds of Formula (I), including pure or substantially pure optically active isomers, i.e., optically active isomers substantially free of other isomers are contemplated herein.

When a compound containing a single enantiomer of a compound of Formula (I) is desired, such compound can be obtained by either resolution of the final product or by stereospecific synthesis from either isomerically pure starting material(s), or any convenient intermediate(s). Resolution of the final product, an intermediate, or a starting material can be effected by any suitable method known in the art, including, for example, physical methods, such as, for example, fractional crystallization, separation or crystallization of diastereomeric derivatives, and separation by chiral column chromatography. Individual optical isomers can be obtained from racemates through, for example, conventional methods, such as, for example, salt formation with an optically active acid followed by crystallization. The chiral centers of the compounds in accordance with Formula (I) can have the S or R configuration as defined by the IUPAC 1974 Recommendations.

In one embodiment, the compounds of Formula (I) are provided wherein D is nitrogen (—N—) and A is carbon (—C—). The compounds of this embodiment have structures represented by Formula (II):

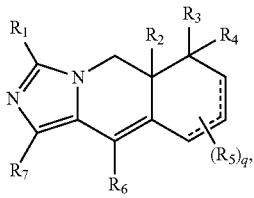

(II)

or enantiomers, diastereomers, or pharmaceutically-acceptable salts thereof, wherein $R_1$, $R_2$, $R_3$, $R_4$, $R_5$, $R_6$, $R_7$, and q are defined hereinabove. The compounds of this embodiment include compounds represented by the structures of Formulas (IIa), (IIb), and (IIc):

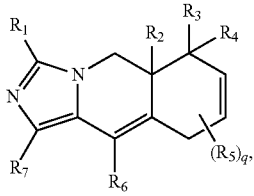

(IIa)

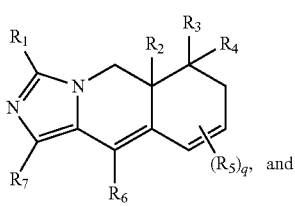

(IIb)

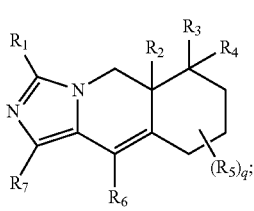

(IIc)

or enantiomers, diastereomers, or pharmaceutically-acceptable salts thereof.

In one embodiment, the compounds of Formula (I) are provided wherein A is nitrogen (—N—) and D is carbon (—C—). The compounds of this embodiment have structures represented by Formula (III)

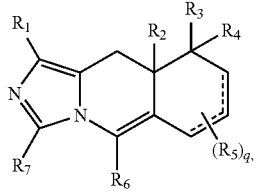

(III)

or enantiomers, diastereomers, or pharmaceutically-acceptable salts thereof, wherein $R_1$, $R_2$, $R_3$, $R_4$, $R_5$, $R_6$, $R_7$, and q are defined hereinabove. The compounds of this embodiment include compounds represented by the structures of Formulas (IIIa), (IIIb), and (IIIc):

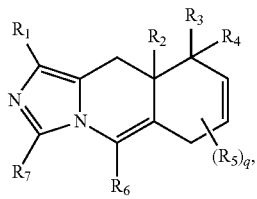

(IIIa)

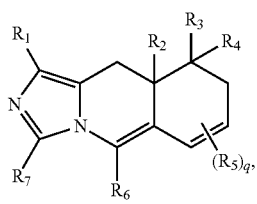

(IIIb)

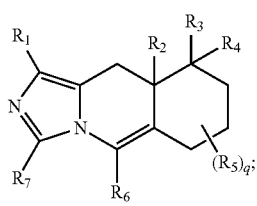

(IIIc)

or enantiomers, diastereomers, or pharmaceutically-acceptable salts thereof.

In one embodiment, the compounds of Formula (I), or enantiomers, diastereomers, or pharmaceutically-acceptable salts thereof, are provided wherein:

--- is a single bond or double bond;

one of A and D is —N— and the other of A and D is —C—;

$R_1$ is hydrogen, $C_{1-3}$alkyl, $C_{2-3}$alkenyl, $C_{2-3}$alkynyl, cyclopropyl, halogen, —$CH_2F$, $CHF_2$, —$CF_3$, —CN, $C_{1-3}$alkoxy, —$NR_dR_e$, —$C(O)OR_d$, or —$C(O)NR_dR_e$;

$R_2$ is hydrogen or $C_{1-3}$alkyl;

$R_3$ is hydrogen or OH;

$R_4$ is i) hydrogen, ii) $C_{1-3}$alkyl optionally substituted with OH or phenyl, iii) $C_{2-4}$alkenyl, iv) phenyl optionally substituted with Cl, v) —$CR_aR_bR_c$, —$C(O)R_c$, —$(CH_2)_pC(O)NHR_c$, —$(CH_2)_pNHR_c$, —$(CH_2)_pNHC(O)OR_c$, or —$(CH_2)_pNHC(O)NHR_c$, wherein p is zero, 1, 2, or 3, or vi)

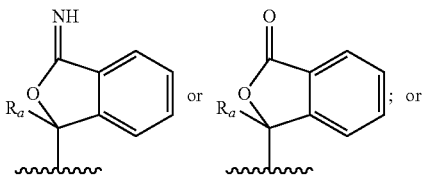

R$_3$ and R$_4$ together with the carbon atom to which they are attached, form a 5- to 7-membered saturated heterocyclic ring having 1 to 2 heteroatoms independently selected from N, O, and S;

each R$_5$ is independently C$_{1-4}$alkyl, C$_{1-4}$haloalkyl, C$_{3-6}$cycloalkyl, C$_{2-4}$alkenyl, C$_{2-4}$alkynyl, F, Cl, —CN, C$_{1-3}$alkoxy, and —OCF$_3$;

R$_6$ is hydrogen, C$_{1-4}$alkyl, C$_{1-4}$haloalkyl, C$_{3-6}$cycloalkyl, C$_{2-4}$alkenyl, C$_{2-4}$alkynyl, F, Cl, —CN, C$_{1-3}$alkoxy, and —OCF$_3$;

R$_7$ is unsubstituted aryl or aryl substituted with halogen;
R$_a$ is hydrogen, methyl, ethyl, or —CF$_3$;
R$_b$ is hydrogen, OH, or methoxy;
R$_c$ is:
  i) C$_{1-5}$alkyl optionally substituted with phenyl or fluorophenyl,
  ii) C$_{1-3}$fluoroalkyl, C$_{3-6}$cycloalkyl, or C$_{2-4}$alkenyl,
  iii) C$_{2-4}$alkynyl optionally substituted with phenyl,
  iv) phenyl optionally substituted with one or more of F, Cl, methoxy, —S(O)CH$_3$, —S(O)$_2$CH$_3$, —CN, C$_{1-3}$alkyl, —SCH$_3$, and/or C$_{1-3}$alkyl substituted with OH or pyrrolidinyl,
  v) tetrahydropyranyl, pyridinyl, pyrimidinyl, thiazolyl, thiadiazolyl, or thianaphthenyl,
  vi) thiophenyl optionally substituted with C$_{1-4}$alkyl, Cl, —C(O)OH, —C(O)OCH$_3$, —C(O)NHCH$_3$, or —C(O)N(CH$_3$)$_2$;
R$_d$ is hydrogen or C$_{1-3}$alkyl;
R$_e$ is hydrogen or C$_{1-3}$alkyl; and
q is zero, 1, 2, or 3. For example, this embodiment provides compounds of Formula (I) wherein R$_1$ is hydrogen, R$_2$ is methyl, R$_6$ is hydrogen, and q is zero, which have structures represented by Formula (Ia):

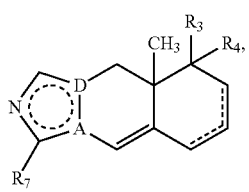

(Ia)

or enantiomers, diastereomers, or pharmaceutically-acceptable salts thereof.

In another embodiment, the compounds of Formula (II), or enantiomers, diastereomers, or pharmaceutically-acceptable salts thereof, are provided wherein:

R$_1$ is hydrogen, C$_{1-3}$alkyl, C$_{2-3}$alkenyl, C$_{2-3}$alkynyl, cyclopropyl, halogen, —CH$_2$F, CHF$_2$, —CF$_3$, —CN, C$_{1-3}$alkoxy, —NR$_d$R$_e$, —C(O)OR$_d$, or —C(O)NR$_d$R$_e$;
R$_2$ is hydrogen or C$_{1-3}$alkyl;
R$_3$ is hydrogen or OH;

R$_4$ is
  i) hydrogen,
  ii) C$_{1-3}$alkyl optionally substituted with OH or phenyl,
  iii) C$_{2-4}$alkenyl,
  iv) phenyl optionally substituted with Cl,
  v) —CR$_a$R$_b$R$_c$, —C(O)R$_c$, —(CH$_2$)$_p$C(O)NHR$_c$, —(CH$_2$)$_p$NHR$_c$, —(CH$_2$)$_p$NHC(O)OR$_c$, or —(CH$_2$)$_p$NHC(O)NHR$_c$, wherein p is zero, 1, 2, or 3, or
  vi)

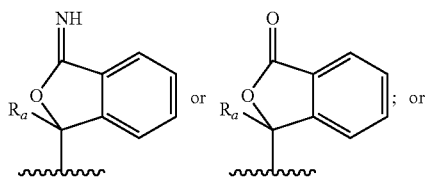

R$_3$ and R$_4$ together with the carbon atom to which they are attached, form a 5- to 7-membered saturated heterocyclic ring having 1 to 2 heteroatoms independently selected from N, O, and S;

each R$_5$ is independently C$_{1-4}$alkyl, C$_{1-4}$haloalkyl, C$_{3-6}$cycloalkyl, C$_{2-4}$alkenyl, C$_{2-4}$alkynyl, F, Cl, —CN, C$_{1-3}$alkoxy, and —OCF$_3$;

R$_6$ is hydrogen, C$_{1-4}$alkyl, C$_{1-4}$haloalkyl, C$_{3-6}$cycloalkyl, C$_{2-4}$alkenyl, C$_{2-4}$alkynyl, F, Cl, —CN, C$_{1-3}$alkoxy, and —OCF$_3$;

R$_7$ is unsubstituted aryl or aryl substituted with halogen;
R$_a$ is hydrogen, methyl, ethyl, or —CF$_3$;
R$_b$ is hydrogen, OH, or methoxy;
R$_c$ is:
  i) C$_{1-5}$alkyl optionally substituted with phenyl or fluorophenyl,
  ii) C$_{1-3}$fluoroalkyl, C$_{3-6}$cycloalkyl, or C$_{2-4}$alkenyl,
  iii) C$_{2-4}$alkynyl optionally substituted with phenyl,
  iv) phenyl optionally substituted with one or more of F, Cl, methoxy, —S(O)CH$_3$, —S(O)$_2$CH$_3$, —CN, C$_{1-3}$alkyl, —SCH$_3$, and/or C$_{1-3}$alkyl substituted with OH or pyrrolidinyl,
  v) tetrahydropyranyl, pyridinyl, pyrimidinyl, thiazolyl, thiadiazolyl, or thianaphthenyl;
  vi) thiophenyl optionally substituted with C$_{1-4}$alkyl, Cl, —C(O)OH, —C(O)OCH$_3$, —C(O)NHCH$_3$, or —C(O)N(CH$_3$)$_2$;
R$_d$ is hydrogen or C$_{1-3}$alkyl;
R$_e$ is hydrogen or C$_{1-3}$alkyl; and
q is zero, 1, 2, or 3; preferably q is zero or 1. For example, this embodiment provides compounds of Formula (II) wherein R$_1$ is hydrogen, R$_2$ is methyl, R$_6$ is hydrogen, and q is zero, which have structures represented by Formula (IId):

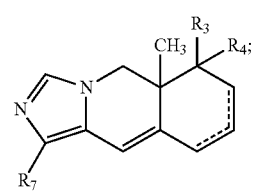

(IId)

or enantiomers, diastereomers, or pharmaceutically-acceptable salts thereof. The compounds of Formula (IId) include compounds represented by the structures of Formulas (IIe), (IIf), and (IIg):

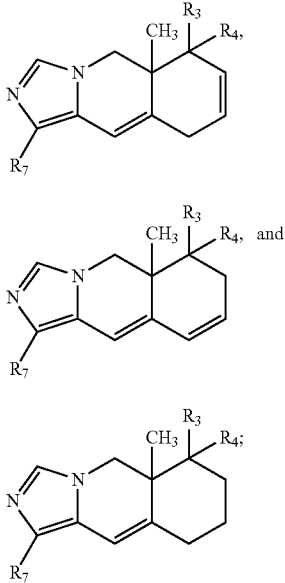

or enantiomers, diastereomers, or pharmaceutically-acceptable salts thereof, wherein $R_3$, $R_4$, and $R_7$ are defined in this embodiment hereinabove.

In another embodiment, the compounds of Formula (III), or enantiomers, diastereomers, or pharmaceutically-acceptable salts thereof, are provided wherein:

$R_1$ is hydrogen, $C_{1-3}$alkyl, $C_{2-3}$alkenyl, $C_{2-3}$alkynyl, cyclopropyl, halogen, —$CH_2F$, $CHF_2$, —$CF_3$, —CN, $C_{1-3}$alkoxy, —$NR_dR_e$, —$C(O)OR_d$, or —$C(O)NR_dR_e$;

$R_2$ is hydrogen or $C_{1-3}$alkyl;

$R_3$ is hydrogen or OH;

$R_4$ is
  i) hydrogen,
  ii) $C_{1-3}$alkyl optionally substituted with OH or phenyl,
  iii) $C_{2-4}$alkenyl,
  iv) phenyl optionally substituted with Cl,
  v) —$CR_aR_bR_c$, —$C(O)R_c$, —$(CH_2)_pC(O)NHR_c$, —$(CH_2)_pNHR_c$, —$(CH_2)_pNHC(O)OR_c$, or —$(CH_2)_p$NHC(O)NHR_c$, wherein p is zero, 1, 2, or 3, or
  vi)

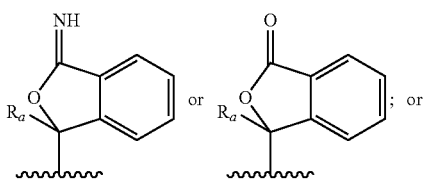

$R_3$ and $R_4$ together with the carbon atom to which they are attached, form a 5- to 7-membered saturated heterocyclic ring having 1 to 2 heteroatoms independently selected from N, O, and S;

each $R_5$ is independently $C_{1-4}$alkyl, $C_{1-4}$haloalkyl, $C_{3-6}$cycloalkyl, $C_{2-4}$alkenyl, $C_{2-4}$alkynyl, F, Cl, —CN, $C_{1-3}$alkoxy, and —$OCF_3$;

$R_6$ is hydrogen, $C_{1-4}$alkyl, $C_{1-4}$haloalkyl, $C_{3-6}$cycloalkyl, $C_{2-4}$alkenyl, $C_{2-4}$alkynyl, F, Cl, —CN, $C_{1-3}$alkoxy, and —$OCF_3$;

$R_7$ is unsubstituted aryl or aryl substituted with halogen;

$R_a$ is hydrogen, methyl, ethyl, or —$CF_3$;

$R_b$ is hydrogen, OH, or methoxy;

$R_c$ is:
  i) $C_{1-5}$alkyl optionally substituted with phenyl or fluorophenyl,
  ii) $C_{1-3}$fluoroalkyl, $C_{3-6}$cycloalkyl, or $C_{2-4}$alkenyl,
  iii) $C_{2-4}$alkynyl optionally substituted with phenyl,
  iv) phenyl optionally substituted with one or more of F, Cl, methoxy, —$S(O)CH_3$, —$S(O)_2CH_3$, —CN, $C_{1-3}$alkyl, —$SCH_3$, and/or $C_{1-3}$alkyl substituted with OH or pyrrolidinyl,
  v) tetrahydropyranyl, pyridinyl, pyrimidinyl, thiazolyl, thiadiazolyl, or thianaphthenyl,
  vi) thiophenyl optionally substituted with $C_{1-4}$alkyl, Cl, —$C(O)OH$, —$C(O)OCH_3$, —$C(O)NHCH_3$, or —$C(O)N(CH_3)_2$;

$R_d$ is hydrogen or $C_{1-3}$alkyl;

$R_e$ is hydrogen or $C_{1-3}$alkyl; and q is zero, 1, 2, or 3; preferably q is zero or 1. For example, this embodiment provides compounds of Formula (III) wherein $R_1$ is hydrogen, $R_2$ is methyl, $R_6$ is hydrogen, and q is zero, which have structures represented by Formula (IIId):

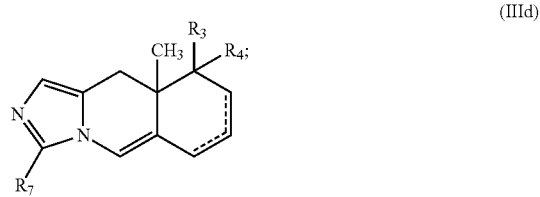

or enantiomers, diastereomers, or pharmaceutically-acceptable salts thereof. The compounds of Formula (IIId) include compounds represented by the structures of Formulas (IIIe), (IIIf), and (IIIg):

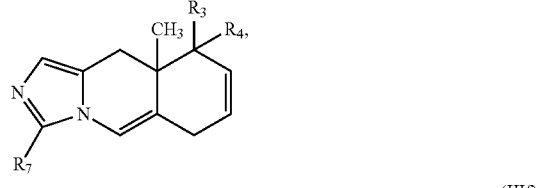

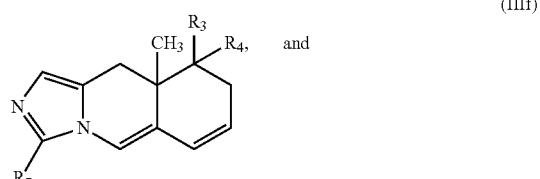

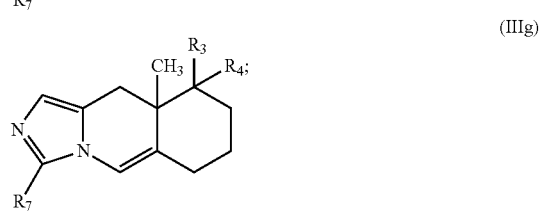

or enantiomers, diastereomers, or pharmaceutically-acceptable salts thereof, wherein $R_3$, $R_4$, and $R_7$ are defined in this embodiment hereinabove.

In one embodiment, compounds of Formulas (IIg), or enantiomers, diastereomers, or pharmaceutically-acceptable salts thereof, are provided wherein:

$R_3$ is hydrogen or OH;

$R_4$ is
i) hydrogen,
ii) $C_{1-3}$alkyl optionally substituted with OH or phenyl,
iii) $C_{2-4}$alkenyl,
iv) phenyl optionally substituted with Cl,
v) —$CR_aR_bR_c$, —$C(O)R_c$, —$(CH_2)_pC(O)NHR_c$, —$(CH_2)_pNHR_c$, —$(CH_2)_pNHC(O)OR_c$, or —$(CH_2)_p NHC(O)NHR_c$, wherein p is zero, 1, 2, or 3, or
vi)

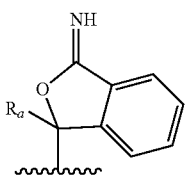

or ; or $R_3$ and $R_4$ together with the carbon atom to which they are attached, form a 5- to 7-membered saturated heterocyclic ring having 1 to 2 heteroatoms independently selected from N, O, and S;

$R_7$ is unsubstituted aryl or aryl substituted with halogen;

$R_a$ is hydrogen, methyl, ethyl, or —$CF_3$;

$R_b$ is hydrogen, OH, or methoxy;

$R_c$ is:
i) $C_{1-5}$alkyl optionally substituted with phenyl or fluorophenyl,
ii) $C_{1-3}$fluoroalkyl, $C_{3-6}$cycloalkyl, or $C_{2-4}$alkenyl,
iii) $C_{2-4}$alkynyl optionally substituted with phenyl,
iv) phenyl optionally substituted with one or more of F, Cl, methoxy, —$S(O)CH_3$, —$S(O)_2CH_3$, —CN, $C_{1-3}$alkyl, —$SCH_3$, and/or $C_{1-3}$alkyl substituted with OH or pyrrolidinyl,
v) tetrahydropyranyl, pyridinyl, pyrimidinyl, thiazolyl, thiadiazolyl, or thianaphthenyl;
vi) thiophenyl optionally substituted with $C_{1-4}$alkyl, Cl, —$C(O)OH$, —$C(O)OCH_3$, —$C(O)NHCH_3$, or —$C(O)N(CH_3)_2$.

In one embodiment, compounds of Formulas (IIg), or enantiomers, diastereomers, or pharmaceutically-acceptable salts thereof, are provided wherein: $R_3$ is hydrogen or OH;

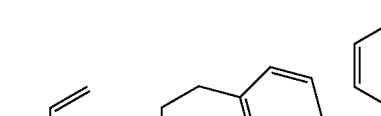

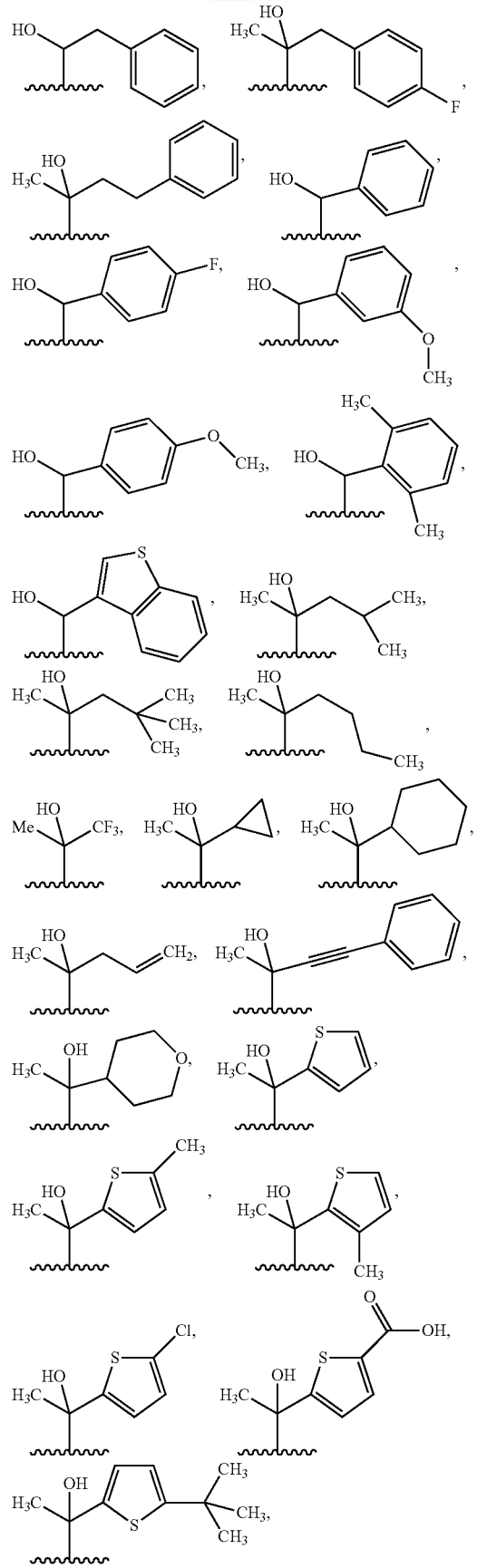

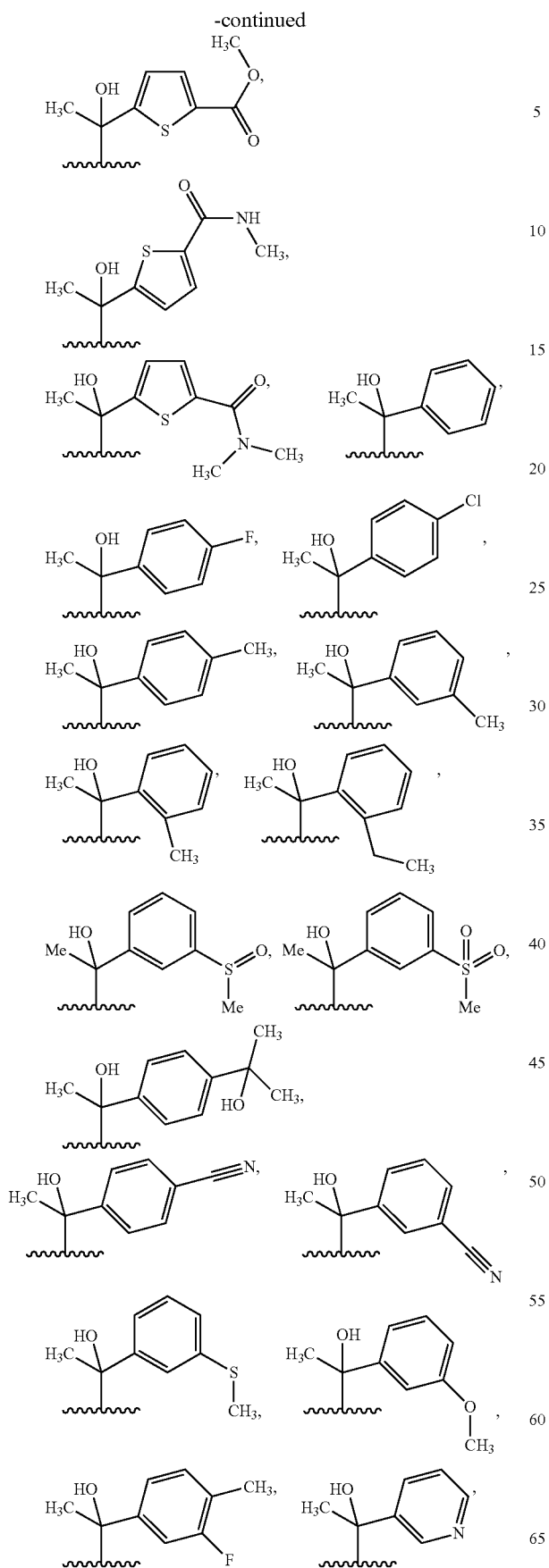
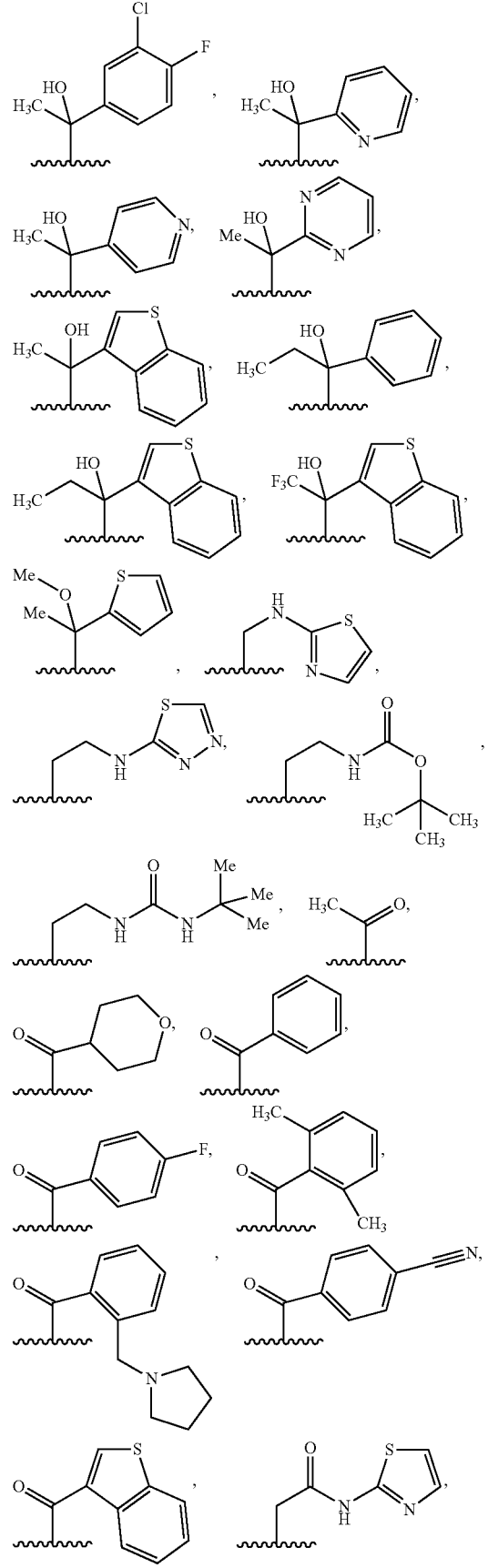

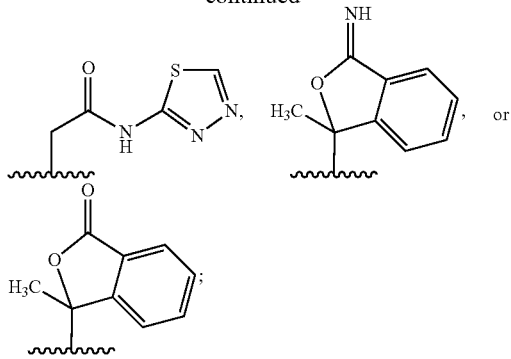

or $R_3$ and $R_4$ together are:

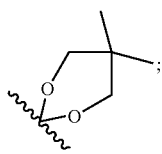

and
$R_7$ is unsubstituted aryl or aryl substituted with halogen.
Preferably $R_7$ is phenyl or fluorophenyl.

In one embodiment, compounds of Formula (I) or enantiomers, diastereomers, or pharmaceutically-acceptable salts thereof, are provided wherein $R_1$ is hydrogen, methyl, halogen, —$CH_2F$, —$CHF_2$, —$CF_3$, or CN. Preferably, $R_1$ is hydrogen or methyl; and more preferably, hydrogen.

In one embodiment, compounds of Formula (I) or enantiomers, diastereomers, or pharmaceutically-acceptable salts thereof, are provided wherein $R_2$ is hydrogen, methyl, or ethyl. Preferably, $R_2$ is hydrogen or methyl; and more preferably hydrogen.

In one embodiment, compounds of Formula (I) or enantiomers, diastereomers, or pharmaceutically-acceptable salts thereof, are provided wherein $R_3$ is H, OH, or methyl.

In one embodiment, compounds of Formula (I) or enantiomers, diastereomers, or pharmaceutically-acceptable salts thereof, are provided wherein q is zero or 1, and preferably q is zero. In this embodiment, when q is 1, preferably $R_5$ is methyl, —$CH_2F$, —$CHF_2$, —$CF_3$, F, Cl, or CN, and more preferably, $R_5$ is methyl, F, or Cl.

In one embodiment, compounds of Formula (I) or enantiomers, diastereomers, or pharmaceutically-acceptable salts thereof, are provided wherein $R_6$ is hydrogen, methyl, —$CH_2F$, —$CHF_2$, —$CF_3$, F, Cl, or CN.

In one embodiment, compounds of Formula (I) or enantiomers, diastereomers, or pharmaceutically-acceptable salts thereof, are provided wherein $R_7$ is aryl or heteroaryl optionally substituted with one or more of methyl, $CF_3$, CN, or halogen. Preferably, $R_7$ is aryl or heteroaryl optionally substituted with F or Cl, and more preferably, $R_7$ is aryl or heteroaryl optionally substituted with F.

The term "treat", "treating", or "treatment," in all grammatical forms, as used herein refers to the prevention, reduction, or amelioration, partial or complete alleviation, or cure of a disease, disorder, or condition, wherein prevention indicates treatment of a person at risk for developing such a disease, disorder or condition.

In one embodiment, a method is provided for treating a disease or disorder selected from a metabolic disease or an inflammatory or immune disease which comprises administering to a patient in need thereof of treatment, a therapeutically effective amount of a compound of Formula (I) or enantiomers, diastereomers, or pharmaceutically-acceptable salts thereof.

In one embodiment, a method is provided for treating a disease or disorder selected from a metabolic disease, which comprises administering to a patient in need thereof of treatment, a therapeutically effective amount of a compound of Formula (I) or enantiomers, diastereomers, or pharmaceutically-acceptable salts thereof, wherein said metabolic disease is selected from Type I diabetes, Type II diabetes, and obesity.

In another embodiment of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, inflammatory disease, autoimmune disease, diabetes, obesity, and neoplastic disease, as well as other uses as described herein, which including a therapeutically effective amount (depending upon use) of a compound of formula (I) of the invention and a pharmaceutically acceptable carrier.

In another embodiment of the present invention, there is provided pharmaceutical compositions useful in treating endocrine disorders, rheumatic disorders, collagen diseases, dermatologic disease, allergic disease, ophthalmic disease, respiratory disease, hematologic disease, gastrointestinal disease, inflammatory disease, immune disease, and neoplastic disease, as well as other used as described herein, which includes a therapeutically effective amount (depending upon use) of a compound of Formula (I) and a pharmaceutically acceptable carrier.

In still another embodiment, the present invention provides a method of treating endocrine disorders, rheumatic disorders, collagen diseases, dermatologic disease, allergic disease, ophthalmic disease, respiratory disease, hematologic disease, gastrointestinal disease, inflammatory disease, autoimmune disease, metabolic disease (diabetes and/or obesity), and neoplastic disease. A disease associated with the expression product of a gene whose transcription is stimulated or repressed by glucocorticoid receptors, or a disease associated with AP-1- and/or NF-κB-induced transcription, or a disease associated with AP-1 and/or NF-κB dependent gene expression, wherein the disease is associated with the expression of a gene under the regulatory control of AP-1 and/or NF-κB (particularly AP-1), including inflammatory and immune diseases and disorders as described hereinafter, which includes the step of administering a therapeutically effective amount of a compound of formula (I) of the invention to a patient.

Another embodiment of the present invention involves a method for treating a disease or disorder associated with the expression product of a gene whose transcription is stimulated or repressed by glucocorticoid receptors, or a method of treating a disease or disorder associated with AP-1- and/or NF-κB- (particularly AP-1-) induced transcription, or a method for treating a disease or disorder associated with AP-1 and/or NF-κB (particularly AP-1) dependent gene expression, wherein the disease is associated with the expression of a gene under the regulatory control of AP-1 and/or NF-κB (particularly AP-1), such as inflammatory and immune disorders, cancer and tumor disorders, such as solid tumors, lymphomas and leukemia, and fungal infections such as mycosis fungoides.

The term "disease associated with GR transactivation," as used herein, refers to a disease associated with the transcription product of a gene whose transcription is transactivated by a GR. Such diseases include, but are not limited to: osteoporosis, diabetes, glaucoma, muscle loss, facial swelling, personality changes, hypertension, obesity, depression, and AIDS, the condition of wound healing, primary or secondary andrenocortical insufficiency, and Addison's disease.

The terms "glucocorticoid receptor" and "GR," as used herein, refer either to a member of the nuclear hormone receptor ("NHR") family of transcription factors which bind glucocorticoids and either stimulate or repress transcription, or to GR-beta.

These terms, as used herein, refer to glucocorticoid receptor from any source, including but not limited to: human glucocorticoid receptor as disclosed in Weinberger et al., Science, 228:740-742 (1985), and in Weinberger et al., Nature, 318:670-672 (1986); rat glucocorticoid receptor as disclosed in Miesfeld R., Nature, 312:779-781 (1985); mouse glucocorticoid receptor as disclosed in Danielson, M. et al., EMBO J., 5:2513; sheep glucocorticoid receptor as disclosed in Yang, K. et al., J. Mol. Endocrinol., 8:173-180 (1992); marmoset glucocorticoid receptor as disclosed in Brandon, D. D. et al., J. Mol. Endocrinol. 7:89-96 (1991); and human GR-beta as disclosed in Hollenberg, S. M. et al., Nature, 318:635 (1985); Bamberger, C. M. et al., J. Clin Invest., 95:2435 (1995).

The term, "disease or disorder associated with AP-1 and/or NF-κB" as used herein, refers to a disease associated with the expression product of a gene under the regulatory control of AP-1 and/or NF-κB. Such diseases include, but are not limited to: inflammatory and immune diseases and disorders; cancer and tumor disorders, such as solid tumors, lymphomas and leukemia; and fungal infections such as mycosis fungoides.

The term "inflammatory or immune associated diseases or disorders" is used herein to encompass any condition, disease, or disorder that has an inflammatory or immune component, including, but not limited to, each of the following conditions: transplant rejection (e.g., kidney, liver, heart, lung, pancreas (e.g., islet cells), bone marrow, cornea, small bowel, skin allografts, skin homografts (such as employed in burn treatment), heart valve xenografts, serum sickness, and graft vs. host disease, autoimmune diseases, such as rheumatoid arthritis, psoriatic arthritis, multiple sclerosis, Type I and Type II diabetes, juvenile diabetes, obesity, asthma, inflammatory bowel disease (such as Crohn's disease and ulcerative colitis), pyoderma gangrenum, lupus (systemic lupus erythematosis), myasthenia gravis, psoriasis, dermatitis, dermatomyositis, eczema, seborrhea, pulmonary inflammation, eye uveitis, hepatitis, Graves' disease, Hashimoto's thyroiditis, autoimmune thyroiditis, Behcet's or Sjorgren's syndrome (dry eyes/mouth), pernicious or immunohaemolytic anaemia, atherosclerosis, Addison's disease (autoimmune disease of the adrenal glands), idiopathic adrenal insufficiency, autoimmune polyglandular disease (also known as autoimmune polyglandular syndrome), glomerulonephritis, scleroderma, morphea, lichen planus, vitiligo (depigmentation of the skin), alopecia greata, autoimmune alopecia, autoimmune hypopituitarism, Guillain-Barre syndrome, and alveolitis; T-cell mediated hypersensitivity diseases, including contact hypersensitivity, delayed-type hypersensitivity, contact dermatitis (including that due to poison ivy), uticaria, skin allergies, respiratory allergies (hay fever, allergic rhinitis) and gluten-sensitive enteropathy (Celiac disease); inflammatory diseases such as osteoarthritis, acute pancreatitis, chronic pancreatitis, acute respiratory distress syndrome, Sezary's syndrome and vascular diseases which have an inflammatory and or a proliferatory component such as restenosis, stenosis and atherosclerosis. Inflammatory or immune associated diseases or disorders also includes, but is not limited to: endocrine disorders, rheumatic disorders, collagen diseases, dermatologic disease, allergic disease, ophthalmic disease, respiratory disease, hematologic disease, gastrointestinal disease, inflammatory disease, autoimmune disease, congenital adrenal hyperplasia, nonsuppurative thyroiditis, hypercalcemia associated with cancer, juvenile rheumatoid arthritis, ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, multiple sclerosis, chronic obstructive pulmonary disease, solid organ transplant rejection, and sepsis. Preferred treatments include treatment of transplant rejection, rheumatoid arthritis, psoriatic arthritis, multiple sclerosis, asthma, inflammatory bowel disease, systemic lupus erythematosis, psoriasis and chronic pulmonary disease.

Accordingly, one embodiment of the present invention is a method of treating a disease or disorder selected from an endocrine disorder, rheumatic disorder, collagen disease, dermatologic disease, allergic disease, ophthalmic disease, respiratory disease, hematologic disease, gastrointestinal disease, inflammatory disease, immune disease, neoplastic disease and metabolic disease, which comprise administering to a patient in need of treatment, a therapeutically effective amount of a compound of Formula (I).

In a preferable embodiment the disease or disorder is an inflammatory or autoimmune disease selected from transplant rejection of kidney, liver, heart, lung, pancreas, bone marrow, cornea, small bowel, skin allografts, skin homografts, heart valve xenograft, serum sickness, and graft vs. host disease, rheumatoid arthritis, psoriatic arthritis, multiple sclerosis, asthma, inflammatory bowel disease, Crohn's disease, ulcerative colitis, pyoderma gangrenum, systemic lupus erythematosis, myasthenia gravis, psoriasis, dermatitis, dermatomyositis, eczema, seborrhoea, pulmonary inflammation, eye uveitis, hepatitis, Graves' disease, Hashimoto's thyroiditis, autoimmune thyroiditis, Behcet's or Sjorgren's syndrome, pernicious or immunohaemolytic anaemia, atherosclerosis, Addison's disease, idiopathic adrenal insufficiency, autoimmune polyglandular disease, glomerulonephritis, scleroderma, morphea, lichen planus, vitiligo, alopecia greata, autoimmune alopecia, autoimmune hypopituitarism, Guillain-Barre syndrome, alveolitis, contact hypersensitivity, delayed-type hypersensitivity, contact dermatitis, uticaria, skin allergies, respiratory allergies, hay fever, gluten-sensitive enteropathy, osteoarthritis, acute pancreatis, chronic pancreatitis, acute respiratory distress syndrome, Sezary's syndrome, restenosis, stenosis, congenital adrenal hyperplasia, nonsuppurative thyroiditis, hypercalcemia associated with cancer, juvenile rheumatoid arthritis, ankylosing spondylitis, acute and subacute bursitis, acute nonspecific tenosynovitis, acute gouty arthritis, post-traumatic osteoarthritis, synovitis of osteoarthritis, epicondylitis, acute rheumatic carditis, pemphigus, bullous dermatitis herpetiformis, severe erythema multiforme, exfoliative dermatitis, seborrheic dermatitis, seasonal or perennial allergic rhinitis, bronchial asthma, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemias and lymphomas in adults, acute leukemia of childhood, regional enteritis, autoimmune vasculitis, sepsis, and chronic obstructive pulmonary disease.

In an even more preferable embodiment, the disease or disorder is selected from transplant rejection, rheumatoid arthritis, psoriatic arthritis, multiple sclerosis, asthma, inflammatory bowel disease, systemic lupus, erythematosis, and psoriasis.

In addition, in accordance with the present invention a method of treating a disease associated with AP-1-induced and/or NF-κB-induced transcription (particularly AP-1-induced transcription) is provided wherein a compound of formula (I) of the invention is administered to a patient at risk of developing the disease in a therapeutically effective amount to induce NHR transrepression of the AP-1-induced and/or NF-κB-induced transcription (particularly AP-1-induced transcription), thereby treating the disease.

In a particular embodiment, the compounds of the present invention are useful for the treatment of the aforementioned exemplary disorders irrespective of their etiology, for example, for the treatment of transplant rejection, rheumatoid arthritis, inflammatory bowel disease, and viral infections.

Other therapeutic agents, such as those described hereafter, may be employed with the compounds of the invention in the present methods. In the methods of the present invention, such other therapeutic agent(s) may be administered prior to, simultaneously with or following the administration of the compound(s) of the present invention.

In still another embodiment, pharmaceutical combinations are contemplated comprising a compound as defined in Claim 1, an enantiomer, diastereomer, or tautomer thereof, or a prodrug ester thereof, or a pharmaceutically-acceptable salt thereof, and an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fabric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

More preferred combinations are those wherein the antidiabetic agent is 1, 2, 3 or more of metformin, glyburide, glimepiride, glipyride, glipizide, chlorpropamide, gliclazide, acarbose, miglitol, pioglitazone, troglitazone, rosiglitazone, insulin, G1-262570, isaglitazone, JTT-501, N,N-2344, L895645, YM-440, R-119702, AJ9677, repaglinide, nateglinide, KAD1129, AR-H039242, GW-409544, KRP297, AC2993, LY315902, P32/98 and/or NVP-DPP-728A, wherein the anti-obesity agent is orlistat, ATL-962, AJ9677, L750355, CP331648, sibutramine, topiramate, axokine, dexamphetamine, phentermine, phenylpropanolamine, and/or mazindol, wherein the lipid-lowering agent is pravastatin, lovastatin, simvastatin, atorvastatin, cerivastatin, fluvastatin, itavastatin, visastatin, fenofibrate, gemfibrozil, clofibrate, avasimibe, TS-962, MD-700, cholestagel, niacin and/or LY295427, wherein the antihypertensive agent is an ACE inhibitor which is captopril, fosinopril, enalapril, lisinopril, quinapril, benazepril, fentiapril, ramipril or moexipril; an NEP/ACE inhibitor which is omapatrilat, [S[(R*,R*)]-hexahydro-6-[(2-mercapto-1-oxo-3-phenylpropyl)amino]-2,2-dimethyl-7-oxo-1H-azepine-1-acetic acid (gemopatrilat) or CGS 30440;

an angiotensin II receptor antagonist which is irbesartan, losartan or valsartan;

amlodipine besylate, prazosin HCl, verapamil, nifedipine, nadolol, propranolol, carvedilol, or clonidine HCl, wherein the platelet aggregation inhibitor is aspirin, clopidogrel, ticlopidine, dipyridamole or ifetroban;

the immunosuppressant is a cyclosporin, mycophenolate, interferon-beta, deoxyspergolin, FK-506 or Ant.-IL-2;

the anti-cancer agent is azathiprine, 5-fluorouracel, cyclophosphamide, cisplatin, methotrexate, thiotepa, or carboplatin;

the anti-viral agent is abacavir, aciclovir, ganciclovir, zidanocin, or vidarabine; and the antiinflammatory drug is ibuprofen, celecoxib, rofecoxib, aspirin, naproxen, ketoprofen, diclofenac sodium, indomethacin, piroxicam, prednisone, dexamethasone, hydrocortisone, or triamcinolone diacetate.

The invention may be embodied in other specific forms without departing from the spirit or essential attributes thereof. This invention also encompasses all combinations of alternative aspects and embodiments of the invention noted herein. It is understood that any and all embodiments may be taken in conjunction with any other embodiment to describe additional embodiments of the present invention. Furthermore, any elements of an embodiment are meant to be combined with any and all other elements from any of the embodiments to describe additional embodiments.

METHODS OF PREPARATION

The compounds of the present invention may be synthesized by various methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds. Examples of compounds of the present invention prepared by methods described in the general schemes are given in the examples section set out hereinafter. Example compounds are typically prepared as racemic mixtures. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

Compounds of Formula (I) of the invention can be prepared as described by the schemes and examples below. In the schemes the various groups A, D, $R_1$, $R_2$, $R_3$, $R_4$, $R_5$, $R_6$, $R_7$, and q correspond to those described above.

SCHEME 1

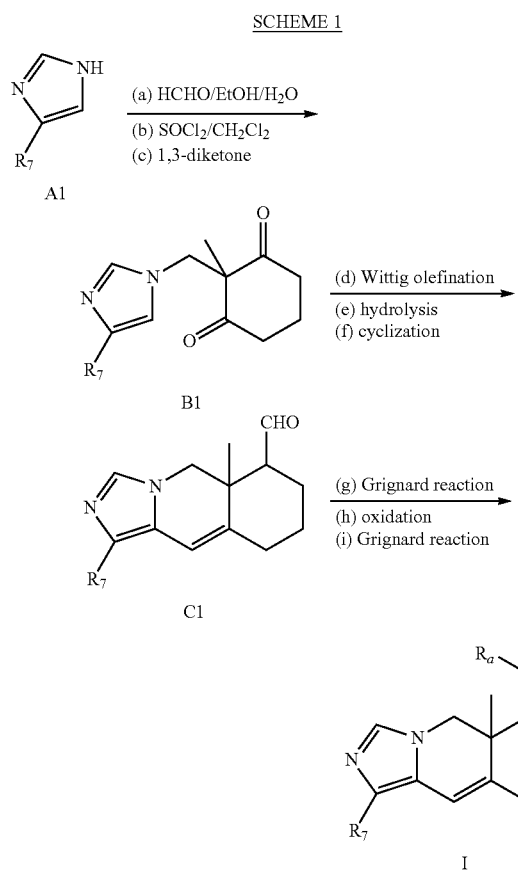

Scheme 1 illustrates a method for synthesizing compounds of Formula (I) (where A=carbon and D is nitrogen). Compounds of type A1 are commercially available or can be prepared by methods known in the art (for example, see Chemische Berichte, 86:1085-1095 (1953); Journal of Medicinal Chemistry, 47(12):2995-3008 (2004)) or as detailed below in the experimental section. Hydroxymethylation followed by chlorination gave the chloromethyl imidazole. Alkylation of 1,3-diketone with the chloromethyl imidazole can be accomplished by a variety of methods known in the art (for example see, in Larock, R. C., Comprehensive Organic Transformations, Second Edition, VCH Publishers, Inc. (1999) or Synthesis, 1069-1070 (1995)) to give product B1. Conversion of the diketone B1 to an appropriate alkene, for example, using Wittig olefination, followed by hydrolysis and cyclization, provides the aldehyde C1. Treatment of the aldehyde C1 with a Grignard reagent or an alkyl or aryl lithium affords compounds of Formula (I). The Grignard or alkyl aryl lithium reagents are either commercially available or can be prepared by methods well known in the art (for example see Angew. Chem. Int. Ed., 4302-4320 (2003) and references cited therein). This secondary alcohol can be oxidized by methods known in the art (for example see, in Larock, R. C., "Comprehensive Organic Transformations", $2^{nd}$ edition, 1999, VCH Publishers, Inc or Trahanovsky, "Oxidations in organic chemistry", Publisher, Academic Pr). Grignard reaction of the ketone then affords compounds of Formula (I) (where $R_3$=H; $R_4$=$CR_aR_bOH$).

SCHEME 2

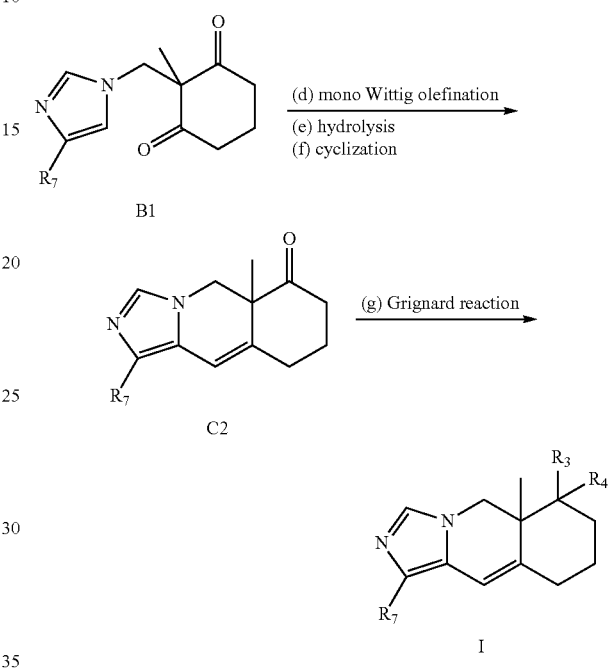

Scheme 2 illustrates an alternative approach to compounds of Formula (I). Mono-olefination of B1 using an appropriate olefinating reagent, for example the Wittig reagent, gives a ketone-aldehyde intermediate after hydrolysis. Cyclization of the keto-aldehyde intermediate yields the ketone C2. The ketone intermediate C2 can be converted into various compounds of Formula (I) by a variety of methods known in the art (for example see, in Larock, R. C., Comprehensive Organic Transformations, Second Edition, VCH Publishers, Inc. (1999)). For example, Grignard reaction gives compounds of Formula (I) (where $R_3$=OH; $R_4$=aryl, heteroaryl, aralkyl, or araheteroalkyl).

SCHEME 3

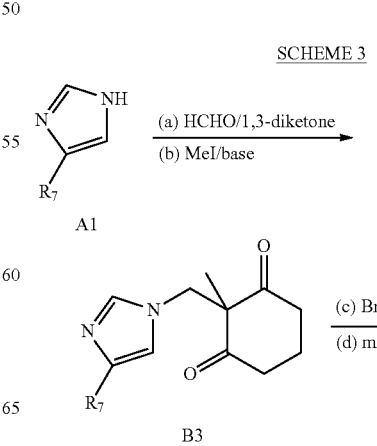

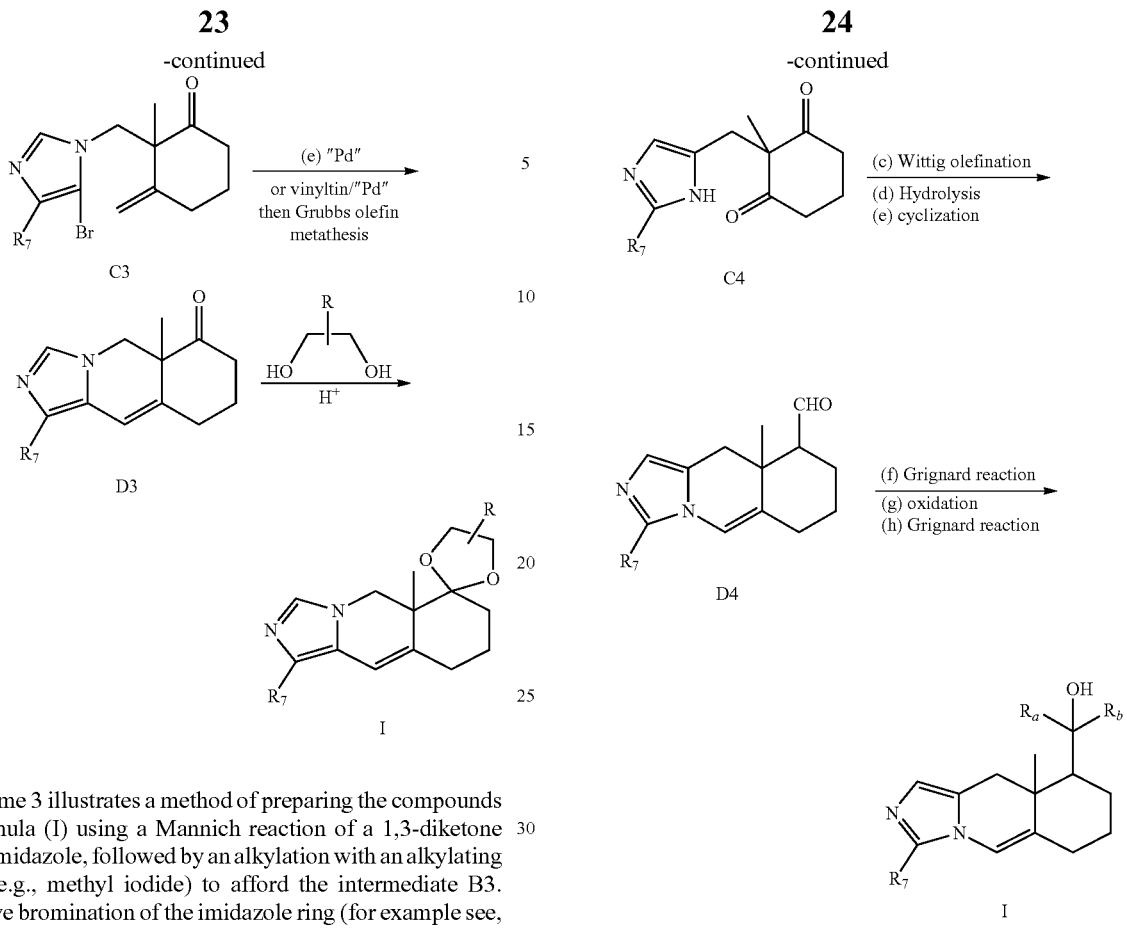

Scheme 3 illustrates a method of preparing the compounds of Formula (I) using a Mannich reaction of a 1,3-diketone with a imidazole, followed by an alkylation with an alkylating agent (e.g., methyl iodide) to afford the intermediate B3. Selective bromination of the imidazole ring (for example see, *J. Org. Chem.*, 71(8):3159-3166 (2006)) and Wittig olefination provide intermediate C3, which can be cyclized in the presence of a palladium catalyst (for example an intramolecular Heck reaction, see *Organic Reactions*, 60:157-534 (2002)) to afford intermediate D3. Alternatively, Stille coupling of C3 with, for example, vinyltrimethylin compound followed by olefin metathesis (for example see. *Angew. Chem. Int. Ed.*, 45(37):6082-6085 (2006) and references cited therein) affords D3. The carbonyl intermediate D3 can be converted into various compounds of Formula (I) by methods known in the art (for example see, in Larock, R. C., Comprehensive Organic Transformations, Second Edition, VCH Publishers, Inc. (1999)). For example, the intermediate D3 can be heated with ethylene glycol compound in the presence of an appropriate acid to give the acetal shown in Scheme 3.

Scheme 4 shows a method of preparing compounds of Formula (I), where A is nitrogen and D is carbon. Carbamidines or carbamidine salts A4 are commercially available or can be prepared by methods known in the art (for example, see *Heterocycles*, 60(5):1133-1145 (2003)). Treatment of carbamidines with dihydroxyacetone affords hydroxymethylimidazole B4 (for example, see *Synthesis*, 7:576 (1983)). B4 when subjected to procedures described in Scheme 1 gives the corresponding compounds of Formula (I).

SCHEME 4

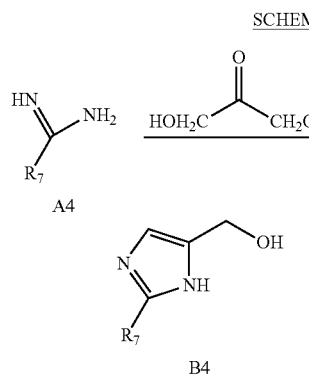

SCHEME 5

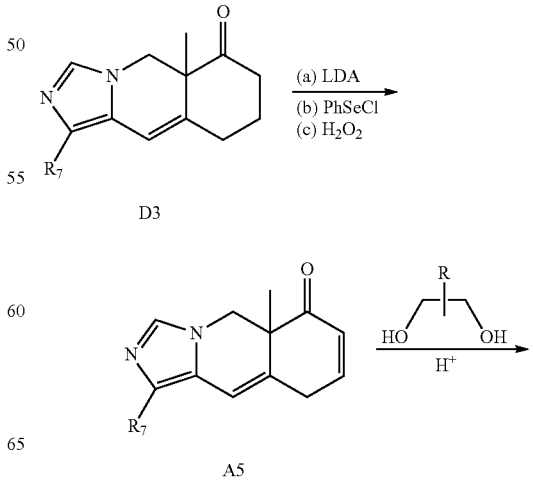

-continued

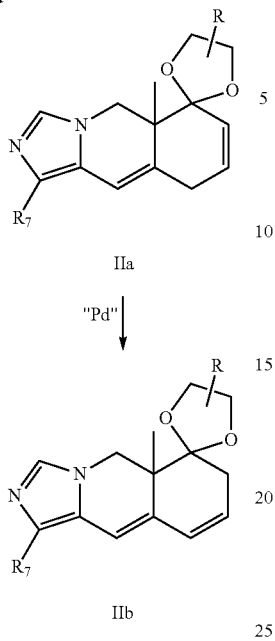

IIa

IIb

Scheme 5 illustrates a method of preparing the compounds of Formula (II). A5 can be prepared from D3 (Scheme 3) using a selenoxide reaction. The carbonyl intermediate A5 can be converted into compounds of Formula (II) by methods known in the art (for example see, in Larock, R. C., Comprehensive Organic Transformations, Second Edition, VCH Publishers, Inc. (1999)). For example, intermediate A5 on treatment with ethylene glycol in the presence of an acid, for example p-toluenesulfonic acid to give the acetal IIa. Acetal IIa can be isomerized into a thermodynamically more stable form IIb, using a palladium catalyst.

SCHEME 6

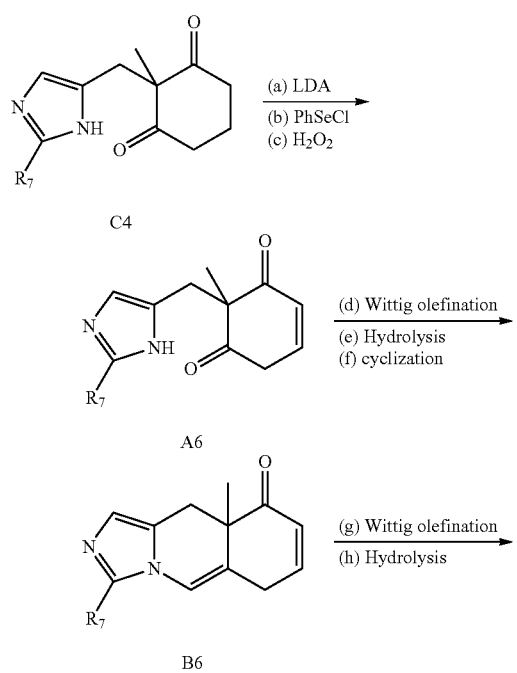

-continued

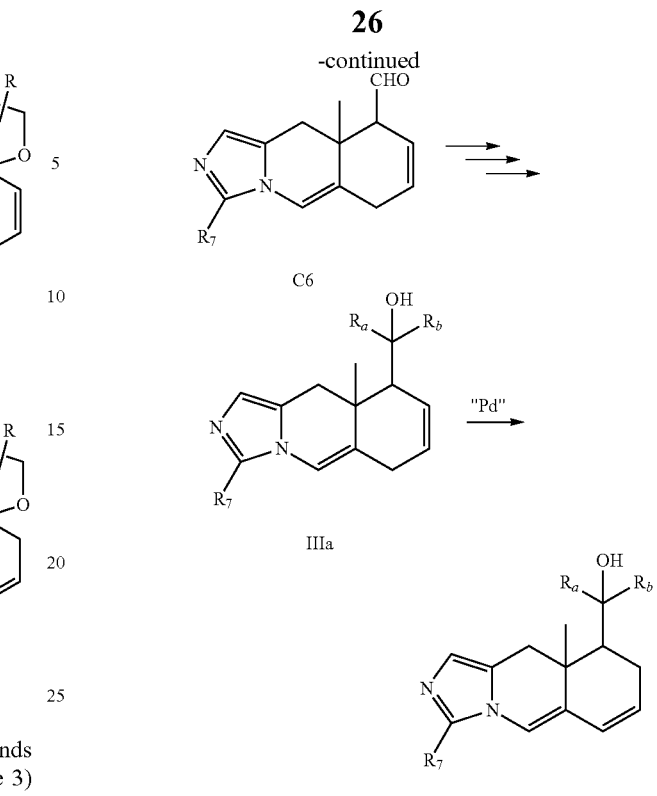

IIIa

IIIb

Scheme 6 shows a method of preparing compounds of Formula (III). A6 can be prepared from C4 (Scheme 4) using a selenoxide reaction. Conversion of the diketone A6 to an appropriate alkene, for example, using (methoxymethyl)triphenylphosphonium chloride, followed by hydrolysis and cyclization, provides the ketone B6. The ketone B6 can be converted into C6 using a similar sequence as outlined for B6. C6 when subjected to procedures described in Scheme 1 gives compounds of Formula (IIIa). (where $R_3$=H; $R_4$=$CR_aR_bOH$). IIIa can be converted into a thermodynamically more stable IIIb using a palladium catalyst.

DEFINITIONS

The following are definitions of terms used in this specification and appended claims. The initial definition provided for a group or term herein applies to that group or term throughout the specification and claims, individually or as part of another group, unless otherwise indicated.

The term "alkyl" alone or as part of another group refers to straight or branched chain hydrocarbon groups having 1 to 12 carbon atoms, preferably 1 to 8 carbon atoms. Lower alkyl groups, that is, alkyl groups of 1 to 4 carbon atoms, are most preferred. When numbers appear in a subscript after the symbol "C", the subscript defines with more specificity the number of carbon atoms that a particular group may contain. For example, "$C_{1-6}$alkyl" refers to straight and branched chain alkyl groups with one to six carbon atoms, such as methyl, ethyl, n-propyl, isopropyl, n-butyl, t-butyl, n-pentyl, and so forth. The subscript "0" refers to a bond. Thus, the term hydroxy($C_{0-2}$)alkyl or ($C_{0-2}$)hydroxyalkyl includes hydroxy, hydroxymethyl and hydroxyethyl.

"Alkyl" includes "unsubstituted" and "substituted alkyl" where the alkyl may be substituted with any of the substituents for substituted alkyl set out below.

The term "substituted alkyl" refers to an alkyl group as defined above having one, two, or three substituents independently selected from the group consisting of halo (e.g., trifluoromethyl), alkenyl, substituted alkenyl, alkynyl, nitro, cyano, oxo (=O), OR$_a$, SR$_a$, (=S), —NR$_a$R$_b$, —N(alkyl)$_3^+$, —NR$_a$SO$_2$, —NR$_a$SO$_2$R$_c$, —SO$_2$R$_c$, —SO$_2$NR$_a$R$_b$, —SO$_2$NR$_a$C(=O)R$_b$, SO$_3$H, —PO(OH)$_2$, —C(=O)R$_a$, —CO$_2$R$_a$, —C(=O)NR$_a$R$_b$, —C(=O)(C$_{1-4}$alkylene)NR$_a$R$_b$, —C(=O)NR$_a$(SO$_2$)R$_b$, —CO$_2$(C$_{1-4}$alkylene)NR$_a$R$_b$, —NR$_a$C(=O)R$_b$, —NR$_a$CO$_2$R$_b$, —NR$_a$(C$_{1-4}$alkylene)CO$_2$R$_b$, =N—OH, =N—O-alkyl, aryl, cycloalkyl, heterocyclo, and/or heteroaryl, wherein R$_a$ and R$_b$ are the same or different and are independently selected from hydrogen, alkyl, alkenyl, CO$_2$H, CO$_2$(alkyl), C$_{3-7}$cycloalkyl, phenyl, benzyl, phenylethyl, naphthyl, a four to seven membered heterocyclo, or a five to six membered heteroaryl, or when attached to the same nitrogen atom may join to form a heterocyclo or heteroaryl, and R$_c$ is selected from same groups as R$_a$ and R$_b$ but is not hydrogen. Each group R$_a$ and R$_b$ when other than hydrogen, and each R$_c$ group optionally has up to three further substituents attached at any available carbon or nitrogen atom of R$_a$, R$_b$, and/or R$_c$, said substituent(s) being the same or different and are independently selected from the group consisting of (C$_{1-6}$)alkyl, (C$_{2-6}$)alkenyl, hydroxy, halogen, cyano, nitro, CF$_3$, O(C$_{1-6}$alkyl), OCF$_3$, C(=O)H, C(=O)(C$_{1-6}$alkyl), CO$_2$H, CO$_2$(C$_{1-6}$alkyl), NHCO$_2$(C$_{1-6}$alkyl), —S(C$_{1-6}$alkyl), —NH$_2$, NH(C$_{1-6}$alkyl), N(C$_{1-6}$alkyl)$_2$, N(CH$_3$)$_3^+$, SO$_2$(C$_{1-6}$alkyl), —C(=O)(C$_{1-4}$alkylene)NH$_2$, —C(=O)(C$_{1-4}$alkylene)NH(alkyl), C(=O)(C$_{1-4}$alkylene)N(C$_{1-4}$alkyl)$_2$, C$_{3-7}$cycloalkyl, phenyl, benzyl, phenylethyl, phenyloxy, benzyloxy, naphthyl, a four to seven membered heterocyclo, or a five to six membered heteroaryl. When a substituted alkyl is substituted with an aryl, heterocyclo, cycloalkyl, or heteroaryl group, said ringed systems are as defined below and thus may have zero, one, two, or three substituents, also as defined below and/or as defined for substituted alkyl.

One skilled in the field will understand that, when the designation "CO$_2$" is used herein, this is intended to refer to the group

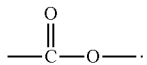

When the term "alkyl" is used together with another group, such as in "arylalkyl", this conjunction defines with more specificity at least one of the substituents that the substituted alkyl will contain. For example, "arylalkyl" refers to a substituted alkyl group as defined above where at least one of the substituents is an aryl, such as benzyl. Thus, the term aryl(C$_{0-4}$)alkyl includes a substituted lower alkyl having at least one aryl substituent and also includes an aryl directly bonded to another group, i.e., aryl(C$_0$)alkyl.

The term "alkenyl" (which includes unsubstituted or substituted alkenyl) alone or as part of another group refers to straight or branched chain hydrocarbon groups having 2 to 12 carbon atoms and at least one double bond. Alkenyl groups of 2 to 6 carbon atoms and having one double bond are most preferred.

The term "alkynyl" (which includes unsubstituted or substituted alkynyl) alone or as part of another group refers to straight or branched chain hydrocarbon groups having 2 to 12 carbon atoms and at least one triple bond. Alkynyl groups of 2 to 6 carbon atoms and having one triple bond are most preferred.

The term "alkylene" (which includes unsubstituted or substituted alkylene) alone or as part of another group refers to bivalent straight or branched chain hydrocarbon groups having 1 to 12 carbon atoms, preferably 1 to 8 carbon atoms, e.g., {—CH$_2$—}$_n$, wherein n is 1 to 12, preferably 1-8. Lower alkylene groups, that is, alkylene groups of 1 to 4 carbon atoms, are most preferred. The terms "alkenylene" and "alkynylene" refer to bivalent radicals of alkenyl and alkynyl groups, respectively, as defined above.

When reference is made to a substituted alkenyl, alkynyl, alkylene, alkenylene, or alkynylene group, these groups are substituted with one to three substituents as defined above for substituted alkyl groups.

The term "heteroalkylene" (which includes unsubstituted and "substituted heteroalkylene") alone or as part of another group is used herein to refer to saturated and unsaturated bivalent straight or branched chain hydrocarbon groups having 2 to 12 carbon atoms, preferably 2 to 8 carbon atoms, wherein one or two carbon atoms in the straight chain are replaced by heteroatom(s) selected from —O—, —S—, —S(=O)—, —SO$_2$—, —NH—, and —NHSO$_2$—. Thus, the term "heteroalkylene" includes bivalent alkoxy, thioalkyl, and aminoalkyl groups, as defined below, as well as alkylene and alkenylene groups having a combination of heteroatoms in the alkyl chain. As an illustration, a "heteroalkylene" herein may comprise groups such as —S—(CH$_2$)$_{1-5}$NH—CH$_2$—, —O—(CH$_2$)$_{1-5}$S(=O)—CH$_2$—, —NHSO$_2$—CH$_2$—, —CH$_2$—NH—, and so forth. Preferably, a heteroalkylene does not have two adjacent atoms simultaneously selected from —O— and —S—. When a subscript is used with the term heteroalkylene, e.g., as in C$_{2-3}$heteroalkylene, the subscript refers to the number of carbon atoms in the group in addition to heteroatoms. Thus, for example, a C$_{1-2}$heteroalkylene may include groups such as —NH—CH$_2$—, —CH$_2$—NH—CH$_2$—, —CH$_2$—CH$_2$—NH—, —S—CH$_2$—, —CH$_2$—S—CH$_2$—, —O—CH$_2$—NH—CH$_2$—, CH$_2$—O—CH$_2$ and so forth.

The term "substituted heteroalkylene" refers to a heteroalkylene group as defined above wherein at least one of the nitrogen or carbon atoms in the heteroalkylene chain is bonded to (or substituted with) a group other than hydrogen. Carbon atoms in the heteroalkylene chain may be substituted with a group selected from those recited above for substituted alkyl groups, or with a further alkyl or substituted alkyl group. Nitrogen atoms of the heteroalkylene chain may be substituted with a group selected from alkyl, alkenyl, alkynyl, cyano, or A$_1$-Q-A$_2$-R$_h$, wherein A$_1$ is a bond, C$_{1-2}$alkylene, or C$_{2-3}$alkenylene; Q is a bond, —C(=O)—, —C(=O)NR$_d$—, —C(=S)NR$_d$—, —SO$_2$—, —SO$_2$NR$_d$—, —CO$_2$—, or —NR$_d$CO$_2$—; A$_2$ is a bond, C$_{1-3}$alkylene, C$_{2-3}$alkenylene, —C$_{1-4}$alkylene-NR$_d$—, —C$_{1-4}$alkylene-NR$_d$C(=O)—, —C$_{1-4}$alkylene-S—, —C$_{1-4}$alkylene-SO$_2$—, or —C$_{1-4}$alkylene-O—, wherein said A$_2$ alkylene groups are branched or straight chain and optionally substituted as defined herein for substituted alkylene; R$_h$ is hydrogen, alkyl, substituted alkyl, alkenyl, substituted alkenyl, aryl, heteroaryl, heterocyclo, or cycloalkyl; and R$_d$ is selected from hydrogen, alkyl, and substituted alkyl, as defined herein, provided, however, that for a substituted heteroalkylene R$_h$ is not hydrogen when A$_1$, Q and A$_2$ are each bonds. When R$_h$ is aryl, heteroaryl, cycloalkyl, or heterocyclo, these rings are, in turn, optionally substituted with one to three groups as defined below in the definitions for these terms.

The term "alkoxy" refers to an alkyl or substituted alkyl group as defined above having one or two oxygen atoms (—O—) in the alkyl chain. For example, the term "alkoxy"

includes the groups —O—$C_{1-12}$alkyl, —($C_{1-6}$alkylene)-O—$C_{1-6}$alkyl, —($C_{1-4}$alkylene-O—$C_{1-4}$alkylene)-O—$C_{1-4}$alkyl, and so forth.

The term "thioalkyl" or "alkylthio" refers to an alkyl or substituted alkyl group as defined having one or two sulfur atoms in the alkyl chain. For example, the term "thioalkyl" or "alkylthio" includes the groups —S—$C_{1-12}$alkyl, —(S—$C_{1-6}$alkylene)-S—$C_{1-6}$alkyl, and so forth.

The terms "aminoalkyl" or "alkylamino" refer to an alkyl or substituted alkyl group as defined above having one or two nitrogen (—NR—) atoms in the alkyl chain. For example, the term "aminoalkyl" includes the groups —NR—$C_{1-12}$alkyl, —NR—$C_{1-6}$alkylene-NR—$C_{1-6}$alkyl, etc. (where R is preferably hydrogen but may include alkyl or substituted alkyl as defined above.) When a subscript is used with reference to an alkoxy, thioalkyl or aminoalkyl, the subscript refers to the number of carbon atoms that the group may contain in addition to heteroatoms. Thus, for example, monovalent $C_{1-2}$aminoalkyl includes the groups —$CH_2$—$NH_2$, —NH—$CH_3$, —$(CH_2)_2$—$NH_2$, —NH—$CH_2$—$CH_3$, —$CH_2$—$NH_2$—$CH_3$, and —N—$(CH_3)_2$. A lower aminoalkyl comprises an aminoalkyl having one to four carbon atoms. "Amino" refers to the group $NH_2$.

The alkoxy, thioalkyl, or aminoalkyl groups may be monovalent or bivalent. By "monovalent" it is meant that the group has a valency (i.e., ability to combine with another group), of one, and by "bivalent" it is meant that the group has a valency of two. Thus, for example, a monovalent alkoxy includes groups such as —O—$C_{1-12}$alkyl, —$C_{1-6}$alkylene-O—$C_{1-6}$alkyl, —$C_{1-4}$alkylene-O—$C_{1-4}$alkylene-O—$C_{1-4}$alkyl, whereas a bivalent alkoxy includes groups such as —O—$C_{1-12}$alkylene-, —$C_{1-6}$alkylene-O—$C_{1-6}$alkylene-, —$C_{1-4}$alkylene-O—$C_{1-4}$alkylene-O—$C_{1-4}$alkylene-, and so forth.

The term "carbonyl" is intended to designate the group —C(O)—.

The term "acyl" alone or as part of another group refers to a carbonyl group linked to an organic radical, more particularly, the group C(=O)$R_e$, as well as the bivalent groups —C(=O)— or —C(=O)$R_e$—, which are linked to organic radicals or a ring in compounds of Formula (I). The group $R_e$ can be selected from alkyl, alkenyl, alkynyl, aminoalkyl, substituted alkyl, substituted alkenyl, or substituted alkynyl, as defined herein, or when appropriate, the corresponding bivalent group, e.g., alkylene, alkenylene, etc. Accordingly, in compounds of Formula (I), when it is recited that $R_1$ to $R_8$ can be "acyl," this is intended to encompass a selection for $R_1$ to $R_8$ of —C(=O)— and also the groups —C(=O)$R_e$— or —$R_e$C(=O)—, wherein in this instance, the group $R_e$ will be selected from bivalent groups, e.g., alkylene, alkenylene, alkynylene, bivalent aminoalkyl, substituted alkylene, substituted alkenylene, or substituted alkynylene.

The term "alkoxycarbonyl" alone or as part of another group refers to a carboxy group

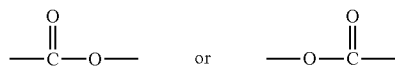

linked to an organic radical ($CO_2R_e$), as well as the bivalent groups —$CO_2$—, —$CO_2R_e$— which are linked to organic radicals in compounds of Formula (I), wherein $R_e$ is as defined above for acyl. The organic radical to which the carboxy group is attached may be monovalent (e.g., —$CO_2$-alkyl or —OC(=O)alkyl), or bivalent (e.g., —$CO_2$-alkylene, —OC(=O)alkylene, etc.). Accordingly, "alkoxycarbonyl" is intended to encompass the groups —$CO_2R_e$— or —$R_eCO_2$—, wherein in this instance, the group $R_e$ will be selected from bivalent groups, e.g., alkylene, alkenylene, alkynylene, bivalent aminoalkyl, substituted alkylene, substituted alkenylene, or substituted alkynylene.

The term "amide" or "amidyl" alone or as part of another group refers to the group C(=O)$NR_aR_b$ (or other R groups other than $R_a$ or $R_b$ linked to an N atom), wherein the groups $R_a$ and $R_b$ are defined as recited above in the definition for substituted alkyl groups.

The term "sulfonyl" alone or as part of another group refers to a sulphoxide group linked to an organic radical in compounds of Formula (I), more particularly, the monovalent group $S(O)_{1-2}$—$R_e$, or the bivalent group —$S(O)_{1-2}$-linked to organic radicals in compounds of Formula (I). Accordingly, in compounds of Formula (I), "sulfonyl," is intended to encompass —S(=O)— or —$SO_2$— as well as the groups —S(=O)$R_e$—, —$R_e$S(=O)—, —$SO_2R_e$—, or —$R_eSO_2$—, wherein in this instance, the group $R_e$ will be selected from those recited above for acyl and alkoxycarbonyl groups.

The term "sulfonamidyl" alone or as part of another group refers to the group —$S(O)_2NR_aR_b$ (or other R groups other than $R_a$ or $R_b$ linked to an N atom), wherein $R_a$ and $R_b$ are as defined above for substituted alkyl groups. Additionally, the sulfonamidyl group may be bivalent, in which case one of the groups $R_a$ and $R_b$ will be a bond. Thus, in compounds of Formula (I), sulfonamidyl is intended to mean the group —$S(O)_2NR_a$—.

The term "cycloalkyl" alone or as part of another group refers to fully saturated and partially unsaturated hydrocarbon rings of 3 to 9, preferably 3 to 6 carbon atoms. Accordingly, the term "cycloalkyl" is intended to include a cycloalkenyl (e.g. cyclohexenyl) ring. The term "cycloalkyl" includes such rings having zero, one, two, or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —N(alkyl)$_3^+$, —$NR_aSO_2$, —$NR_aSO_2R_c$, —$SO_2R_c$, —$SO_2NR_aR_b$, —$SO_2NR_aC$(=O)$R_b$, $SO_3H$, —PO$(OH)_2$, —C(=O)$R_a$, —$CO_2R_a$, —C(=O)$NR_aR_b$, —C(=O)($C_{1-4}$alkylene)$NR_aR_b$, —C(=O)$NR_a(SO_2)R_b$, —$CO_2$($C_{1-4}$alkylene)$NR_aR_b$, —$NR_aC$(=O)$R_b$, —$NR_aCO_2R_b$, —$NR_a$($C_{1-4}$alkylene)$CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above in the definition for substituted alkyl groups. The term "cycloalkyl" also includes such rings having a second ring fused thereto (e.g., including benzo, heterocyclo, or heteroaryl rings) or having a carbon-carbon bridge of 3 to 4 carbon atoms. When a cycloalkyl is substituted with a further ring (or has a second ring fused thereto), said ring in turn is optionally substituted with one to two of ($C_{1-4}$alkyl, ($C_{2-4}$alkenyl, halogen, hydroxy, cyano, nitro, $CF_3$, O($C_{1-4}$alkyl), $OCF_3$, C(=O)H, C(=O)($C_{1-4}$alkyl), $CO_2H$, $CO_2$($C_{1-4}$alkyl), $NHCO_2$($C_{1-4}$alkyl), —S($C_{1-4}$alkyl), —$NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$.

Accordingly, in compounds of formula (I), the term "cycloalkyl" includes cyclopropyl, cyclobutyl, cyclopentyl, cyclohexyl, cycloheptyl, cyclooctyl, etc., as well as the following ring systems:

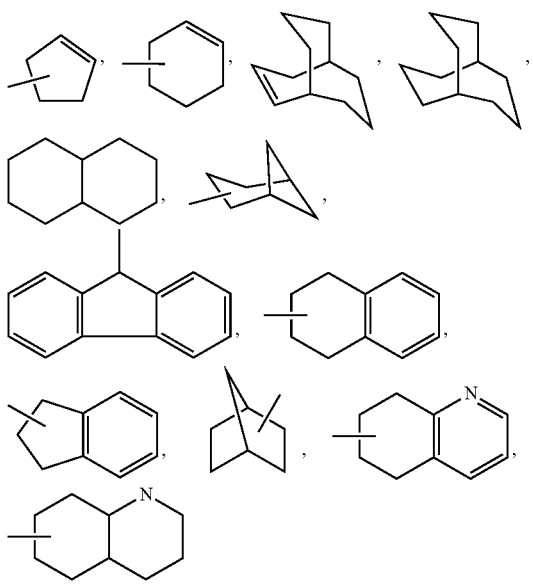

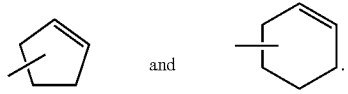

and the like, which optionally may be substituted at any available atoms of the ring(s). Preferred cycloalkyl groups include cyclopropyl, cyclobutyl, cyclopentyl, cyclohexyl, The term "halo" or "halogen" alone or as part of another group refers to chloro, bromo, fluoro and iodo.

The term "haloalkyl" alone or as part of another group means a substituted alkyl having one or more halo substituents. For example, "haloalkyl" includes mono, bi, and trifluoromethyl.

The term "haloalkoxy" alone or as part of another group means an alkoxy group having one or more halo substituents. For example, "haloalkoxy" includes $OCF_3$.

The term "aryl" alone or as part of another group refers to phenyl, biphenyl, 1-naphthyl and 2-naphthyl. The term "aryl" includes such rings having zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above, or any of the substituents for alkyl set out hereinbefore. Additionally, two substituents attached to an aryl, particularly a phenyl group, may join to form a further ring such as a fused or spiro-ring, e.g., cyclopentyl or cyclohexyl, or fused heterocyclo or heteroaryl. When an aryl is substituted with a further ring (or has a second ring fused thereto), said ring in turn is optionally substituted with one to four, preferably one or two of ($C_{1-4}$alkyl, ($C_{2-4}$alkenyl, halogen, hydroxy, cyano, nitro, $CF_3$, $O(C_{1-4}alkyl)$, $OCF_3$, $C(=O)$ H, $C(=O)(C_{1-4}alkyl)$, $CO_2H$, $CO_2(C_{1-4}alkyl)$, $NHCO_2(C_{1-4}alkyl)$, —$S(C_{1-4}alkyl)$, —$NH_2$, $NH(C_{1-4}alkyl)$, $N(C_{1-4}alkyl)_2$, $N(C_{1-4}alkyl)_3^+$, $C(=O)NH_2$, $SO_2(C_{1-4}alkyl)$, $C(=O)(C_{1-4}alkylene)NH_2$, $C(=O)(C_{1-4}alkylene)NH(alkyl)$, and/or $C(=O)(C_{1-4}alkylene)N(C_{1-4}alkyl)_2$.

Thus, examples of aryl groups include:

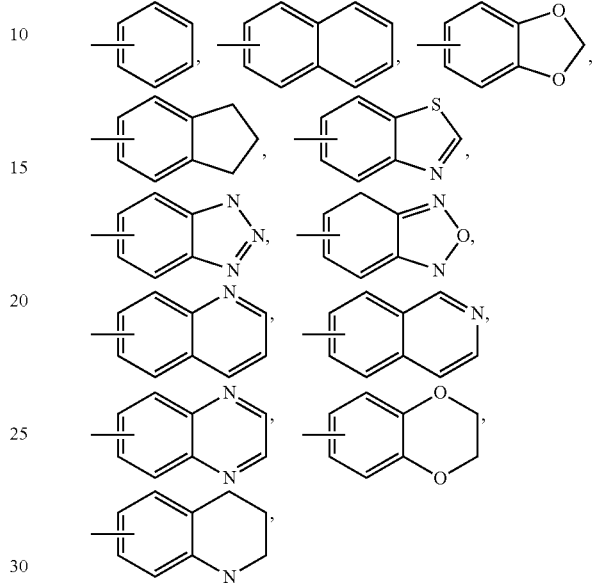

and the like, which optionally may be substituted at any available carbon or nitrogen atom. A preferred aryl group is optionally-substituted phenyl.

The terms "heterocyclo" or "heterocyclic" or "cycloheteroalkyl" alone or as part of another group refers to substituted and unsubstituted non-aromatic 3 to 7 membered monocyclic groups, 7 to 11 membered bicyclic groups, and 10 to 15 membered tricyclic groups, in which at least one of the rings has at least one heteroatom (O, S or N) (also referred to as cycloheteroalkyl or heterocycloalkyl). Each ring of the heterocyclo group containing a heteroatom can contain one or two oxygen or sulfur atoms and/or from one to four nitrogen atoms provided that the total number of heteroatoms in each ring is four or less, and further provided that the ring contains at least one carbon atom. The fused rings completing bicyclic and tricyclic groups may contain only carbon atoms and may be saturated, partially saturated, or unsaturated. The nitrogen and sulfur atoms may optionally be oxidized and the nitrogen atoms may optionally be quaternized. The heterocyclo group may be attached at any available nitrogen or carbon atom. The heterocyclo ring may contain zero, one, two or three substituents selected from the group consisting of halogen, trifluoromethyl, trifluoromethoxy, alkyl, substituted alkyl, alkenyl, substituted alkenyl, alkynyl, nitro, cyano, oxo (=O), $OR_a$, $SR_a$, (=S), —$NR_aR_b$, —$N(alkyl)_3^+$, —$NR_aSO_2$, —$NR_aSO_2R_c$, —$SO_2R_c$, —$SO_2NR_aR_b$, —$SO_2NR_aC(=O)R_b$, $SO_3H$, —$PO(OH)_2$, —$C(=O)R_a$, —$CO_2R_a$, —$C(=O)NR_aR_b$, —$C(=O)(C_{1-4}alkylene)NR_aR_b$, —$C(=O)NR_a(SO_2)R_b$, —$CO_2(C_{1-4}alkylene)NR_aR_b$, —$NR_aC(=O)R_b$, —$NR_aCO_2R_b$, —$NR_a(C_{1-4}alkylene)CO_2R_b$, =N—OH, =N—O-alkyl, aryl, cycloalkyl, heterocyclo, and/or heteroaryl, wherein $R_a$, $R_b$ and $R_c$ are as defined above for substituted alkyl groups, and are also in turn optionally substituted as recited above. When a heterocyclo is substituted with a further ring, said ring in turn is optionally substituted with one to two of ($C_{1-4}$alkyl, ($C_{2-4}$alkenyl, halogen, hydroxy, cyano, nitro, $CF_3$, O($C_{1-4}$alkyl), $OCF_3$, C(=O)H, C(=O)($C_{1-4}$alkyl), $CO_2H$, $CO_2$($C_{1-4}$alkyl), $NHCO_2$($C_{1-4}$alkyl), —S($C_{1-4}$alkyl), —$NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$.

Exemplary monocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidyl, piperazinyl, 2-oxopiperazinyl, 2-oxopiperidyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl and the like. Exemplary bicyclic heterocyclo groups include quinuclidinyl.

Preferred heterocyclo groups in compounds of formula (I) include

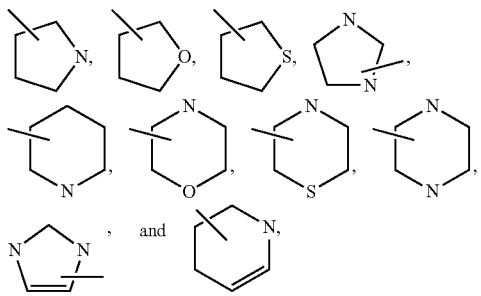

which optionally may be substituted.

The term "heteroaryl" alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halogen, trifluoromethyl, trifluoromethoxy, alkyl, substituted alkyl, alkenyl, substituted alkenyl, alkynyl, nitro, cyano, $OR_a$, $SR_a$, (=S), —$NR_aR_b$, —N(alkyl)$_3^+$, —$NR_aSO_2$, —$NR_aSO_2R_c$, —$SO_2R_c$, —$SO_2NR_aR_b$, —$SO_2NR_aC(=O)R_b$, $SO_3H$, —PO(OH)$_2$, —C(=O)$R_a$, —$CO_2R_a$, —C(=O)$NR_aR_b$, —C(=O)($C_{1-4}$alkylene)$NR_aR_b$, —C(=O)$NR_a$($SO_2$)$R_b$, —$CO_2$($C_{1-4}$alkylene)$NR_aR_b$, oxo(=O), —$NR_aC(=O)R_b$, —$NR_aCO_2R_b$, —$NR_a$($C_{1-4}$alkylene)$CO_2R_b$, aryl, cycloalkyl, heterocyclo, and/or heteroaryl, wherein $R_a$, $R_b$ and $R_c$ are as defined above for substituted alkyl groups, and are also in turn optionally substituted as recited above. When a heteroaryl is substituted with a further ring, said ring in turn is optionally substituted with one to two of ($C_{1-4}$)alkyl, ($C_{2-4}$)alkenyl, halogen, hydroxy, cyano, nitro, $CF_3$, O($C_{1-4}$alkyl), $OCF_3$, C(=O)H, C(=O)($C_{1-4}$alkyl), $CO_2H$, $CO_2$($C_{1-4}$alkyl), $NHCO_2$($C_{1-4}$alkyl), —S($C_{1-4}$alkyl), —$NH_2$, NH($C_{1-4}$alkyl), N($C_{1-4}$alkyl)$_2$, N($C_{1-4}$alkyl)$_3^+$, $SO_2$($C_{1-4}$alkyl), C(=O)($C_{1-4}$alkylene)$NH_2$, C(=O)($C_{1-4}$alkylene)NH(alkyl), and/or C(=O)($C_{1-4}$alkylene)N($C_{1-4}$alkyl)$_2$.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

In compounds of formula (I), preferred heteroaryl groups include

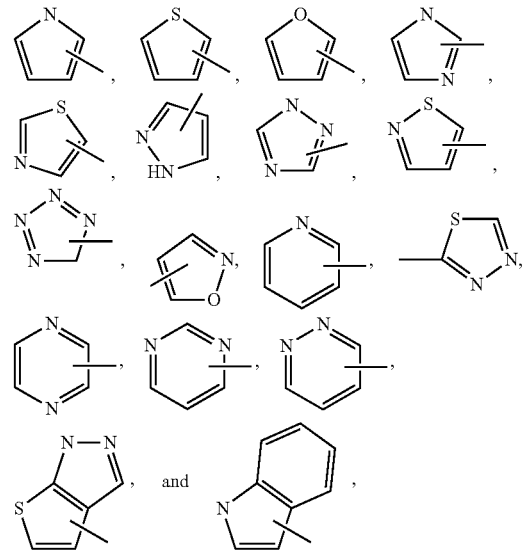

and the like, which optionally may be substituted at any available carbon or nitrogen atom.

Unless otherwise indicated, when reference is made to a specifically-named aryl (e.g., phenyl), cycloalkyl (e.g., cyclohexyl), heterocyclo (e.g., pyrrolidinyl) or heteroaryl (e.g., imidazolyl), unless otherwise specifically indicated the reference is intended to include rings having 0 to 3, preferably 0-2, substituents selected from those recited above for the aryl, cycloalkyl, heterocyclo and/or heteroaryl groups, as appropriate.

The term "heteroatoms" shall include oxygen, sulfur and nitrogen.

The term "carbocyclic" means a saturated or unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Throughout the specification, groups and substituents thereof may be chosen by one skilled in the field to provide stable moieties and compounds and compounds useful as pharmaceutically-acceptable compounds and/or intermediate compounds useful in making pharmaceutically-acceptable compounds.

The term "prodrug" denotes a compound which, upon administration to a subject, undergoes chemical conversion by metabolic or chemical processes to yield a compound of the formula (I), and/or a salt and/or solvate thereof. For example, compounds containing a carboxy group can form physiologically hydrolyzable esters which serve as prodrugs by being hydrolyzed in the body to yield formula (I) compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula (I) include $C_{1-6}$alkylbenzyl, 4-methoxybenzyl, indanyl, phthalyl, methoxymethyl, $C_{1-6}$alkanoyloxy-$C_{1-6}$alkyl, e.g. acetoxymethyl, pivaloyloxymethyl or propionyloxymethyl, $C_{1-6}$alkoxycarbonyloxy-$C_{1-6}$alkyl, e.g. methoxycarbonyl-oxymethyl or ethoxycarbonyloxymethyl, glycyloxymethyl, phenylglycyloxymethyl, (5-methyl-2-oxo-1,3-dioxolen-4-yl)-methyl and other well known physiologically hydrolyzable esters used, for example, in the penicillin and cephalosporin arts. Such esters may be prepared by conventional techniques known in the art.

Prodrug ester examples include the following groups: (1-alkanoyloxy)alkyl such as,

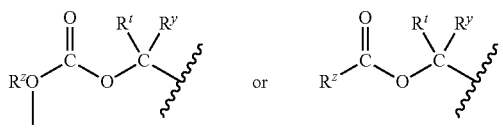

wherein $R^z$, $R^t$ and $R^y$ are H, alkyl, aryl or arylalkyl; however, $R^zO$ cannot be HO.

Examples of such prodrug esters include:

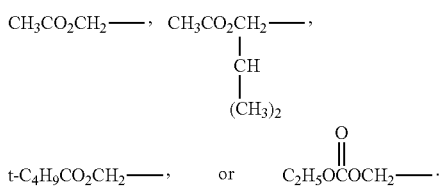

Other examples of suitable prodrug esters include

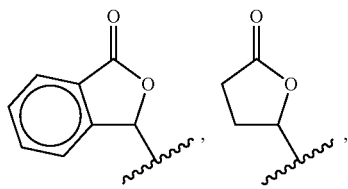

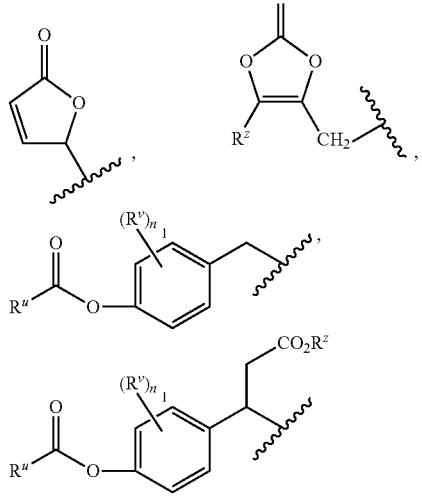

wherein $R^z$ can be H, alkyl (such as methyl or t-butyl), arylalkyl (such as benzyl) or aryl (such as phenyl); $R^v$ is H, alkyl, halogen or alkoxy, $R^u$ is alkyl, aryl, arylalkyl or alkoxyl, and $n_1$ is 0, 1 or 2.

For further examples of prodrug derivatives, see:

a) *Design of Prodrugs*, edited by H. Bundgaard, (Elsevier, 1985) and *Methods in Enzymology*, 112:309-396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, pp. 113-191 (1991); and c) H. Bundgaard, *Advanced Drug Delivery Reviews*, 8:1-38 (1992).

The term "tautomer" refers to compounds of the formula (I) and salts thereof that may exist in their tautomeric form, in which hydrogen atoms are transposed to other parts of the molecules and the chemical bonds between the atoms of the molecules are consequently rearranged. It should be understood that the all tautomeric forms, insofar as they may exist, are included within the invention.

The terms pharmaceutically acceptable "salt" and "salts" refer to basic salts formed with inorganic and organic bases. Such salts include ammonium salts; alkali metal salts, such as lithium, sodium and potassium salts (which are preferred); alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Nontoxic, pharmaceutically acceptable salts are preferred, although other salts are also useful, e.g., in isolating or purifying the product.

The term pharmaceutically acceptable "salt" and "salts" also includes acid addition salts. These are formed, for example, with strong inorganic acids, such as mineral acids, for example sulfuric acid, phosphoric acid or a hydrohalic acid such as HCl or HBr, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_{1-4}$) alkyl or arylsulfonic acids which are unsubstituted or substituted, for example by halogen, for example methanesulfonic acid or p-toluenesulfonic acid.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of Formula (I) can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

The inventive compounds may be in the free or solvate (e.g. hydrate) form.

COMBINATIONS

Where desired, the compounds of Formula (I) may be used in combination with one or more other types of therapeutic agents such as immunosuppressants, anticancer agents, anti-viral agents, anti-inflammatory agents, anti-fungal agents, antibiotics, anti-vascular hyperproliferation agents, anti-depressive agents, hypolipidemic agents or lipid-lowering agents or lipid modulating agents, antidiabetic agents, anti-obesity agents, antihypertensive agents, platelet aggregation inhibitors, and/or anti-osteoporosis agents, which may be administered orally in the same dosage form, in a separate oral dosage form or by injection.

The immunosuppressants which may be optionally employed in combination with compounds of Formula (I) of the invention include cyclosporins, for example cyclosporin A, mycophenolate, interferon-beta, deoxyspergolin, FK-506 or Ant.-IL-2.

The anti-cancer agents which may be optionally employed in combination with compounds of Formula (I) of the invention include azathiprine, 5-fluorouracil, cyclophosphamide, cisplatin, methotrexate, thiotepa, carboplatin, and the like.

The anti-viral agents which may be optionally employed in combination with compounds of Formula (I) of the invention include abacavir, aciclovir, ganciclovir, zidanocin, vidarabine, and the like.

The anti-inflammatory agents which may be optionally employed in combination with compounds of Formula (I) of the invention include non-steroidal anti-inflammatory drugs (NSAIDs) such as ibuprofen, cox-2 inhibitors such as celecoxib, rofecoxib, aspirin, naproxen, ketoprofen, diclofenac sodium, indomethacin, piroxicam, steroids such as prednisone, dexamethasone, hydrocortisone, triamcinolone diacetate, gold compounds, such as gold sodium thiomalate, TNF-α inhibitors such as tenidap, anti-TNF antibodies or soluble TNF receptor, and rapamycin (sirolimus or Rapamune) or derivatives thereof, infliximab (Remicade® Centocor, Inc.). CTLA-4Ig, LEA29Y, antibodies such as anti-ICAM-3, anti-IL-2 receptor (Anti-Tac), anti-CD45RB, anti-CD2, anti-CD3 (OKT-3), anti-CD4, anti-CD80, anti-CD86, monoclonal antibody OKT3, agents blocking the interaction between CD40 and CD154 (a.k.a. "gp39"), such as antibodies specific for CD40 and/or CD154, fusion proteins such as etanercept, fusion proteins constructed from CD40 and/or CD154gp39 (e.g. CD40Ig and CD8gp39), inhibitors, such as nuclear translocation inhibitors, of NF-κB function, such as deoxyspergualin (DSG).

The anti-fungal agents which may be optionally employed in combination with compounds of Formula (I)I of the invention include fluconazole, miconazole, amphotericin B, and the like.

The antibiotics which may be optionally employed in combination with compounds of Formula (I) of the invention include penicillin, tetracycline, amoxicillin, ampicillin, erythromycin, doxycycline, vancomycin, minocycline, clindamycin, or cefalexin.

The anti-vascular hyperproliferation agents which may be optionally employed with compounds of Formula (I) of the invention include methotrexate, leflunomide, FK506 (tacrolimus, Prograf), The hypolipidemic agent or lipid-lowering agent or lipid modulating agents which may be optionally employed in combination with the compounds of Formula (I) of the invention may include 1, 2, 3 or more MTP inhibitors, HMG CoA reductase inhibitors, squalene synthetase inhibitors, fabric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-trifluoroethoxy)benzoyl]amino]-1-piperidinyl]butyl]-N-(2,2,2-trifluoroethyl)-9H-fluorene-9-carboxamide

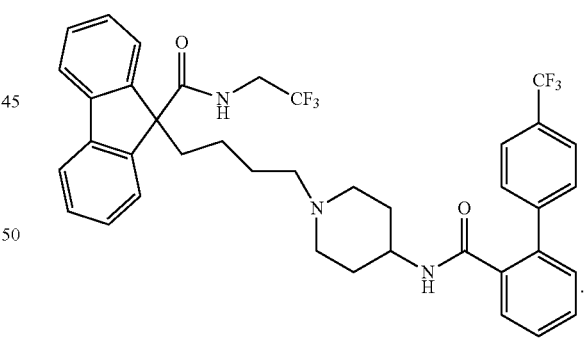

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, itavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 642-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al., *J. Med. Chem.*, 31(10):1869-1871 (1988), including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., *Current Pharmaceutical Design*, 2:1-40 (1996).

In addition, other squalene synthetase inhibitors suitable for use herein include the terpenoid pyrophosphates disclosed by P. Ortiz de Montellano et al., *J. Med. Chem.*, 20:243-249 (1977), the farnesyl diphosphate analog A and presqualene pyrophosphate (PSQ-PP) analogs as disclosed by Corey and Volante, *J. Am. Chem. Soc.*, 98:1291-1293 (1976), phosphinylphosphonates reported by McClard, R. W. et al., *J. Am. Chem. Soc.*, 109:5544 (1987), and cyclopropanes reported by Capson, T. L., PhD dissertation, Dept. Med. Chem. U. of Utah, Abstract, Table of Contents, pp. 16, 17, 40-43, 48-51, Summary (June 1987).

Other hypolipidemic agents suitable for use herein include, but are not limited to, fabric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The hypolipidemic agent may be an ACAT inhibitor such as disclosed in, *Drugs of the Future*, 24:9-15 (1999) (Avasimibe); Nicolosi et al., "The ACAT inhibitor, Cl-1011 is effective in the prevention and regression of aortic fatty streak area in hamsters", *Atherosclerosis* (Shannon, Irel.), 137(1): 77-85 (1998), Ghiselli, Giancarlo, "The pharmacological profile of FCE 27677: a novel ACAT inhibitor with potent hypolipidemic activity mediated by selective suppression of the hepatic secretion of ApoB100-containing lipoprotein", *Cardiovasc. Drug Rev.*, 16(1):16-30 (1998); Smith, C., et al., "RP 73163: a bioavailable alkylsulfinyl-diphenylimidazole ACAT inhibitor", *Bioorg. Med. Chem. Lett.*, 6(1):47-50 (1996); Krause et al, "ACAT inhibitors: physiologic mechanisms for hypolipidemic and anti-atherosclerotic activities in experimental animals", *Inflammation: Mediators Pathways*, CRC, Boca Raton, Fla., publ., Ruffolo, Robert R., Jr., Hollinger, Mannfred A., eds., pp. 173-198 (1995); Sliskovic et al., "ACAT inhibitors: potential anti-atherosclerotic agents", *Curr. Med. Chem.*, 1(3):204-25 (1994)); Stout et al., "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", *Chemtracts: Org. Chem.*, 8(6):359-362 (1995), or TS-962 (acetamide, N-[2,6-bis(1-methylethyl) phenyl]-2-(tetradecylthio)-) (Taisho Pharmaceutical Co. Ltd).

The hypolipidemic agent may be an upregulator of LD2 receptor activity such as MD-700 (1(3H)-isobenzofuranone, 3-(13-hydroxy-10-oxotetradecyl)-5,7-dimethoxy) (Taisho Pharmaceutical Co. Ltd) and LY295427 (cholestan-3-ol, 4-(2-propenyl)-, (3a, 4a, 5a)-) (Eli Lilly).

The hypolipidemic agent may be a cholesterol absorption inhibitor preferably Schering-Plough's ezetimibe (SCH58235) and SCH48461 as well as those disclosed in *Atherosclerosis*, 115:45-63 (1995) and *J. Med. Chem.*, 41:973 (1998).

The hypolipidemic agent may be an ileal Na$^+$/bile acid cotransporter inhibitor such as disclosed in *Drugs of the Future*, 24:425-430 (1999).

The lipid-modulating agent may be a cholesteryl ester transfer protein (CETP) inhibitor such as Pfizer's CP 529,414 (torcetrapib) (WO 00/38722 and EP 818448) and Pharmacia's SC-744 and SC-795.

The ATP citrate lyase inhibitor which may be employed in the combination of the invention may include, for example, those disclosed in U.S. Pat. No. 5,447,954.

Preferred hypolipidemic agents are pravastatin, lovastatin, simvastatin, atorvastatin, fluvastatin, cerivastatin, itavastatin and visastatin and ZD-4522.

The above-mentioned U.S. patents are incorporated herein by reference. The amounts and dosages employed will be as indicated in the Physicians' Desk Reference and/or in the patents set out above.

The compounds of Formula (I) of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an
HMG CoA reductase inhibitor, for example, pravastatin, lovastatin, simvastatin, atorvastatin, fluvastatin or cerivastatin in dosages employed as indicated in the Physicians' Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 0.5 to about 80 mg, and more preferably from about 1 to about 40 mg.

A preferred oral dosage form, such as tablets or capsules will contain the squalene synthetase inhibitor in an amount of from about 10 to about 500 mg, preferably from about 25 to about 200 mg.

The hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al., "Attenuation of diet-induced atherosclerosis in rabbits with a highly selective 15-lipoxygenase inhibitor lacking significant antioxidant properties", *Brit. J. Pharmacology*, 120:1199-1206 (1997), and Cornicelli et al., "15-Lipoxygenase and its Inhibition: A Novel Therapeutic Target for Vascular Disease", *Current Pharmaceutical Design*, 5:11-20 (1999).

The compounds of Formula (I) and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin as well as niacin and/or cholestagel.

The other antidiabetic agent which may be optionally employed in combination with the compound of Formula (I) may be 1, 2, 3 or more antidiabetic agents or antihyperglycemic agents including insulin secretagogues or insulin sensitizers, or other antidiabetic agents preferably having a mechanism of action different from the compounds of Formula (I) of the invention, which may include biguanides, sulfonyl ureas, glucosidase inhibitors, PPAR γ agonists, such as thiazolidinediones, aP2 inhibitors, dipeptidyl peptidase IV (DP4) inhibitors, SGLT2 inhibitors, and/or meglitinides, as well as insulin, and/or glucagon-like peptide-1 (GLP-1).

The other antidiabetic agent may be an oral antihyperglycemic agent preferably a biguanide such as metformin or phenformin or salts thereof, preferably metformin HCl.

Where the antidiabetic agent is a biguanide, the compounds of Formula (I) will be employed in a weight ratio to biguanide within the range from about 0.001:1 to about 10:1, preferably from about 0.01:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of Formula (I) will be employed in a weight ratio to the sulfonyl urea in the range from about 0.01:1 to about 100:1, preferably from about 0.02:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of Formula (I) will be employed in a weight ratio to the glucosidase inhibitor within the range from about 0.01:1 to about 100:1, preferably from about 0.05:1 to about 10:1.

The compounds of Formula (I) may be employed in combination with a PPAR γ agonist such as a thiazolidinedione oral antidiabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570 (farglitazar), englitazone (CP-68722, Pfizer) or darglitazone (CP-86325, Pfizer, isaglitazone (MIT/J&J), JTT-501 (reglitazar) (JPNT/P&U), L-895645 (Merck), R-119702 (rivoglitazone) (Sankyo/WL), N,N-2344 (balaglitazone) (Dr. Reddy/NN), or YM-440 ((Z)-1,4-bis-4-[(3,5-dioxo-1,2,4-oxadiazolidin-2-yl-methyl)]-phenoxybut-2-ene) (Yamanouchi), preferably rosiglitazone and pioglitazone.

The compounds of Formula (I) will be employed in a weight ratio to the thiazolidinedione in an amount within the range from about 0.01:1 to about 100:1, preferably from about 0.05 to about 10:1.

The sulfonyl urea and thiazolidinedione in amounts of less than about 150 mg oral antidiabetic agent may be incorporated in a single tablet with the compounds of Formula (I).

The compounds of Formula (I) may also be employed in combination with a antihyperglycemic agent such as insulin or with glucagon-like peptide-1 (GLP-1) such as GLP-1(1-36) amide, GLP-1(7-36) amide, GLP-1(7-37) (as disclosed in U.S. Pat. No. 5,614,492 to Habener, the disclosure of which is incorporated herein by reference), as well as AC2993 (exenatide) (Amylin) and LY-315902 (8-37-glucagon-like peptide I (human), N-[3-(1H-imidazol-4-yl)-1-oxopropyl]-26-L-arginine-34-[N6-(1-oxooctyl)-L-lysine]-) (Lilly), which may be administered via injection, intranasal, inhalation or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physicians' Desk Reference (PDR).

Where present, metformin or salt thereof may be employed in amounts within the range from about 500 to about 2000 mg per day which may be administered in single or divided doses one to four times daily.

Where present, the thiazolidinedione antidiabetic agent may be employed in amounts within the range from about 0.01 to about 2000 mg/day which may be administered in single or divided doses one to four times per day.

Where present insulin may be employed in formulations, amounts and dosing as indicated by the Physicians' Desk Reference.

Where present GLP-1 peptides may be administered in oral buccal formulations, by nasal administration or parenterally as described in U.S. Pat. Nos. 5,346,701 (TheraTech), 5,614, 492 and 5,631,224 which are incorporated herein by reference.

The other antidiabetic agent may also be a PPAR α/γ dual agonist such as AR-HO39242 (tesaglitazar) (Astra/Zeneca), GW-409544 (Glaxo-Wellcome), KRP297 (benzamide, 5-[(2, 4-dioxo-5-thiazolidinyl)methyl]-2-methoxy-N-[[4-(trifluoromethyl)phenyl]methyl]- (Kyorin Merck) as well as those disclosed by Murakami et al., "A Novel Insulin Sensitizer Acts As a Coligand for Peroxisome Proliferation-Activated Receptor Alpha (PPAR alpha) and PPAR gamma Effect on PPAR alpha Activation on Abnormal Lipid Metabolism in Liver of Zucker Fatty Rats", Diabetes, 47:1841-1847 (1998).

The antidiabetic agent may be an SGLT2 inhibitor such as disclosed in U.S. application Ser. No. 09/679,027, filed Oct. 4, 2000, employing dosages as set out therein. Preferred are the compounds designated as preferred in the above application.

The antidiabetic agent may be an aP2 inhibitor such as disclosed in U.S. application Ser. No. 09/391,053, filed Sep. 7, 1999, and in U.S. application Ser. No. 09/519,079, filed Mar. 6, 2000, employing dosages as set out herein. Preferred are the compounds designated as preferred in the above application.

The antidiabetic agent may be a DP4 inhibitor such as disclosed in U.S. application Ser. No. 09/788,173 filed Feb. 16, 2001, WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al., Biochemistry, 38(36):11597-11603 (1999), TSL-225 (tryptophyl-1,2,3,4-tetrahydro-isoquinoline-3-carboxylic acid (disclosed by Yamada et al., Bioorg. & Med. Chem. Lett., 8:1537-1540 (1998), 2-cyanopyrrolidides and 4-cyanopyrrolidides as disclosed by Ashworth et al., Bioorg. & Med. Chem. Lett., 6(22):1163-1166 and 2745-2748 (1996) employing dosages as set out in the above references.

The meglitinide which may optionally be employed in combination with the compound of Formula (I) of the invention may be repaglinide, nateglinide (Novartis) or KAD1229 (mitiglinide) (PF/Kissei), with repaglinide being preferred.

The compound of Formula (I) will be employed in a weight ratio to the meglitinide, PPAR γ agonist, PPAR α/γ dual agonist, aP2 inhibitor, DP4 inhibitor or SGLT2 inhibitor within the range from about 0.01:1 to about 100:1, preferably from about 0.05 to about 10:1.

The other type of therapeutic agent which may be optionally employed with a compound of Formula (I) may be 1, 2, 3 or more of an anti-obesity agent including a beta 3 adrenergic agonist, a lipase inhibitor, a serotonin (and dopamine) reuptake inhibitor, an aP2 inhibitor, a thyroid receptor agonist and/or an anorectic agent.

The beta 3 adrenergic agonist which may be optionally employed in combination with a compound of Formula (I) may be AJ9677 (rafabegron) (Takeda/Dainippon), L750355 (benezenesulfonamide, N-[4-[2-[[(2S)-3-[(6-amino-3-pyridinyl)oxy]-2-hydroxypropyl]amino]ethyl]phenyl]-4-(1-methylethyl)-) (Merck), or CP331684 (4-[2-[[2-(6-aminopyridin-3-yl)-2(R)-hydroxyethyl]-amino]ethoxy]phenyl]acetic acid) (Pfizer) or other known beta 3 agonists as disclosed in U.S. Pat. Nos. 5,541,204, 5,770,615, 5,491,134, 5,776,983 and 5,488,064, with AJ9677, L750,355 (benzenesulfonamide, N-[4-[2-[[(2S)-3-[(6-amino-3-pyridinyl)oxy]-2-hydroxypropyl]amino]ethyl]phenyl]-4-(1-methylethyl)-) and CP331684 being preferred.

The lipase inhibitor which may be optionally employed in combination with a compound of Formula (I) may be orlistat or ATL-962 (Alizyme), with orlistat being preferred.

The serotonin (and dopamine) reuptake inhibitor which may be optionally employed in combination with a compound of Formula (I) may be sibutramine, topiramate (Johnson & Johnson) or axokine (Regeneron), with sibutramine and topiramate being preferred.

The thyroid receptor agonist which may be optionally employed in combination with a compound of Formula (I) may be a thyroid receptor ligand as disclosed in WO97/21993 (U. Cal SF), WO99/00353 (KaroBio), WO00/039077 (KaroBio), and U.S. Provisional Application 60/183,223 filed Feb. 17, 2000, with compounds of the KaroBio applications and the above U.S. provisional application being preferred.

The anorectic agent which may be optionally employed in combination with a compound of Formula (I) may be dexamphetamine, phentermine, phenylpropanolamine or mazindol, with dexamphetamine being preferred.

The various anti-obesity agents described above may be employed in the same dosage form with the compound of Formula (I) or in different dosage forms, in dosages and regimens as generally known in the art or in the PDR.

The antihypertensive agents which may be employed in combination with the compound of Formula (I) of the invention include ACE inhibitors, angiotensin II receptor antagonists, NEP/ACE inhibitors, as well as calcium channel blockers, β-adrenergic blockers and other types of antihypertensive agents including diuretics.

The angiotensin converting enzyme inhibitor which may be employed herein includes those containing a mercapto (—S—) moiety such as substituted proline derivatives, such as any of those disclosed in U.S. Pat. No. 4,046,889 to Ondetti et al mentioned above, with captopril, that is, 1-[(2S)-3-mercapto-2-methylpropionyl]-L-proline, being preferred, and mercaptoacyl derivatives of substituted prolines such as any of those disclosed in U.S. Pat. No. 4,316,906 with zofenopril being preferred.

Other examples of mercapto containing ACE inhibitors that may be employed herein include rentiapril (fentiapril, Santen) disclosed in Clin. Exp. Pharmacol. Physiol., 10:131 (1983); as well as pivopril and YS980.

Other examples of angiotensin converting enzyme inhibitors which may be employed herein include any of those disclosed in U.S. Pat. No. 4,374,829 mentioned above, with N-(1-ethoxycarbonyl-3-phenylpropyl)-L-alanyl-L-proline, that is, enalapril, being preferred, any of the phosphonate substituted amino or imino acids or salts disclosed in U.S. Pat. No. 4,452,790 with (S)-1-[6-amino-2-[[hydroxy-(4-phenylbutyl)phosphinyl]oxy]-1-oxohexyl]-L-proline or (ceronapril) being preferred, phosphinylalkanoyl prolines disclosed in U.S. Pat. No. 4,168,267 mentioned above with fosinopril being preferred, any of the phosphinylalkanoyl substituted prolines disclosed in U.S. Pat. No. 4,337,201, and the phosphonamidates disclosed in U.S. Pat. No. 4,432,971 discussed above.

Other examples of ACE inhibitors that may be employed herein include Beecham's BRL 36,378 as disclosed in European Patent Application Nos. 80822 and 60668; Chugai's MC-838 disclosed in C.A. 102:72588v and *Jap. J. Pharmacol.* 40:373 (1986); Ciba-Geigy's CGS 14824 (3-([1-ethoxy-carbonyl-3-phenyl-(1S)-propyl]amino)-2,3,4,5-tetrahydro-2-oxo-1-(3S)-benzazepine-1 acetic acid HCl) disclosed in U.K. Patent No. 2103614 and CGS 16,617 (3(S)-[[(1S)-5-amino-1-carboxypentyl]amino]-2,3,4,5-tetrahydro-2-oxo-1H-1-benzazepine-1-ethanoic acid) disclosed in U.S. Pat. No. 4,473,575; cetapril (alacepril, Dainippon) disclosed in *Eur. Therap. Res.*, 39:671 (1986), 40:543 (1986); ramipril (Hoechst) disclosed in Euro. Patent No. 79-022 and *Curr. Ther. Res.*, 40:74 (1986); Ru 44570 (Hoechst) disclosed in *Arzneimiuelforschung*, 34:1254 (1985), cilazapril (Hoffman-LaRoche) disclosed in *J. Cardiovasc. Pharmacol.*, 9:39 (1987); R 31-2201 (Hoffman-LaRoche) disclosed in *FEBS Lett.*, 165:201 (1984); lisinopril (Merck), indalapril (delapril) disclosed in U.S. Pat. No. 4,385,051; indolapril (Schering) disclosed in *J. Cardiovasc. Pharmacol.*, 5:643, 655 (1983), spirapril (Schering) disclosed in *Acta. Pharmacol. Toxicol.*, 59(Supp. 5):173 (1986); perindopril (Servier) disclosed in *Eur. J. Clin. Pharmacol.*, 31:519 (1987); quinapril (Warner-Lambert) disclosed in U.S. Pat. No. 4,344,949 and C1925 (Warner-Lambert) ([3S-[2[R(*)R(*)]]3R(*)]-2-[2-[[1-(ethoxy-carbonyl)-3-phenylpropyl]amino]-1-oxopropyl]-1, 2,3,4-tetrahydro-6,7-dimethoxy-3-isoquinolinecarboxylic acid HCl) disclosed in *Pharmacologist*, 26:243, 266 (1984), WY-44221 (Wyeth) disclosed in *J. Med. Chem.*, 26:394 (1983).

Preferred ACE inhibitors are captopril, fosinopril, enalapril, lisinopril, quinapril, benazepril, fentiapril, ramipril and moexipril.

NEP/ACE inhibitors may also be employed herein in that they possess neutral endopeptidase (NEP) inhibitory activity and angiotensin converting enzyme (ACE) inhibitory activity. Examples of NEP/ACE inhibitors suitable for use herein include those disclosed in U.S. Pat. Nos. 5,362,727, 5,366,973, 5,225,401, 4,722,810, 5,223,516, 4,749,688, U.S. Pat. No. 5,552,397, U.S. Pat. No. 5,504,080, U.S. Pat. No. 5,612,359, U.S. Pat. No. 5,525,723, European Patent Application 0599444, 0481522, 0599444, 0595610, European Patent Application 0534363A2, 534396 and 534492, and European Patent Application 0629627A2.

Preferred are those NEP/ACE inhibitors and dosages thereof which are designated as preferred in the above patents/applications which U.S. patents are incorporated herein by reference; most preferred are omapatrilat ([S—(R*,R*)]-hexahydro-6-[(2-mercapto-1-oxo-3-phenylpropyl)amino]-2, 2-dimethyl-7-oxo-1H-azepine-1-acetic acid (gemopatrilat)) and CGS 30440.

The angiotensin II receptor antagonist (also referred to herein as angiotensin II antagonist or AII antagonist) suitable for use herein includes, but is not limited to, irbesartan, losartan, valsartan, candesartan, telmisartan, tasosartan or eprosartan, with irbesartan, losartan or valsartan being preferred.

A preferred oral dosage form, such as tablets or capsules, will contain the ACE inhibitor or AII antagonist in an amount within the range from abut 0.1 to about 500 mg, preferably from about 5 to about 200 mg and more preferably from about 10 to about 150 mg.

For parenteral administration, the ACE inhibitor, angiotensin II antagonist or NEP/ACE inhibitor will be employed in an amount within the range from about 0.005 mg/kg to about 10 mg/kg and preferably from about 0.01 mg/kg to about 1 mg/kg.

Where a drug is to be administered intravenously, it will be formulated in conventional vehicles, such as distilled water, saline, Ringer's solution or other conventional carriers.

It will be appreciated that preferred dosages of ACE inhibitor and AII antagonist as well as other antihypertensives disclosed herein will be as set out in the latest edition of the Physicians' Desk Reference (PDR).

Other examples of preferred antihypertensive agents suitable for use herein include omapatrilat (Vanlev®) amlodipine besylate (Norvasc®), prazosin HCl (Minipress®), verapamil, nifedipine, nadolol, diltiazem, felodipine, nisoldipine, isradipine, nicardipine, atenolol, carvedilol, sotalol, terazosin, doxazosin, propranolol, and clonidine HCl (Catapres®).

Diuretics which may be employed in combination with compounds of Formula (I) include hydrochlorothiazide, torasemide, furosemide, spironolactono, and indapamide.

Antiplatelet agents which may be employed in combination with compounds of Formula (I) of the invention include aspirin, clopidogrel, ticlopidine, dipyridamole, abciximab, tirofiban, eptifibatide, anagrelide, and ifetroban, with clopidogrel and aspirin being preferred.

The antiplatelet drugs may be employed in amounts as indicated in the PDR. Ifetroban may be employed in amounts as set out in U.S. Pat. No. 5,100,889.

Antiosteoporosis agents suitable for use herein in combination with the compounds of Formula (I) of the invention include parathyroid hormone or bisphosphonates, such as MK-217 (alendronate) (Fosamax®).

Dosages employed for the above drugs will be as set out in the Physicians' Desk Reference.

PHARMACEUTICAL FORMULATIONS

The pharmaceutical composition of the invention includes a pharmaceutically acceptable carrier, adjuvant or vehicle that may be administered to a subject, together with a compound of the present invention, and which does not destroy the pharmacological activity thereof. Pharmaceutically acceptable carriers, adjuvants and vehicles that may be used in the pharmaceutical compositions of the present invention include, but are not limited to, the following: ion exchangers, alumina, aluminum stearate, lecithin, self-emulsifying drug delivery systems ("SEDDS") such as d(-tocopherol polyethyleneglycol 1000 succinate), surfactants used in pharmaceutical dosage forms such as Tweens or other similar polymeric delivery matrices, serum proteins such as human serum albumin, buffer substances such as phosphates, glycine, sorbic acid, potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β- and γ-cyclodextrin, or chemically modified derivatives such as hydroxyalkylcyclodextrins, including 2- and 3-hydroxypropyl-β-cyclodextrins, or other solubilized derivatives may also be used to enhance delivery of the modulators of the present invention.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the invention may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The compounds of the invention may, for example, be administered in a form suitable for immediate release or extended release. Immediate release or extended release may be achieved by the use of suitable pharmaceutical compositions including the compounds of the invention, or, particularly in the case of extended release, by the use of devices such as subcutaneous implants or osmotic pumps. The compounds of the invention may also be administered liposomally.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The present compounds may also be delivered through the oral cavity by sublingual and/or buccal administration. Molded tablets, compressed tablets or freeze-dried tablets are exemplary forms which may be used. Exemplary compositions include those formulating the compound(s) of the invention with fast dissolving diluents such as mannitol, lactose, sucrose and/or cyclodextrins. Also included in such formulations may be high molecular weight excipients such as celluloses (Avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

Exemplary compositions for rectal administration include suppositories which may contain, for example, a suitable non-irritating excipient, such as cocoa butter, synthetic glyceride esters or polyethylene glycols, which are solid at ordinary temperatures, but liquefy and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.1 to 500 mg/kg of body weight of active compound per day, or between 5 and 2000 mg per day which may be administered in a single dose or in the form of individual divided doses, such as from 1 to 5 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like.

A typical capsule for oral administration contains compounds of Formula (I) (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of Formula (I) into a vial, aseptically freeze-drying and sealing. For use, the contents of the vial are mixed with 2 mL of physiological saline, to produce an injectable preparation.

The compounds of the examples are inhibitors of AP-1 activity and/or compete with known ligands of the glucorcorticoid receptor.

Identical and/or similar assays are described in U.U. Patent Application Publication 2006/0223110 A1, filed Jul. 18, 2002 which is incorporated in its entirety herein by reference.

ASSAYS

GR Binding Assays
Glucocorticoid Receptor Binding Assay (I)

In order to assess the affinity of test compounds for the human glucocorticoid receptor, a commercially available kit was used (Glucocorticoid Receptor Competitor Assay Kit, Invitrogen Part #2893). Briefly, purified human recombinant full-length glucocorticoid receptor (2 nM) was mixed with fluorescently labeled glucocorticoid (1 nM Fluormone GS Red) in the presence or absence of test compound. After two hours incubation at room temperature in the dark, the fluorescence polarization (FP) of the sample was measured. The FP of a mixture of receptor, fluorescent probe (i.e. Fluormone GS Red) and 5 µM dexamethasone represented background fluorescence or 100% inhibition, whereas, the FP of the mixture without dexamethasone (but in the presence of vehicle) was taken to be 100% binding. The percentage inhibition of test compounds was then compared to the sample with 5 µM dexamethasone and expressed as % relative binding activity with dexamethasone being 100% and no inhibition is 0%. Test compounds were analyzed in the concentration range from 8.5E-05 µM to 5 µM.

Glucocorticoid Receptor Binding Assay (II)

In order to measure the binding of compounds on the glucocorticoid receptor, a commercially available kit was used (Glucocorticoid receptor competitor assay kit, PanVera Co., Madison, Wis., P2816). Briefly, a cell lysate containing recombinantly expressed human full-length glucocorticoid receptor was mixed with a fluorescently labeled glucocorticoid (1 nM Fluormone GS1) in the presence or absence of the test compound. After one hour at room temperature, the fluorescence polarization (FP) of the sample was measured. The FP of a mixture of receptor, fluorescent probe (i.e. Fluormone GS1) and 1 mM dexamethasone represented background fluorescence or 100% inhibition, whereas, the FP of the mixture without dexamethasone was taken to be 100% binding. The percentage inhibition of test molecules were then compared to the sample with 1 mM dexamethasone and expressed as % relative binding activity with dexamethasone being 100% and no inhibition is 0%. Test molecules were analyzed in the concentration range from 2.4 nM to 40 microMolar.

Cellular Transrepressional Assay

To measure the ability of test molecules to inhibit AP-1 induced transcriptional activity we utilized an A549 cell which was stably transfected with a plasmid containing 7×AP-1 DNA binding sites (pAP-1-Luc plasmid, Stratagene Co. La Jolla, Calif.) followed by the gene for luciferase. Cells were activated with 10 ng/ml of phorbol myristic acid (PMA) plus or minus test molecules for 7 hours. After 7 hours a luciferase reagent was added to measure luciferase enzymatic activity in the cell. After a 10 minute incubation of luciferase reagent with cells, luminescence was measured in a TopCount luminescence counter. Repression of AP-1 activity was calculated as the percentage decrease in the signal induced by PMA alone. Test molecules were analyzed in the concentration range from 0.1 nM to 40 µM. $EC_{50}$ values were determined by using standard curve fitting methods such as Excel fit (Microsoft Co.). An $EC_{50}$ value is the test molecule concentration at which there is a 50% repression of the maximal inhibition of transcription, i.e. a 50% reduction of AP-1 activity. In the absence of an $EC_{50}$ value, the maximum % inhibition recorded is the inhibition of AP-1 at a compound concentration of 10 micromolar.

Other reporters and cell lines also may be used in a cellular transrepressional assay. A similar assay is performed in which NF-κB activity is measured. A plasmid containing NF-κB DNA binding sites is used, such as pNF-kB-Luc, (Stratagene, LaJolla Calif.), and PMA or another stimulus, such as TNF-α or lipopolysaccharide, is used to activate the NF-κB pathway. NF-κB assays similar to that described in Yamamoto K. et al., *J. Biol. Chem.*, 270(52):31315-31320 (Dec. 29, 1995) may be used.

The cellular transrepressional assays described above may be used to measure transrepression by any NHR. One of skill in the art will understand that assays may require the addition of components, such as a stimulus (e.g. PMA, lipopolysaccharide, TNF-α, etc) which will induce transcription mediated by AP-1 or NF-κB.

Additionally, AR mediated transrepression may be measured by the assay described in Palvimo. J. J. et al., *J. Biol. Chem.*, 271(39):24151-24156 (Sep. 27, 1996), and PR mediated transrepression may be measured by the assay described in Kalkhoven, E. et al., *J. Biol. Chem.*, 271(11):6217-6224 (Mar. 15, 1996).

ABBREVIATIONS

The following abbreviations are employed in the following Preparations and Examples:

aq.=aqueous
Ar=argon
Bn=benzyl
BOP reagent=benzotriazol-1-yloxy-tris(dimethylamino) phosphonium hexafluorophosphate
Boc=tert-butoxycarbonyl
CAN=ceric ammonium nitrate
Cbz=carbobenzyloxy or carbobenzoxy or benzyloxycarbonyl
Cbz-Cl=benzyl chloroformate
DBU=1,8-diazabicyclo[5.4.0]undec-7-ene
DCE=1,2 dichloroethane
DEAD=diethyl azodicarboxylate
DIAD=diisopropyl azodicarboxylate
DIBALH=diisobutyl aluminum hydride
DMAP=4-dimethylaminopyridine
DME=1,2 dimethoxyethane
DMF=dimethyl formamide
DMSO=dimethyl sulfoxide
EDC (or EDC.HCl) or EDCI (or EDCI.HCl) or EDAC=3-ethyl-3'-(dimethylamino)propyl-carbodiimide hydrochloride (or 1-(3-dimethylaminopropyl)-3-ethylcarbodiimide hydrochloride)
$Et_3N$=triethylamine
Et=ethyl
$Et_2O$=diethyl ether
EtOAc=ethyl acetate
EtOH=ethanol
FMOC=fluorenylmethoxycarbonyl
g=gram(s)
h or hr=hour(s)
HMPA=hexamethyl phosphoric triamide
HOAc or AcOH=acetic acid
HOAT=1-Hydroxy-7-azabenzotriazole
HOBT or $HOBT.H_2O$=1-hydroxybenzotriazole hydrate
i-PrOH=isopropanol
i-$Pr_2$NEt=diisopropylethylamine
$K_2CO_3$=potassium carbonate
KOH=potassium hydroxide
L=liter
LAH or $LiAlH_4$=lithium aluminum hydride
LC/MS=high performance liquid chromatography/mass spectrometry
LDA=lithium diisopropylamide
LiOH=lithium hydroxide
Me=methyl
meq=milliequivalent
MeOH=methanol
mg=milligram(s)
min=minute(s)
mL=milliliterhex=hexanes
mol=moles
mmol=millimole(s)
$N_2$=nitrogen
$NaBH_4$=sodium borohydride
$NaBH(OAc)_3$=sodium triacetoxyborohydride
$NaHCO_3$=sodium bicarbonate
$NaN(TMS)_2$=sodium hexamethyldisilazide or sodium bis(t-rimethylsilyl)amide
NaOH=sodium hydroxide
n-BuLi=n-butyllithium
NMM=N-methyl morpholine
Pd/C=palladium on carbon
$Pd(OAc)_2$=Palladium acetate
Ph=phenyl
$Ph_3P$=triphenylphosphine
$(Ph_3P)_4Pd°$=tetrakis triphenylphosphine palladium PtO₂=platinum oxide
RT=room temperature
sat or sat'd=saturated
SAX=Strong Anion Exchanger
SCX=Strong Cation Exchanger
TBS=tert-butyldimethylsilyl
t-Bu=tertiary butyl
TFA=trifluoroacetic acid
TFAA=trifluoroacetic anhydride
THF=tetrahydrofuran
TLC=thin layer chromatography
TMS=trimethylsilyl
TMSN₃=trimethylsilyl azide
μL=microliter
HPLC=high performance liquid chromatography
Reverse phase HPLC=reverse phase high performance liquid chromatography, using a YMC ODS S5 column and a binary solvent A/solvent B eluents
Solvent A=10% MeOH-90% H₂O-0.1% TFA
Solvent B=90% MeOH-10% H₂O-0.1% TFA
MS or Mass Spec=mass spectrometry
NMR=nuclear magnetic resonance
NMR spectral data: s=singlet; d=doublet; m=multiplet; br=broad; t=triplet
mp=melting point

EXAMPLES

The invention will now be further described by the following working examples, which are preferred embodiments of the invention. These examples are illustrative rather than limiting. There may be other embodiments that fall within the spirit and scope of the invention as defined by the appended claims.

Example 1

(S)-1-((5aR,6S)-1-(4-Fluorophenyl)-5a-methyl-5,5a,6,7,8,9-hexahydroimidazo[1,5-b]isoquinolin-6-yl)-1-(thiophen-2-yl)ethanol

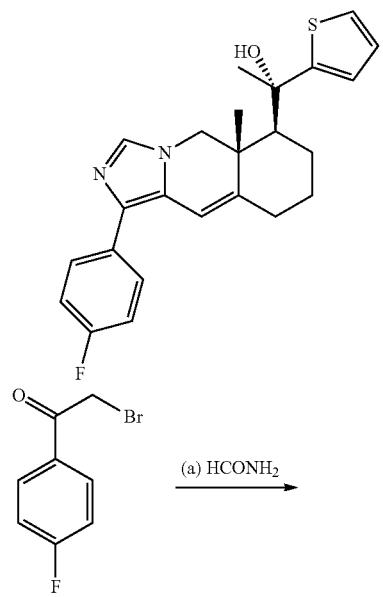

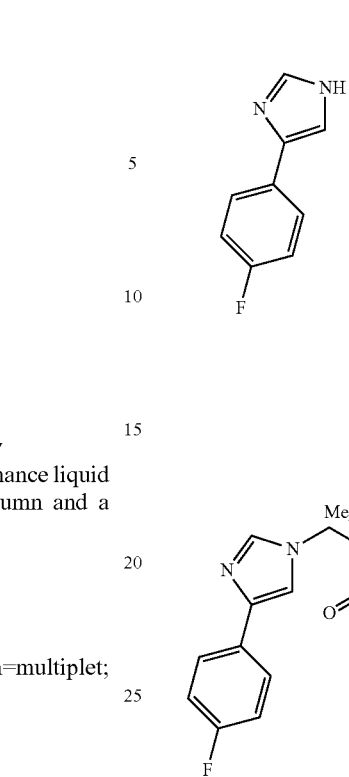

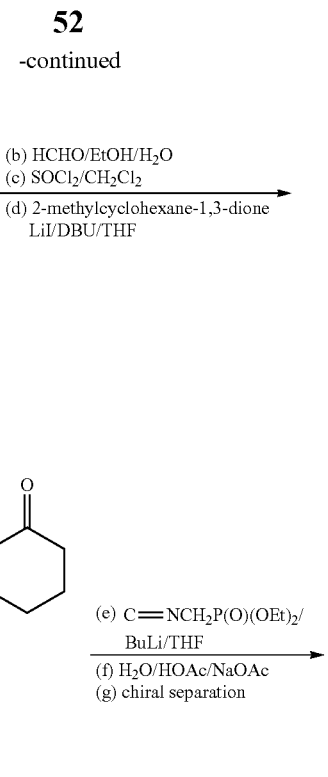

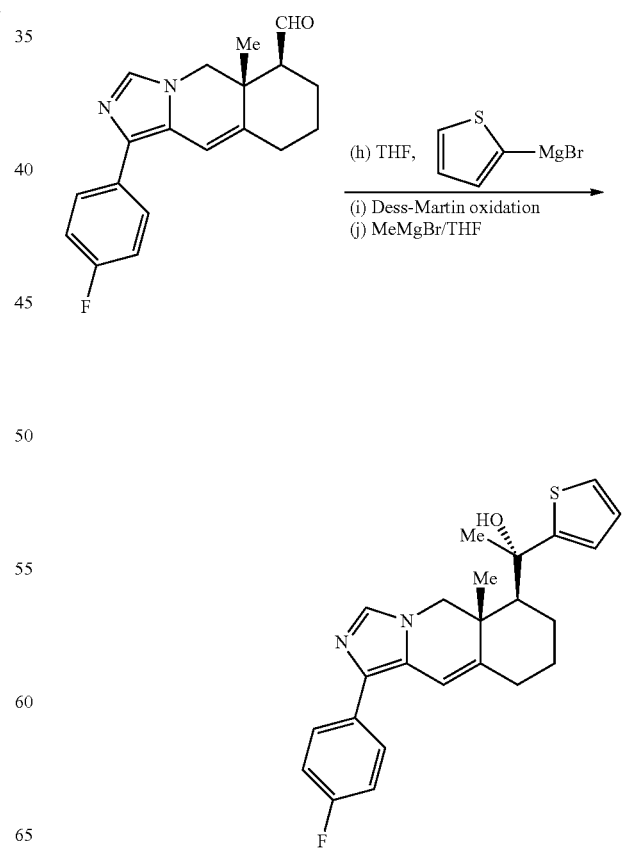

(a) A mixture of 2-bromo-1-(4-fluorophenyl)ethanone (10.9 g, 50 mmol) and formamide (14 mL, 350 mmol) was stirred at 170° C. under nitrogen for 4 hr. The reaction mixture was cooled and mixed with ethyl acetate (40 mL). Saturated aqueous sodium bicarbonate solution (50 mL) was added with caution while the mixture was cooled in an ice-water bath. The aqueous layer was separated and extracted with ethyl acetate (2×40 mL). The combined organic solutions were washed with water (30 mL) and brine (30 mL), dried ($Na_2SO_4$), and concentrated. Silica gel flash chromatography (10-100% ethyl acetate in hexanes) gave 4-(4-fluorophenyl)-1H-imidazole (3.46 g, 21 mmol, 43% yield) as a solid. MS found: $(M+H)^+$=163.1.

(b) To a stirred solution of 4-(4-fluorophenyl)-1H-imidazole (10 g, 62 mmol) in 95% ethanol (25 mL) was added aqueous formaldehyde solution (37%, 9 mL) slowly. The reaction mixture was stirred at RT for 1 hr before water (25 mL) was added. The reaction mixture was stirred at RT for an additional 3 hr. The solid that separated from solution out was filtered, washed with aqueous ethanol solution, and dried to give (4-(4-fluorophenyl)-1H-imidazol-1-yl)methanol (11.4 g, 59 mmol, 96% yield) as a solid. MS found: $(M+H-CH_2O)^+$=163.1.

(c) To a stirred solution of thionyl chloride (18 mL) in anhydrous methylene chloride (180 mL) was added (4-(4-fluorophenyl)-1H-imidazol-1-yl)methanol (11.4 g, 59 mmol) portionwise at RT under nitrogen. The reaction mixture was stirred at RT for 3.5 hr before anhydrous toluene (90 mL) was added. The mixture was stirred at RT for 30 min. Concentration under reduced pressure gave 1-(chloromethyl)-4-(4-fluorophenyl)-1H-imidazole hydrochloride (14.5 g, 59 mmol, 100% yield) as a solid. MS found: $(M+H)^+$=211.3.

(d) To a stirred solution of 2-methylcyclohexane-1,3-dione (10 g, 79 mmol), lithium iodide (26 g, 194 mmol), and anhydrous THF (300 mL) cooled in a water bath was added 1,8-diazabicyclo[5.4.0]-7-undecene (14 mL, 94 mmol) dropwise under nitrogen. The mixture was stirred at RT for 40 min before 1-(chloromethyl)-4-(4-fluorophenyl)-1H-imidazole hydrochloride (9.8 g, 40 mmol) was added in one portion. The reaction mixture was stirred at RT for 3 hr and at 60° C. for 2 hr. After the mixture was cooled, water (250 mL) and heptane (250 mL) were added. The aqueous layer was separated and extracted with ethyl acetate (2×250 mL). The combined organic solutions were washed with 16% aqueous potassium carbonate solution (3×50 mL), dried ($Na_2SO_4$), and concentrated. Silica gel flash chromatography (20-100% ethyl acetate in hexanes) gave 2((4-(4-fluorophenyl)-1H-imidazol-1-yl)methyl)-2-methylcyclohexane-1,3-dione (7.1 g, 24 mmol, 60% yield) as a solid. MS found: $(M+H)^+$=301.4.

(e) To a stirred solution of diethyl isocyanomethylphosphonate (6.0 mL, 37 mmol) in anhydrous THF (160 mL) was added butyl lithium solution (1.6 M in hexanes, 23 mL, 37 mmol) dropwise at −50 to −60° C. under argon. The mixture was stirred at the same temperature for 30 min before a solution of 2-((4-(4-fluorophenyl)-1H-imidazol-1-yl)methyl)-2-methylcyclohexane-1,3-dione (4.5 g in 30 mL of anhydrous THF, 24 mmol) was added dropwise at −50 to −60° C. The mixture was stirred at the same temperature for 30 min and at RT for 2 hr. The mixture was concentrated under reduced pressure, dissolved in some ethyl acetate, filtered through a silica gel pad which was then rinsed with ethyl acetate. The filtrate was concentrated under reduced pressure to give a solid which was used in the next step without further purification.

(f) One quarter of the above solid was mixed with sodium acetate (1.5 g), acetic acid (4 mL), and water (4 mL). The mixture was heated at 170° C. in a microwave reactor under nitrogen for 30 min. The above microwave reaction was repeated three times. The four microwave reaction mixtures were combined and concentrated under reduced pressure to remove solvents. The residue was mixed with water (40 mL) and ethyl acetate (80 mL) and made basic using potassium carbonate and sodium bicarbonate solid at 0° C. The aqueous layer was separated and extracted with ethyl acetate (3×30 mL). The combined organic solutions were dried ($Na_2SO_4$) and concentrated. Silica gel flash chromatography (30-100% ethyl acetate in hexanes) gave 1-(4-fluorophenyl)-5a-methyl-5,5a,6,7,8,9-hexahydroimidazo[1,5-b]isoquinoline-6-carbaldehyde (2.55 g, 8.2 mmol, 55% yield for steps (e)+(f)) as a solid. MS found: $(M+H)^+$=311.2

(g) 1-(4-fluorophenyl)-5a-methyl-5,5a,6,7,8,9-hexahydroimidazo[1,5-b]isoquinoline-6-carbaldehyde was resolved into its enantiomers using a Chiralpak-AD column and a solvent system of $CO_2$/MeOH. Each enantiomer was converted into the corresponding analogues using the following procedures.

(h) To a stirred solution of (5aR,6S)-1-(4-fluorophenyl)-5a-methyl-5,5a,6,7,8,9-hexahydroimidazo[1,5-b]isoquinoline-6-carbaldehyde (90 mg, 0.29 mmol) in anhydrous THF (2.5 mL) was added thiophen-2-ylmagnesium bromide solution (1 M in THF, 1.5 mL, 1.5 mmol) dropwise at 0° C. under nitrogen. The reaction mixture was stirred at 0° C. for 30 min and at RT for 30 min before saturated aqueous ammonium chloride solution (3 mL) was added. The mixture was extracted with ethyl acetate (3×2 mL). The combined ethyl acetate extracts were dried ($Na_2SO_4$), filtered through a silica gel pad, and concentrated. The crude secondary alcohol mixture was used in the next step without further purification.

(i) The above secondary alcohol was dissolved in anhydrous methylene chloride (2 mL). Pyridine (0.07 mL, 0.87 mmol) and Dess-Martin periodinane (185 mg, 0.44 mmol) were added sequentially. The reaction mixture was stirred at RT for 1 hr before saturated aqueous sodium bicarbonate solution (5 mL) and saturated aqueous sodium thiosulphate solution (3 mL) were added. The mixture was stirred at RT for 30 min. The aqueous layer was separated and extracted with methylene chloride (3×2 mL). The combined organic solutions were dried ($Na_2SO_4$). Silica gel flash chromatography (20-100% ethyl acetate in hexanes) gave ((5aR,6S)-1-(4-fluorophenyl)-5a-methyl-5,5a,6,7,8,9-hexahydroimidazo[1,5-b]isoquinolin-6-yl)(thiophen-2-yl)methanone.

(j) To a stirred solution of the above ((5aR,6S)-1-(4-fluorophenyl)-5a-methyl-5,5a,6,7,8,9-hexahydroimidazo[1,5-b]isoquinolin-6-yl)(thiophen-2-yl)methanone was added methylmagnesium bromide solution (3 M in diethyl ether, 2 mL, 6 mmol) dropwise at −78° C. under argon. The reaction mixture was then stirred at RT for 2.5 hr before saturated aqueous ammonium chloride solution (6 mL) was added slowly with water bath cooling. The mixture was extracted with ethyl acetate (3×5 mL). The combined organic solutions were dried ($Na_2SO_4$) and concentrated. Silica gel flash chromatography (10-100% ethyl acetate in hexanes) gave (S)-1-((5aR,6S)-1-(4-fluorophenyl)-5a-methyl-5,5a,6,7,8,9-hexahydroimidazo[1,5-b]isoquinolin-6-yl)-1-(thiophen-2-yl)ethanol (58 mg, 0.14 mmol, 49% yield for steps (h)+(i)+(j)) as a solid.

MS found: $(M+H)^+$=409.2 $^1$HNMR (400 MHz, $CHCl_3$-d) δ ppm 7.73 (2 H, dd, J=8.90, 5.34 Hz), 7.58 (1H, s), 7.29 (m, under solvent peak), 7.12 (2H, t, J=8.90 Hz), 7.00-7.02 (1H, m), 6.96-6.99 (1H, m), 6.42 (1H, s), 4.99 (1H, d, J=13.22 Hz), 3.88 (1H, d, J=13.23 Hz), 2.41 (2H, m), 2.16 (1H, s), 2.12 (1H, dd, J=12.21, 3.56 Hz), 1.82 (3H, s), 1.63-1.69 (1H, m), 1.59 (1H, dt, J=13.23, 3.05 Hz), 1.34 (3H, s), 1.22-1.31 (1H, m).

Example 2

(5aR,6S)-1-(4-Fluorophenyl)-6-((S)-1-methoxy-1-(thiophen-2-yl)ethyl)-5a-methyl-5,5a,6,7,8,9-hexahydroimidazo[1,5-b]isoquinoline

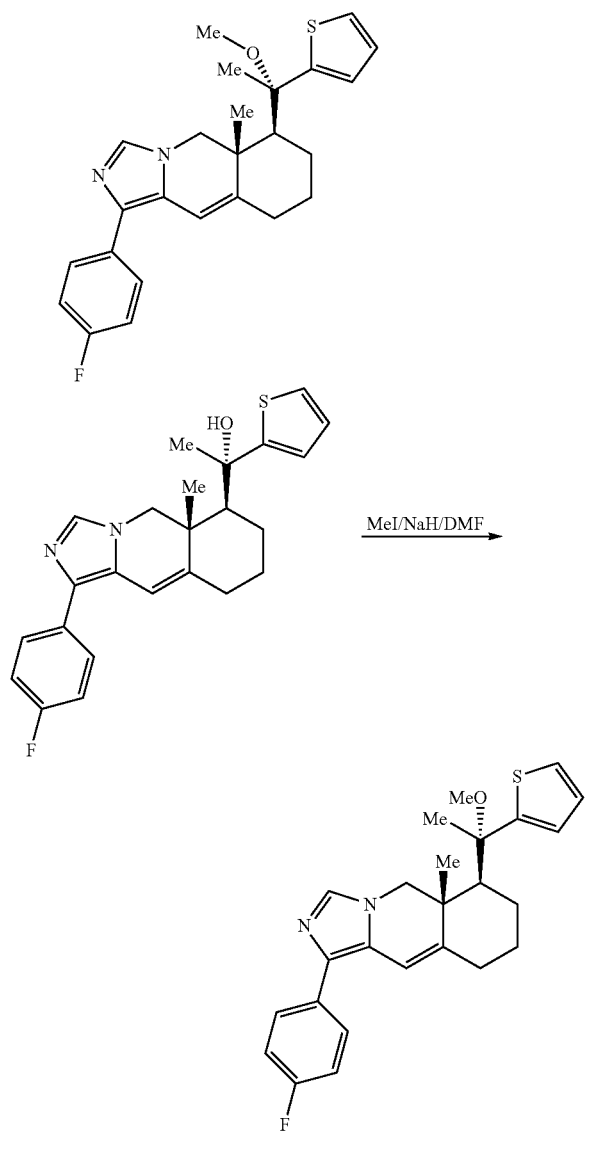

To a stirred solution of (S)-1-((5aR,6S)-1-(4-fluorophenyl)-5a-methyl-5,5a,6,7,8,9-hexahydroimidazo[1,5-b]isoquinolin-6-yl)-1-(thiophen-2-yl)ethanol (13 mg, 0.032 mmol) in anhydrous dimethylformamide (0.3 mL) was added sodium hydride (60% oil dispersion, 9 mg, 0.23 mmol). The mixture was stirred at RT for 40 min before methyl iodide (1 drop) was added. The mixture was stirred at RT for 30 min. Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave (5aR,6S)-1-(4-fluorophenyl)-6-((S)-1-methoxy-1-(thiophen-2-yl)ethyl)-5a-methyl-5,5a,6,7,8,9-hexahydroimidazo[1,5-b]isoquinoline as a trifluoroacetic acid salt (15 mg, 0.028 mmol, 87% yield).

MS found: (M+H)$^+$=423.2. $^1$H-NMR (400 MHz, MeOD) δ ppm 9.00 (1 H, s), 7.64-7.71 (2H, m), 7.41 (1H, dd, J=5.16, 1.13 Hz), 7.33 (2H, t, J=8.69 Hz), 7.07 (1H, dd, J=3.53, 1.26 Hz), 6.98 (1H, dd, J=5.04, 3.53 Hz), 6.48 (1H, s), 5.31 (1H, d, J=13.85 Hz), 4.23 (1H, d, J=14.10 Hz), 3.13 (3H, s), 2.47-2.54 (2H, m), 2.20 (1H, dd, J=12.46, 2.90 Hz), 1.79-1.86 (1H, m), 1.78 (3H, s), 1.60-1.74 (1H, m, J=12.97, 12.97, 12.84, 3.27 Hz), 1.49 (1H, d, J=13.35 Hz), 1.40 (3H, s), 1.17-1.28 (1H, m).

Example 3

5-((S)-1-((5aR,6S)-1-(4-Fluorophenyl)-5a-methyl-5,5a,6,7,8,9-hexahydroimidazo[1,5-b]isoquinolin-6-yl)-1-hydroxyethyl)-N,N-dimethylthiophene-2-carboxamide

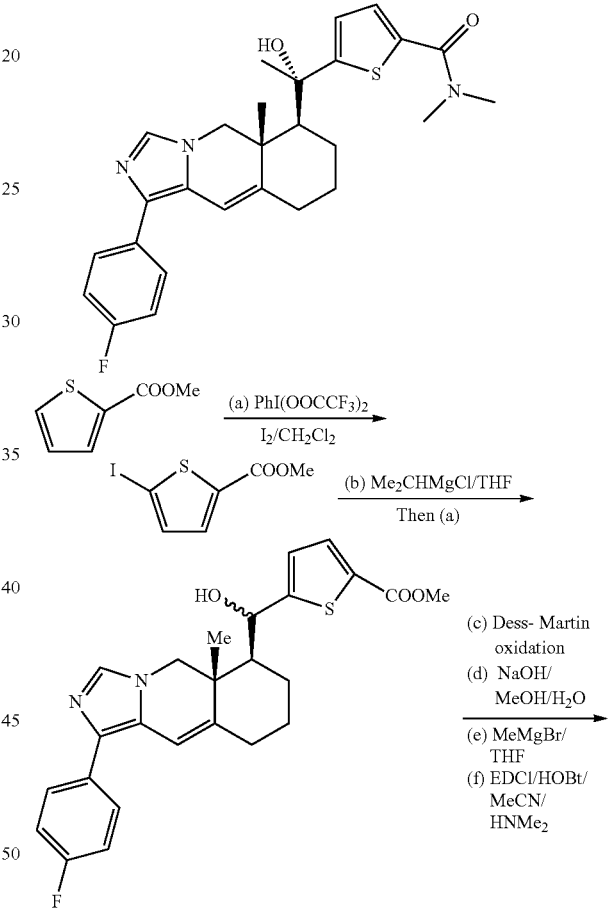

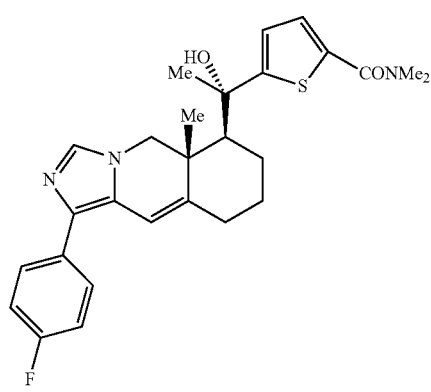

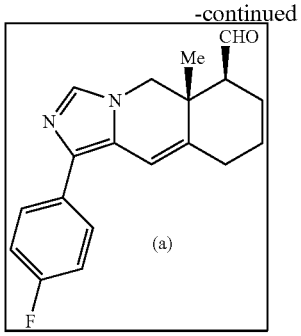

(a)

(a) To a stirred solution of methyl thiophene-2-carboxylate (0.46 mL, 4 mmol) in anhydrous methylene chloride (5 mL) was added iodine (510 mg, 2 mmol) followed by [bis(trifluoroacetoxy)iodo]benzene (900 mg, 2.1 mmol). The reaction mixture was stirred at RT for 1.5 hr before saturated aqueous sodium bicarbonate solution (10 mL) and saturated aqueous sodium thiosulfate solution (2 mL) were added. The mixture was then stirred at RT for 20 min. The aqueous layer was separated and extracted with methylene chloride (2×1 mL). The combined organic solutions were dried ($Na_2SO_4$). Silica gel flash chromatography (0-100% ethyl acetate in hexanes) gave methyl 5-iodothiophene-2-carboxylate (500 mg, 1.9 mmol, 47% yield) as a solid.

(b) To a stirred solution of the above methyl 5-iodothiophene-2-carboxylate (175 mg, 0.65 mmol) in anhydrous THF (2 mL) cooled in an acetonitrile-dry ice bath was added isopropylmagnesium chloride solution (2 M in THF, 0.32 mL, 0.64 mmol) dropwise under nitrogen. The reaction mixture was stirred at the same temperature for 40 min before (5aR,6S)-1-(4-fluorophenyl)-5a-methyl-5,5a,6,7,8,9-hexahydroimidazo[1,5-b]isoquinoline-6-carbaldehyde (Example 1g, 100 mg, 0.32 mmol) was added. After the reaction mixture was stirred at the same temperature for 1 hr, saturated aqueous ammonium chloride solution (3 mL) was added. The mixture was extracted with ethyl acetate (3×2 mL). The combined organic solutions were dried ($Na_2SO_4$) and concentrated. Silica gel flash chromatography (50-100% ethyl acetate in heptanes then 0-20% methanol in ethyl acetate) gave methyl 5-(((5aR,6S)-1-(4-fluorophenyl)-5a-methyl-5,5a,6,7,8,9-hexahydroimidazo[1,5-b]isoquinolin-6-yl)(hydroxy)methyl)thiophene-2-carboxylate as a solid.

(c) The above methyl 5-(((5aR,6S)-1-(4-fluorophenyl)-5a-methyl-5,5a,6,7,8,9-hexahydroimidazo[1,5-b]isoquinolin-6-yl)(hydroxy)methyl)thiophene-2-carboxylate was dissolved in anhydrous methylene chloride (3 mL). Pyridine (0.1 mL) and then Dess-Martin periodinane (204 mg, 0.48 mmol) were added. The reaction mixture was stirred at RT for 1 hr and quenched by the addition of saturated aqueous sodium bicarbonate solution (5 mL) and saturated aqueous sodium thiosulfate solution (2.5 mL). The mixture was stirred at RT for 30 min. The aqueous layer was separated and extracted with methylene chloride (2×2 mL). The combined organic solutions were dried ($Na_2SO_4$). Silica gel flash chromatography (20-100% ethyl acetate in heptanes) gave methyl 5-((5aR,6S)-1-(4-fluorophenyl)-5a-methyl-5,5a,6,7,8,9-hexahydroimidazo[1,5-b]isoquinoline-6-carbonyl)thiophene-2-carboxylate (113 mg, 0.25 mmol, 78% yield for steps (b)+(c)) as a solid. MS found: $(M+H)^+=451.1$.

(d) To a stirred solution of methyl 5-((5aR,6S)-1-(4-fluorophenyl)-5a-methyl-5,5a,6,7,8,9-hexahydroimidazo[1,5-b]isoquinoline-6-carbonyl)thiophene-2-carboxylate (110 mg, 0.24 mmol) in methanol (10 mL) was added aqueous sodium hydroxide solution (1 N, 2 mL, 2 mmol) dropwise followed by water (2 mL). The reaction mixture was stirred at RT for 15 min before neutralized with hydrochloric acid solution (6 N, 0.3 mL) and aqueous 10% citric acid solution. The mixture was concentrated under reduced pressure to remove methanol. The solid was filtered, washed with water, and dried to give 5-((5aR,6S)-1-(4-fluorophenyl)-5a-methyl-5,5a,6,7,8,9-hexahydroimidazo[1,5-b]isoquinoline-6-carbonyl)thiophene-2-carboxylic acid.

(e) The above 5-((5aR,6S)-1-(4-fluorophenyl)-5a-methyl-5,5a,6,7,8,9-hexahydroimidazo[1,5-b]isoquinoline-6-carbonyl)thiophene-2-carboxylic acid was mixed with anhydrous THF (10 mL) and treated with methylmagnesium bromide solution (3 M in diethyl ether, 1 mL, 3 mmol) at −78° C. under nitrogen. The reaction mixture was stirred at RT for 1 hr before ethyl acetate (3 mL) was added with ice-bath cooling. The reaction mixture was stirred at RT for a further 15 min and quenched by the addition of 6 N aqueous hydrochloric acid solution to make the mixture neutral. Concentration and purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 5-((S)-1-((5aR,6S)-1-(4-fluorophenyl)-5a-methyl-5,5a,6,7,8,9-hexahydroimidazo[1,5-b]isoquinolin-6-yl)-1-hydroxyethyl)thiophene-2-carboxylic acid as a trifluoroacetic acid salt (87 mg, 0.15 mmol, 64% yield for steps (d)+(e)). MS found: $(M+H)^+=453.1$.

(f) A mixture of 5-((S)-1-((5aR,6S)-1-(4-fluorophenyl)-5a-methyl-5,5a,6,7,8,9-hexahydroimidazo[1,5-b]isoquinolin-6-yl)-1-hydroxyethyl)thiophene-2-carboxylic acid (trifluoroacetic acid salt, 17 mg, 0.031 mmol), 1-hydroxybenzotriazole hydrate (15 mg, 0.1 mmol), anhydrous acetonitrile (1 mL), EDCI (23 mg, 0.12 mmol), and diisopropylethylamine (0.05 mL) was stirred at RT for 5 min before dimethylamine hydrochloride (25 mg, 0.3 mmol) was added. The mixture was stirred at RT for 2 hr. Concentration under reduced pressure gave a solid which was then triturated with some methanol. The solid obtained was dissolved in a mixture of methanol and trifluoroacetic acid. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 5-((S)-1-((5aR,6S)-1-(4-fluorophenyl)-5a-methyl-5,5a,6,7,8,9-hexahydroimidazo[1,5-b]isoquinolin-6-yl)-1-hydroxyethyl)-N,N-dimethylthiophene-2-carboxamide as a trifluoroacetic acid salt (10 mg, 0.017 mmol, 55% yield).

MS found: $(M+H)^+=480.1$. $^1H$ NMR (400 MHz, MeOD) δ ppm 8.80 (1H, s), 7.54 (2H, dd, J=8.94, 5.16 Hz), 7.17-7.26 (3H, m), 6.91 (1H, d, J=3.78 Hz), 6.36 (1H, s), 5.27 (1H, d, J=13.85 Hz), 4.04 (1H, d, J=13.85 Hz), 3.09 (6H, br. s.), 2.35-2.45 (2H, m), 2.00 (1H, dd, J=11.46, 4.15 Hz), 1.75-1.82 (1H, m), 1.66 (3H, s), 1.57-1.66 (2H, m), 1.32 (3H, s), 1.12-1.19 (1H, m).

Example 4

((5aR,6S)-1-(4-Fluorophenyl)-5a-methyl-5,5a,6,7,8,9-hexahydroimidazo[1,5-b]isoquinolin-6-yl)methanol and N-(((5aR,6S)-1-(4-Fluorophenyl)-5a-methyl-5,5a,6,7,8,9-hexahydroimidazo[1,5-b]isoquinolin-6-yl)methyl)thiazol-2-amine

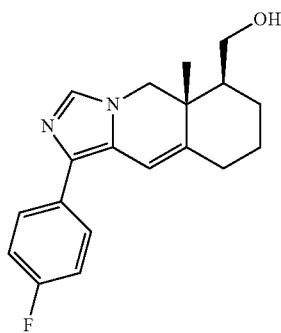

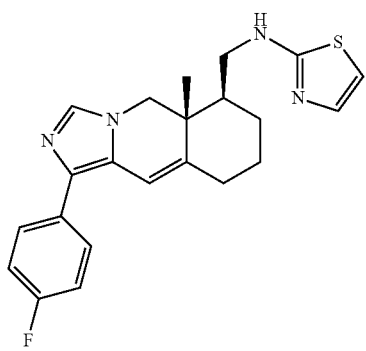

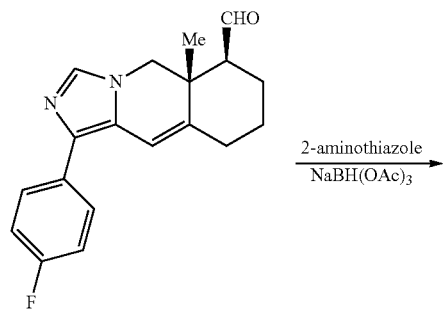

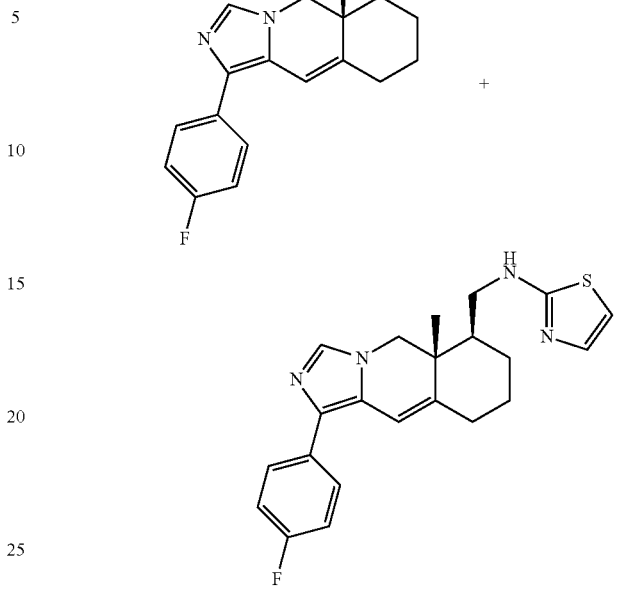

To a stirred mixture of (5aR,6S)-1-(4-fluorophenyl)-5a-methyl-5,5a,6,7,8,9-hexahydroimidazo[1,5-b]isoquinoline-6-carbaldehyde (Example 1g, 16 mg, 0.052 mmol), 2-aminothiazole (44 mg, 0.44 mmol), sodium triacetoxyborohydride (50 mg, 0.24 mmol), and 1,2-dichloroethane (0.7 mL) was added acetic acid (0.03 mL). The mixture was stirred at RT for 2 hr. Concentration and purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave ((5aR,6S)-1-(4-fluorophenyl)-5a-methyl-5,5a,6,7,8,9-hexahydroimidazo[1,5-b]isoquinolin-6-yl)methanol as a trifluoroacetic acid salt (18 mg, 0.042 mmol, 81% yield) and N-(((5aR,6S)-1-(4-fluorophenyl)-5a-methyl-5,5a,6,7,8,9-hexahydroimidazo[1,5-b]isoquinolin-6-yl)methyl)thiazol-2-amine as a trifluoroacetic acid salt (3.6 mg, 0.006 mmol, 13% yield).

Analytical data of ((5aR,6S)-1-(4-fluorophenyl)-5a-methyl-5,5a,6,7,8,9-hexahydroimidazo[1,5-b]isoquinolin-6-yl)methanol: MS found: (M+H)$^+$=313.1. $^1$H NMR (400 MHz, MeOD) δ ppm 8.81 (1H, s), 7.55 (2H, dd, J=9.07, 5.04 Hz), 7.21 (2H, t, J=8.81 Hz), 6.39 (1H, d, J=2.27 Hz), 4.79 (1H, d, J=13.35 Hz), 3.84 (1H, d, J=13.60 Hz), 3.63 (1H, dd, J=11.21, 7.18 Hz), 3.46 (1H, dd, J=11.21, 6.42 Hz), 2.28-2.51 (2H, m), 1.80-1.90 (1H, m), 1.76 (1H, dd, J=11.83, 2.01 Hz), 1.60-1.70 (1H, m), 1.24-1.43 (2H, m), 1.02 (3H, s).

Analytical data of N-(((5aR,6S)-1-(4-fluorophenyl)-5a-methyl-5,5a,6,7,8,9-hexahydroimidazo[1,5-b]isoquinolin-6-yl)methyl)thiazol-2-amine: MS found: (M+H)$^+$=395.1. $^1$H NMR (400 MHz, MeOD) δ ppm 8.78 (1H, s), 7.56 (2H, dd, J=8.94, 5.16 Hz), 7.15-7.26 (3H, m), 6.81 (1H, d, J=4.28 Hz), 6.43 (1H, d, J=2.01 Hz), 4.67 (1H, d, J=13.09 Hz), 3.93 (1H, d, J=13.09 Hz), 3.52 (1H, dd, J=13.35, 3.02 Hz), 3.20-3.28 (1H, m), 2.32-2.52 (2H, m), 1.78-1.95 (3H, m), 1.31-1.53 (2H, m), 1.07 (3H, s).

Example 5

N-(2-((5aR,6R)-1-(4-Fluorophenyl)-5a-methyl-5,5a,6,7,8,9-hexahydroimidazo[1,5-b]isoquinolin-6-yl)ethyl)-1,3,4-thiadiazol-2-amine

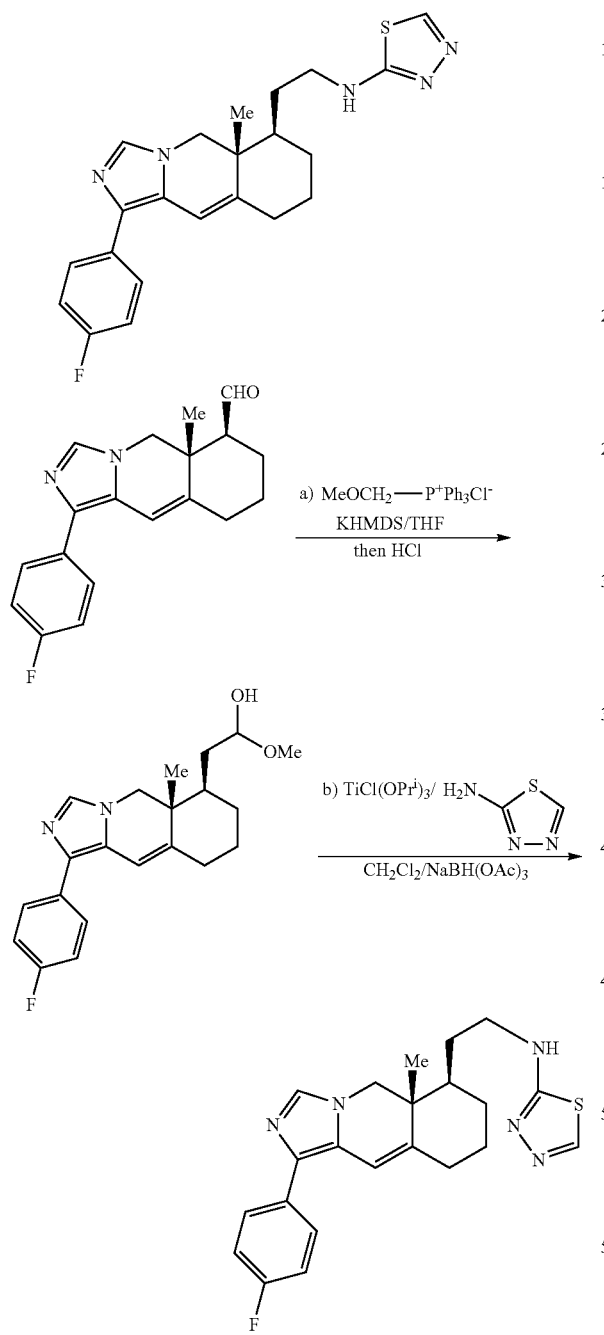

(a) To a stirred suspension of (methoxymethyl)triphenylphosphonium chloride (857 mg, 2.5 mmol) in anhydrous THF (10 mL) was added potassium bis((trimethylsilyl)amide (0.5 M in toluene, 4 mL, 2 mmol) dropwise at 0° C. under nitrogen. The mixture was stirred at 0° C. for 10 min before a solution of (5aR,6S)-1-(4-fluorophenyl)-5a-methyl-5,5a,6,7,8,9-hexahydroimidazo[1,5-b]isoquinoline-6-carbaldehyde (Example 1g, 155 mg in 5 mL of THF, 0.5 mmol) was added at the same temperature. The reaction mixture was stirred at 0° C. for 10 min and at RT for 2 hr. Next, hydrochloric acid solution (6 N, 2 mL) was then added at 0° C. The reaction mixture was stirred at RT for 1.5 hr before concentrated aqueous ammonia solution (1.5 mL) was added at 0° C. The reaction mixture was extracted with heptane (10 mL) and ethyl acetate (2×2 mL). The combined organic solutions were dried ($Na_2SO_4$) and concentrated. Silica gel flash chromatography (0-20% methanol in ethyl acetate) gave 2-((5aR,6R)-1-(4-fluorophenyl)-5a-methyl-5,5a,6,7,8,9-hexahydroimidazo[1,5-b]isoquinolin-6-yl)-1-methoxyethanol (170 mg, 0.48 mmol, 96% yield) as a solid. MS found: $(M+H)^+=357.3$.

(b) To a stirred mixture of 2-((5aR,6R)-1-(4-fluorophenyl)-5a-methyl-5,5a,6,7,8,9-hexahydroimidazo[1,5-b]isoquinolin-6-yl)-1-methoxyethanol (18 mg, 0.05 mmol), 1,3,4-thiadiazol-2-amine (10 mg, 0.1 mmol), and anhydrous methylene chloride (0.5 mL) was added chlorotriisopropoxytitanium solution (1 M in hexanes, 0.2 mL, 0.2 mmol) at RT under nitrogen. The mixture was stirred at RT for 15 min before sodium triacetoxyborohydride (106 mg, 0.5 mmol) was added. The mixture was stirred at RT for 1 hr and quenched by the addition of saturated aqueous sodium bicarbonate solution (3 mL). The aqueous layer was separated and extracted with ethyl acetate (3×2 mL). The combined organic solutions were dried ($Na_2SO_4$) and concentrated. Prep TLC (silica gel, 50% acetone in ethyl acetate) gave N-(2-((5aR,6R)-1-(4-fluorophenyl)-5a-methyl-5,5a,6,7,8,9-hexahydroimidazo[1,5-b]isoquinolin-6-yl)ethyl)-1,3,4-thiadiazol-2-amine (6 mg, 0.015 mmol, 30% yield) as a solid.

MS found: $(M+H)^+=410.3$. $^1H$ NMR (500 MHz, CHLOROFORM-d) δ ppm 8.34 (1H, s), 7.55-7.59 (2H, m), 7.40 (1H, s), 7.01 (2H, t, J=8.66 Hz), 6.68 (1H, br. s.), 6.27 (1H, s), 4.09 (1H, d, J=12.65 Hz), 3.48-3.54 (1H, br. m.), 3.43 (1H, d, J=12.65 Hz), 3.22-3.30 (1H, br. m.), 2.28 (2H, d, J=4.67 Hz), 1.76-1.89 (3H, m), 1.40-1.49 (2H, m), 1.24-1.31 (2H, m), 0.93 (3H, s).

Example 6

2-((5aR,6R)-1-(4-Fluorophenyl)-5a-methyl-5,5a,6,7,8,9-hexahydroimidazo[1,5-b]isoquinolin-6-yl)-N-(thiazol-2-yl)acetamide

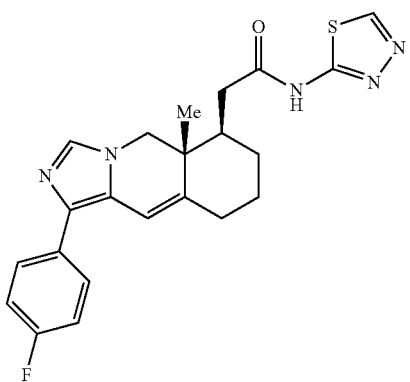

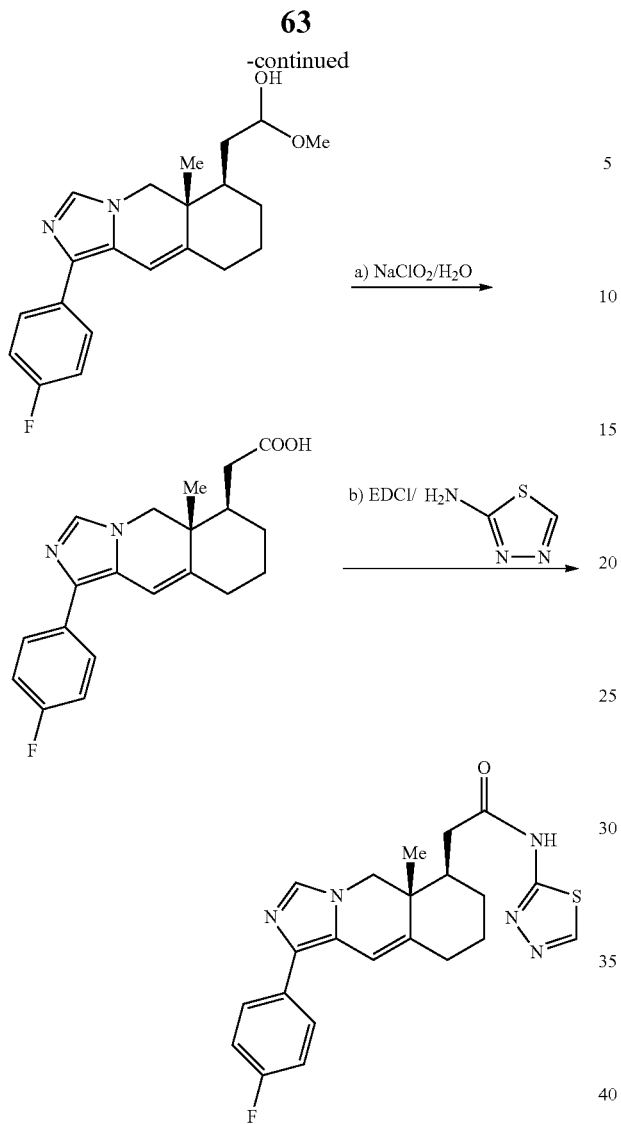

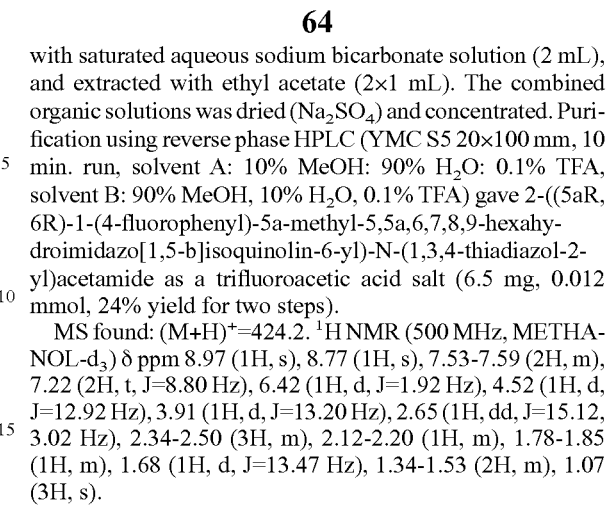

with saturated aqueous sodium bicarbonate solution (2 mL), and extracted with ethyl acetate (2×1 mL). The combined organic solutions was dried ($Na_2SO_4$) and concentrated. Purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 2-((5aR,6R)-1-(4-fluorophenyl)-5a-methyl-5,5a,6,7,8,9-hexahydroimidazo[1,5-b]isoquinolin-6-yl)-N-(1,3,4-thiadiazol-2-yl)acetamide as a trifluoroacetic acid salt (6.5 mg, 0.012 mmol, 24% yield for two steps).

MS found: $(M+H)^+=424.2$. $^1H$ NMR (500 MHz, METHANOL-$d_3$) δ ppm 8.97 (1H, s), 8.77 (1H, s), 7.53-7.59 (2H, m), 7.22 (2H, t, J=8.80 Hz), 6.42 (1H, d, J=1.92 Hz), 4.52 (1H, d, J=12.92 Hz), 3.91 (1H, d, J=13.20 Hz), 2.65 (1H, dd, J=15.12, 3.02 Hz), 2.34-2.50 (3H, m), 2.12-2.20 (1H, m), 1.78-1.85 (1H, m), 1.68 (1H, d, J=13.47 Hz), 1.34-1.53 (2H, m), 1.07 (3H, s).

Example 7

1-tert-Butyl-3-(2-((5aR,6R)-1-(4-fluorophenyl)-5a-methyl-5,5a,6,7,8,9-hexahydroimidazo[1,5-b]isoquinolin-6-yl)ethyl)urea (a) To a stirred mixture of 2-((5aR,6R)-1-(4-fluorophenyl)-5a-methyl-5,5a,6,7,8,9-hexahydroimidazo[1,5-b]isoquinolin-6-yl)-1-methoxyethanol (Example 5a, 90 mg, 0.25 mmol), 2-methylbut-2-ene (2 M in THF, 1 mL), tert-butanol (0.5 mL) and trifluoroacetic acid (0.03 mL, 0.4 mmol) was added a solution of sodium chlorite (80%, 70 mg, 0.62 mmol) and sodium dihydrogenphosphate monohydrate (80 mg, 0.58 mmol) in water (0.6 mL) at 0° C. The reaction mixture was then stirred at RT for 1.5 hr. The aqueous layer was separated, extracted with THF (1.5 mL), neutralized with solid sodium bicarbonate to pH=6, and extracted with THF (2×1 mL). The combined organic solutions were dried ($Na_2SO_4$) and concentrated to give 2-((5aR,6R)-1-(4-fluorophenyl)-5a-methyl-5,5a,6,7,8,9-hexahydroimidazo[1,5-b]isoquinolin-6-yl)acetic acid (195 mg) which was used in the next step without further purification. MS found: $(M+H)^+=341.2$.

(b) A mixture of the above 2-((5aR,6R)-1-(4-fluorophenyl)-5a-methyl-5,5a,6,7,8,9-hexahydroimidazo[1,5-b]isoquinolin-6-yl)acetic acid (40 mg, 0.05 mmol), 1-hydroxybenzotriazole hydrate (8 mg, 0.05 mmol), anhydrous acetonitrile (1 mL), EDCI (100 mg, 0.52 mmol), and diisopropylethylamine (0.1 mL) was stirred at RT for 5 min before 1,3,4-thiadiazol-2-amine (15 mg, 0.15 mmol) was added. After stirring at RT for 2 days, the mixture was concentrated, mixed

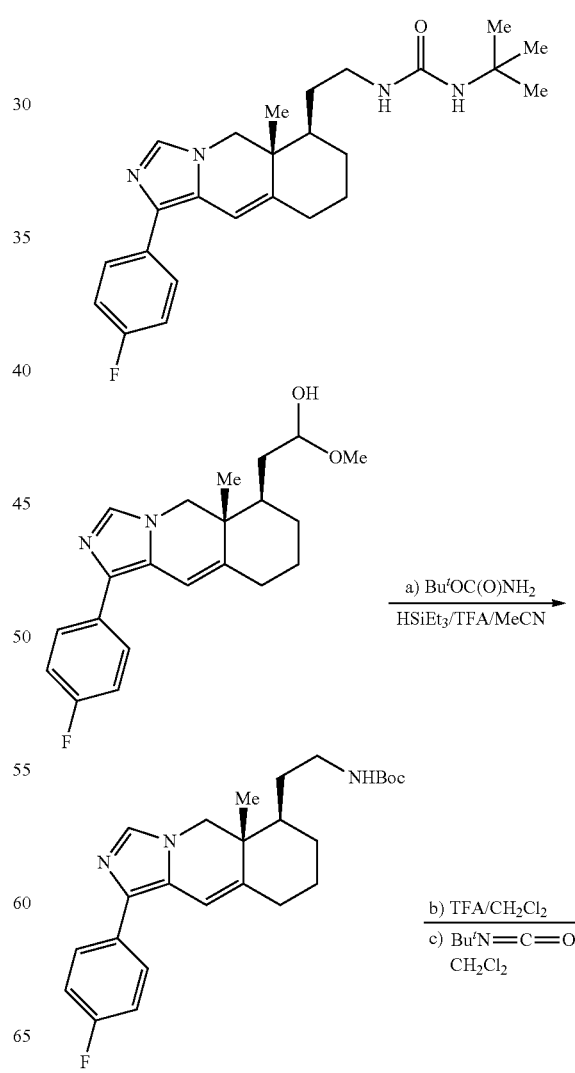

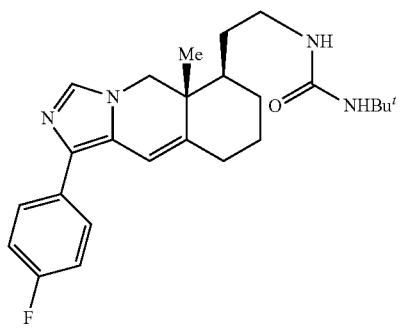

(a) To a stirred mixture of 2-((5aR,6R)-1-(4-fluorophenyl)-5a-methyl-5,5a,6,7,8,9-hexahydroimidazo[1,5-b]isoquinolin-6-yl)-1-methoxyethanol (Example 5a, 36 mg, 0.1 mmol), tert-butyl carbamate (35 mg, 0.3 mmol), triethylsilane (0.1 mL), and acetonitrile (0.5 mL) was added trifluoroacetic acid (0.03 mL). The mixture was stirred at RT for 40 hr. Concentration and purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave tert-butyl 2-((5aR,6R)-1-(4-fluorophenyl)-5a-methyl-5,5a,6,7,8,9-hexahydroimidazo[1,5-b]isoquinolin-6-yl)ethylcarbamate as a trifluoroacetic acid salt (23 mg, 0.043 mmol, 43% yield). MS found: $(M+H)^+$=426.3.

(b) To a stirred solution of tert-butyl 2-((5aR,6R)-1-(4-fluorophenyl)-5a-methyl-5,5a,6,7,8,9-hexahydroimidazo[1,5-b]isoquinolin-6-yl)ethylcarbamate (trifluoroacetic acid salt, 20 mg, 0.037 mmol) in methylene chloride (2 mL) was added trifluoroacetic acid (1 mL). The mixture was stirred at RT for 2 hr. Concentration gave a solid (20 mg), which was used in the next step without further purification.

(c) To a stirred solution of the above solid (10 mg, 0.018 mmol) and diisopropylethylamine (0.1 mL) in methylene chloride (1 mL) was added tert-butylisocyanate (0.01 mL, 0.088 mmol). The mixture was stirred at RT for 1 hr before saturated aqueous sodium bicarbonate solution (2 mL) was added. The aqueous layer was separated and extracted with ethyl acetate (2×1 mL). The combined organic solutions were dried ($Na_2SO_4$). Concentration and purification using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) gave 1-tert-butyl-3-(2-((5aR,6R)-1-(4-fluorophenyl)-5a-methyl-5,5a,6,7,8,9-hexahydroimidazo[1, 5-b]isoquinolin-6-yl)ethyl)urea as a trifluoroacetic acid salt (7.7 mg, 0.014 mmol, 76% yield for steps (b)+(c)). MS found: $(M+H)^+$=425.3. $^1$H NMR (500 MHz, METHANOL-$d_3$) δ ppm 8.85 (1H, s), 7.58-7.69 (2H, m), 7.30 (2H, t, J=8.80 Hz), 6.45 (1H, d, J=2.20 Hz), 4.60 (1H, d, J=13.20 Hz), 3.83 (1H, d, J=12.92 Hz), 3.22 (1H, ddd, J=13.47, 8.52, 4.67 Hz), 3.08 (1H, dt, J=13.54, 7.80 Hz), 2.43-2.55 (2H, m), 1.92 (2H, dd, J=10.17, 1.65 Hz), 1.64-1.72 (1H, m), 1.49-1.57 (1H, m), 1.38-1.46 (2H, m), 1.33 (1 H, s), 1.30 (9H, s), 1.08 (3H, s).

Example 8

(5aR,6S)-1-(4-Fluorophenyl)-6-((S)-1-methoxy-1-(thiophen-2-yl)ethyl)-5a-methyl-5,5a,6,7,8,9-hexahydroimidazo[1,5-b]isoquinoline

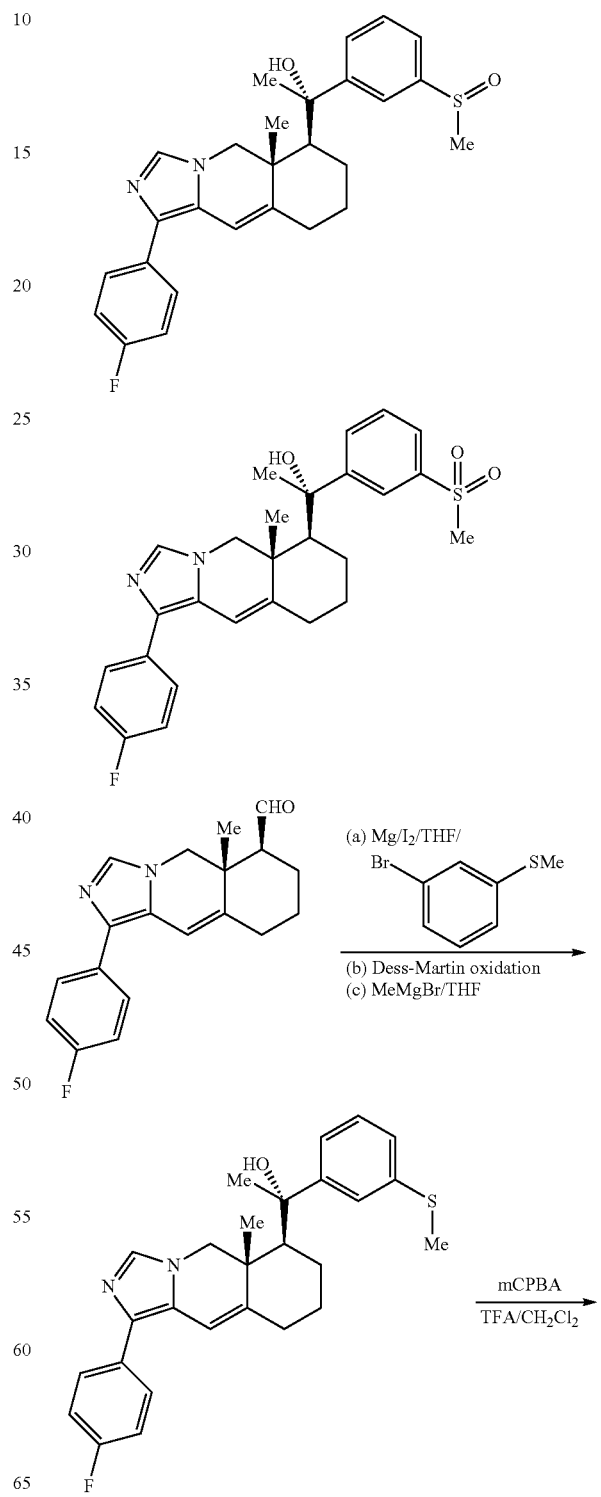

-continued

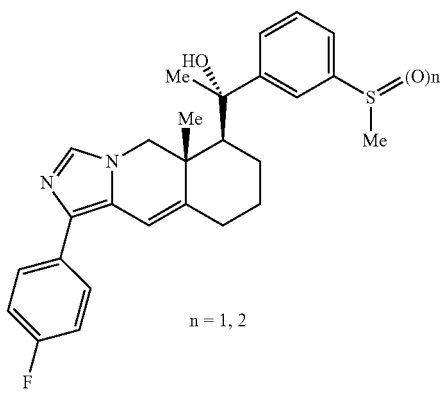

n = 1, 2

(a) To a stirred mixture of magnesium turning (24 mg, 1 mmol) and anhydrous THF (1 mL) were added a pinch of iodine and 3-bromothioanisole (0.14 mL, 1 mmol) at RT under nitrogen. The mixture was heated slowly to 65° C. and then stirred at 65° C. for 1 hr. (5aR,6S)-1-(4-fluorophenyl)-5a-methyl-5,5a,6,7,8,9-hexahydroimidazo[1,5-b]isoquinoline-6-carbaldehyde (Example 1g 40 mg, 0.13 mmol) was added at 0° C. The mixture was stirred at 0° C. for 30 min and at RT for 30 min. Saturated aqueous ammonium chloride solution (2 mL) was added to quench the reaction and the reaction mixture was extracted with ethyl acetate (3×1 mL). The combined organic solutions were dried ($Na_2SO_4$), filtered through a silica gel pad, and concentrated to give a liquid mixture which was used in the next step without further purification.

(b) The above liquid was dissolved in anhydrous methylene chloride (1 mL). Pyridine (0.06 mL, 0.74 mmol) and Dess-Martin periodinane (180 mg, 0.42 mmol) were added. The mixture was stirred at RT for 1 hr before saturated aqueous sodium bicarbonate solution (3 mL) and saturated aqueous sodium thiosulfate solution (1.5 mL) were added. The mixture was stirred at RT for 30 min. The aqueous layer was separated and extracted with methylene chloride (2×1 mL). The combined organic solutions were dried ($Na_2SO_4$). Silica gel flash chromatography (10-100% ethyl acetate in hexanes) gave the ketone intermediate which was used as such for the subsequent step without further purification.

(c) The above ketone intermediate was dissolved in anhydrous THF (1 mL) and treated with methylmagnesium bromide solution (3 M in diethyl ether, 0.5 mL, 1.5 mmol) at −78° C. under nitrogen. The mixture was then stirred at RT for 1 hr. Ethyl acetate (0.5 mL) was added at 0° C. The mixture was stirred at RT for 30 min before being quenched by the addition of saturated aqueous ammonium chloride solution (2 mL). The aqueous layer was extracted with ethyl acetate (2×1 mL). The combined organic solutions were dried ($Na_2SO_4$) and concentrated. Silica gel flash chromatography (10-100% ethyl acetate in hexanes) gave (S)-1-((5aR,6S)-1-(4-fluorophenyl)-5a-methyl-5,5a,6,7,8,9-hexahydroimidazo[1,5-b]isoquinolin-6-yl)-1-(3-(methylthio)phenyl)ethanol (46 mg, 0.1 mmol, 78% yield for steps (a)+(b)+(c)) as a solid. MS found: $(M+H)^+=449.2$.

(d) To a stirred solution of (S)-1-((5aR,6S)-1-(4-fluorophenyl)-5a-methyl-5,5a,6,7,8,9-hexahydroimidazo[1,5-b]isoquinolin-6-yl)-1-(3-(methylthio)phenyl)-ethanol (33 mg, 0.074 mmol) and trifluoroacetic acid (0.1 mL) in methylene chloride (1 mL) was added m-CPBA (ca 77%, 31 mg, 0.13 mmol) at 0° C. The mixture was stirred at 0° C. for 1 hr and at RT for 1 hr. The mixture was concentrated and partitioned between ethyl acetate (2 mL) and saturated aqueous sodium bicarbonate solution (2 mL). The aqueous layer was separated and extracted with ethyl acetate (2×1 mL). The combined organic solutions were dried ($Na_2SO_4$) and concentrated. Silica gel flash chromatography (20-100% ethyl acetate in heptanes and then 0-20% methanol in ethyl acetate) gave (S)-1-((5aR,6S)-1-(4-fluorophenyl)-5a-methyl-5,5a,6,7,8,9-hexahydroimidazo[1,5-b]isoquinolin-6-yl)-1-(3-(methylsulfonyl)phenyl)ethanol and (1S)-1-((5aR,6S)-1-(4-fluorophenyl)-5a-methyl-5,5a,6,7,8,9-hexahydroimidazo[1,5-b]isoquinolin-6-yl)-1-(3-(methylsulfinyl)phenyl)ethanol. Each of the compounds was individually purified again using reverse phase HPLC (YMC S5 20×100 mm, 10 min. run, solvent A: 10% MeOH: 90% $H_2O$: 0.1% TFA, solvent B: 90% MeOH, 10% $H_2O$, 0.1% TFA) to give (S)-1-((5aR,6S)-1-(4-fluorophenyl)-5a-methyl-5,5a,6,7,8,9-hexahydroimidazo[1,5-b]isoquinolin-6-yl)-1-(3-(methylsulfonyl)phenyl)ethanol as a trifluoroacetic acid salt (6 mg, 0.01 mmol, 14% yield) and (1S)-1-((5aR,6S)-1-(4-fluorophenyl)-5a-methyl-5,5a,6,7,8,9-hexahydroimidazo[1,5-b]isoquinolin-6-yl)-1-(3-(methylsulfinyl)phenyl)ethanol as a trifluoroacetic acid salt (10 mg, 0.017 mmol, 23% yield).

Analytical data of (S)-1-((5aR,6S)-1-(4-fluorophenyl)-5a-methyl-5,5a,6,7,8,9-hexahydroimidazo[1,5-b]isoquinolin-6-yl)-1-(3-(methylsulfonyl)phenyl)ethanol (trifluoroacetic acid salt): MS found: $(M+H)^+=481.2$. $^1$H NMR (400 MHz, MeOD) δ ppm 8.72 (1H, s), 8.05 (1H, t, J=1.76 Hz), 7.84 (1H, d, J=7.81 Hz), 7.77 (1H, d, J=1.76 Hz), 7.51-0.57 (3H, m), 7.21 (2H, t, J=8.81 Hz), 6.34 (1H, s), 5.20 (1H, d, J=13.85 Hz), 4.07 (1H, d, J=13.85 Hz), 3.04 (3H, s), 2.38 (2H, dd, J=7.30, 2.52 Hz), 1.85-1.92 (1H, m), 1.70-1.78 (1H, m), 1.65 (3H, s), 1.57-1.66 (1H, m), 1.43-1.52 (1H, m), 1.35 (3H, s), 1.02-1.16 (1H, m).

Analytical data of (1S)-1-((5aR,6S)-1-(4-fluorophenyl)-5a-methyl-5,5a,6,7,8,9-hexahydroimidazo[1,5-b]isoquinolin-6-yl)-1-(3-(methylsulfinyl)phenyl)ethanol (trifluoroacetic acid salt/diastereomeric mixture): MS found: $(M+H)^+=465.2$. $^1$H NMR (400 MHz, MeOD) δ ppm 8.76 (1H, s), 7.87 (1H, d, J=19.64 Hz), 7.64-7.73 (1H, m), 7.51-7.58 (2H, m), 7.46-7.51 (2H, m), 7.21 (2H, t, J=8.81 Hz), 6.34 (1H, s), 5.19 (1H, dd, J=16.12, 13.85 Hz), 4.07 (1H, dd, J=13.72, 2.90 Hz), 2.72 (3H, s), 2.38 (2H, d, J=4.53 Hz), 1.90 (1H, dt, J=12.21, 3.08 Hz), 1.69-1.78 (1H, m), 1.65 (3H, s), 1.56-1.67 (1H, m), 1.44-1.52 (1H, m), 1.34 (3H, s), 0.99-1.16 (1H, m).

Example 9

2-(3-((S)-1-((5aR,6S)-1-(4-Fluorophenyl)-5a-methyl-5,5a,6,7,8,9-hexahydroimidazo[1,5-b]isoquinolin-6-yl)-1-hydroxyethyl)phenyl)propan-2-ol

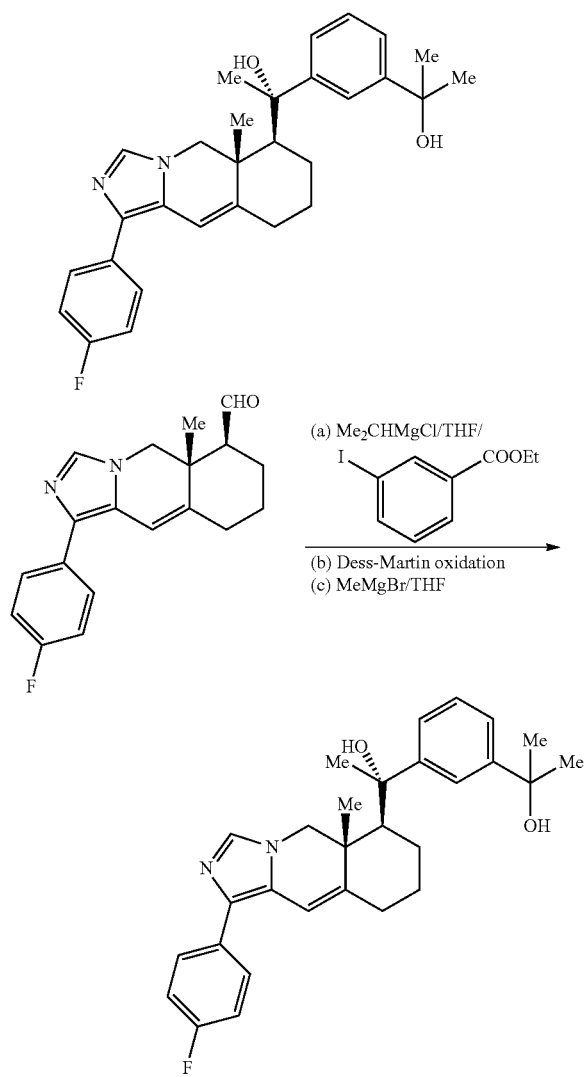

(a) To a stirred solution of ethyl 3-iodobenzoate (0.17 mL, 1 mmol) in anhydrous THF (2 mL) cooled in an acetonitrile-dry ice bath was added isopropylmagnesium chloride solution (2M in THF, 0.5 mL, 1 mmol) dropwise under nitrogen. The reaction mixture was stirred at the same temperature for 30 min before (5aR,6S)-1-(4-fluorophenyl)-5a-methyl-5,5a, 6,7,8,9-hexahydroimidazo[1,5-b]isoquinoline-6-carbaldehyde (Example 1g, 55 mg, 0.18 mmol) was added. The mixture was stirred in an acetonitrile-dry ice bath for 1 hr before being quenched by the addition of saturated aqueous ammonium chloride solution (3 mL) at the same temperature. The reaction mixture was extracted with ethyl acetate (3×3 mL). The combined organic solutions were dried (Na$_2$SO$_4$) and concentrated. Silica gel flash chromatography (25-100% ethyl acetate in heptanes, then 0-10% methanol in ethyl acetate) gave ethyl 3-(((5aR,6S)-1-(4-fluorophenyl)-5a-methyl-5,5a,6,7,8,9-hexahydroimidazo[1,5-b]isoquinolin-6-yl)(hydroxy)methyl)benzoate as a solid.

(b) The above ethyl 3-(((5aR,6S)-1-(4-fluorophenyl)-5a-methyl-5,5a,6,7,8,9-hexahydroimidazo[1,5-b]isoquinolin-6-yl)(hydroxy)methyl)benzoate was dissolved in anhydrous methylene chloride (5 mL). Pyridine (0.1 mL) and Dess-Martin periodinane (215 mg, 0.51 mmol) were added. The reaction mixture was stirred at RT for 40 min before saturated aqueous sodium bicarbonate solution (6 mL) and saturated aqueous sodium thiosulfate solution (3 mL) were added. The mixture was stirred at RT for 20 min. The aqueous layer was separated and extracted with methylene chloride (2×2 mL). The combined organic solutions were dried (Na$_2$SO$_4$). Silica gel flash chromatography (20-100% ethyl acetate in heptanes, then 0-20% methanol in ethyl acetate) gave ethyl 3-((5aR,6S)-1-(4-fluorophenyl)-5a-methyl-5,5a,6,7,8,9-hexahydroimidazo[1,5-b]isoquinoline-6-carbonyl)benzoate as a solid.

(c) The above ethyl 3-((5aR,6S)-1-(4-fluorophenyl)-5a-methyl-5,5a,6,7,8,9-hexahydroimidazo[1,5-b]isoquinoline-6-carbonyl)benzoate was dissolved in anhydrous THF (5 mL) and treated with methylmagnesium bromide solution (3 M in diethyl ether, 1.5 mL, 4.5 mmol) at −78° C. under nitrogen. The mixture was stirred at RT for 20 min before pouring into saturated aqueous ammonium chloride solution (5 mL) slowly. The aqueous layer was separated and extracted with ethyl acetate (2×2 mL). The combined organic solutions were dried (Na$_2$SO$_4$). Concentration and purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave 2-(3-((S)-1-((5aR,6S)-1-(4-fluorophenyl)-5a-methyl-5,5a,6,7,8,9-hexahydroimidazo[1,5-b] isoquinolin-6-yl)-1-hydroxyethyl)phenyl)propan-2-ol as a trifluoroacetic acid salt (63 mg, 0.11 mmol, 61% yield for steps (a)+(b)+(c)).

MS found: (M+H)$^+$=461.3. $^1$HNMR (400 MHz, MeOD) δ ppm 8.59 (1H, s), 7.64 (1H, t, J=1.64 Hz), 7.50-7.56 (2H, m), 7.33 (1H, d, J=7.55 Hz), 7.26-7.29 (1H, m), 7.17-7.24 (3H, m), 6.31 (1H, s), 4.90 (1H, d, J=13.85 Hz), 4.00 (1H, d, J=13.85 Hz), 2.35-2.41 (2H, m), 1.89-1.95 (1H, m), 1.71-1.79 (1H, m), 1.60 (3H, s), 1.56-1.65 (1H, m, overlapped), 1.44-1.47 (1H, m overlapped), 1.44 (6H, s), 1.32 (3H, s), 1.06-1.17 (1H, m).

Example 10

(S)-1,1,1-Trifluoro-2-((5aR,6S)-1-(4-fluorophenyl)-5a-methyl-5,5a,6,7,8,9-hexahydroimidazo[1,5-b]isoquinolin-6-yl)propan-2-ol

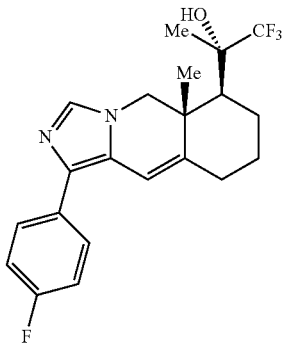

71

-continued

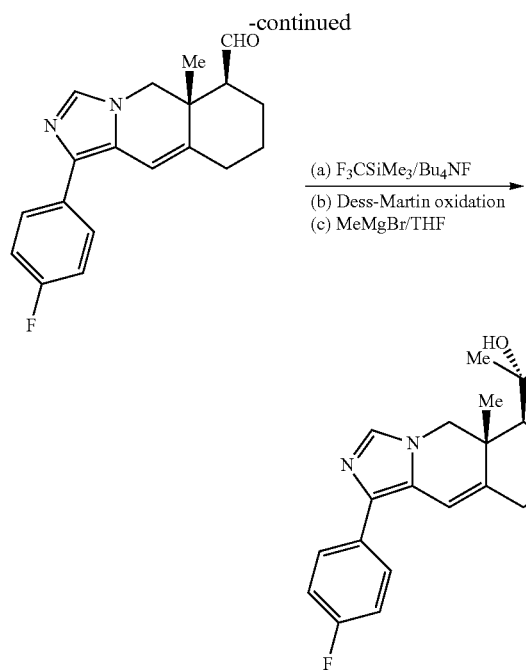

(a) F₃CSiMe₃/Bu₄NF
(b) Dess-Martin oxidation
(c) MeMgBr/THF (a) To a stirred solution of (5aR,6S)-1-(4-fluorophenyl)-5a-methyl-5,5a,6,7,8,9-hexahydroimidazo[1,5-b]isoquinoline-6-carbaldehyde (Example 1g, 22 mg, 0.07 mmol) in trimethyl(trifluoromethyl)silane solution (0.5 M in THF, 1.5 mL, 0.75 mmol) cooled in a water bath was added tetrabutylammonium fluoride solution (1 M in THF, 0.17 mL, 0.17 mmol) dropwise. The reaction mixture was stirred at RT for 30 min before saturated aqueous ammonium chloride solution (2 mL) was added. The mixture was extracted with heptane (0.5 mL) and ethyl acetate (2×1 mL). The combined organic solutions were dried (Na₂SO₄). Concentration and purification using reverse phase HPLC (YMC S5 20×100 mm, 10 min. run, solvent A: 10% MeOH: 90% H₂O: 0.1% TFA, solvent B: 90% MeOH, 10% H₂O, 0.1% TFA) gave 2,2,2-trifluoro-1-((5aR,6S)-1-(4-fluorophenyl)-5a-methyl-5,5a,6,7,8,9-hexahydroimidazo[1,5-b]isoquinolin-6-yl)ethanol as a trifluoroacetic acid salt (25 mg, 0.051 mmol, 73% yield). MS found: (M+H)⁺=381.3.

(b) and (c) The above 2,2,2-trifluoro-1-((5aR,6S)-1-(4-fluorophenyl)-5a-methyl-5,5a,6,7,8,9-hexahydroimidazo[1,5-b]isoquinolin-6-yl)ethanol (trifluoroacetic acid salt, 9 mg, 0.018 mmol) was converted to (S)-1,1,1-trifluoro-2-((5aR,6S)-1-(4-fluorophenyl)-5a-methyl-5,5a,6,7,8,9-hexahydroimidazo[1,5-b]isoquinolin-6-yl)propan-2-ol and (R)-1,1,1-trifluoro-2-((5aR,6S)-1-(4-fluorophenyl)-5a-methyl-5,5a,6,7,8,9-hexahydroimidazo[1,5-b]isoquinolin-6-yl)propan-2-ol using procedures outlined for Example 9(b) and 9(c).

Analytical data of (S)-1,1,1-trifluoro-2-((5aR,6S)-1-(4-fluorophenyl)-5a-methyl-5,5a,6,7,8,9-hexahydroimidazo[1,5-b]isoquinolin-6-yl)propan-2-ol (trifluoroacetic acid salt): MS found: (M+H)⁺=395.2. ¹HNMR (400 MHz, MeOD) δ ppm 8.96 (1H, s), 7.64 (2H, dd, J=8.9, 5.2 Hz), 7.31 (2H, t, J=8.8 Hz), 6.48 (1H, d, J=2.0 Hz), 5.56 (1H, d, J=13.8 Hz), 3.93 (1H, d, J=13.8 Hz), 2.46-2.56 (2H, m), 2.18 (1H, dd, J=12.7, 3.4 Hz), 1.86-1.98 (2H, m), 1.69-1.78 (1H, m), 1.51 (3H, s), 1.38-1.45 (1H, m), 1.36 (3H, s).

72

Example 11

(S)-1-((5aR,6S)-1-(4-Fluorophenyl)-5a-methyl-5,5a,6,7,8,9-hexahydroimidazo[1,5-b]isoquinolin-6-yl)-1-(pyrimidin-2-yl)ethanol

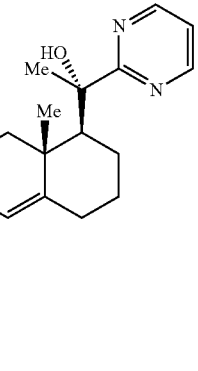

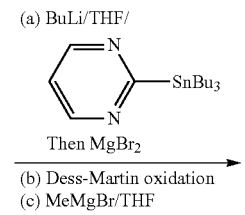

(a) BuLi/THF/
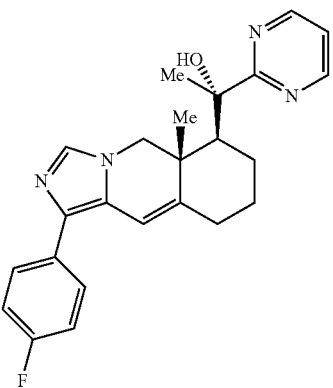
Then MgBr₂
(b) Dess-Martin oxidation
(c) MeMgBr/THF (a) To a stirred solution of 2-(tributylstannyl)pyrimidine (185 mg, 0.5 mmol) in anhydrous THF (1 mL) was added butyllithium solution (1.6 M in hexanes, 0.31 mL, 0.5 mmol) dropwise at −78° C. under nitrogen. The mixture was stirred at −78° C. for 2 hr before magnesium bromide (90 mg, 0.5 mmol) was added. After the reaction mixture was stirred at −78° C. for additional 30 min, (5aR,6S)-1-(4-fluorophenyl)-5a-methyl-5,5a,6,7,8,9-hexahydroimidazo[1,5-b]isoquinoline-6-carbaldehyde (Example 1g, 20 mg, 0.065 mmol) was added. The mixture was stirred at −78° C. for 45 min and at RT for 5 min. Saturated aqueous ammonium chloride solution (2 mL) was added. The reaction mixture was extracted with ethyl acetate (3×1 mL). The combined organic solutions were dried (Na₂SO₄) and concentrated. Silica gel flash chromatography (50-100% ethyl acetate in heptanes and then 0-20% methanol in ethyl acetate) gave ((5aR,6S)-1-(4-fluorophenyl)-5a-methyl-5,5a,6,7,8,9-hexahydroimidazo[1,5-b]isoquinolin-6-yl)(pyrimidin-2-yl)methanol which was used as such for the subsequent step without further purification.

(b) and (c) The above ((5aR,6S)-1-(4-fluorophenyl)-5a-methyl-5,5a,6,7,8,9-hexahydroimidazo[1,5-b]isoquinolin-6-yl)(pyrimidin-2-yl)methanol was converted to (S)-1-((5aR,6S)-1-(4-fluorophenyl)-5a-methyl-5,5a,6,7,8,9-hexahydroimidazo[1,5-b]isoquinolin-6-yl)-1-(pyrimidin-2-yl)ethanol using procedures outlined for Example 9(b) and 9(c).

Analytical data of (S)-1-((5aR,6S)-1-(4-fluorophenyl)-5a-methyl-5,5a,6,7,8,9-hexahydroimidazo[1,5-b]isoquinolin-6-yl)-1-(pyrimidin-2-yl)ethanol (trifluoroacetic acid salt): MS found: (M+H)$^+$=405.2. $^1$HNMR (400 MHz, MeOD) δ ppm 8.81-8.87 (3H, m), 7.60-7.68 (2H, m), 7.41 (1H, t, J=4.9 Hz), 7.31 (2H, t, J=8.8 Hz), 6.43 (1H, s), 4.96 (2H, d, J=13.6 Hz), 4.03 (1H, d, J=13.6 Hz), 2.44-2.53 (2H, m), 2.27-2.35 (1H, m), 1.81-1.89 (1H, m), 1.66-1.79 (4H, m), 1.44 (3H, s), 1.18-1.34 (1H, m).

Examples 12 to 101

Compounds in Table 1 (below) were synthesized using the protocols outlined above.

TABLE 1

| Example No. | Structure | LC Retention Time (Min.)/Column* | LC-MS [M + H]$^+$ | Procedure of Example |
|---|---|---|---|---|
| 12 (±) | 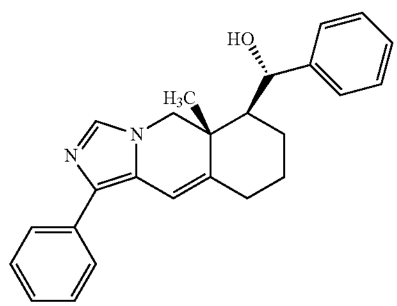 | 3.20 | 371.3 | 1 |
| 13 Enantiomer 1 | 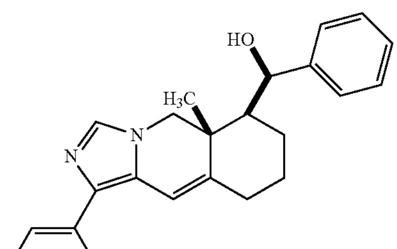 | 3.04 | 371.3 | 1 |
| 14 Enantiomer 2 | 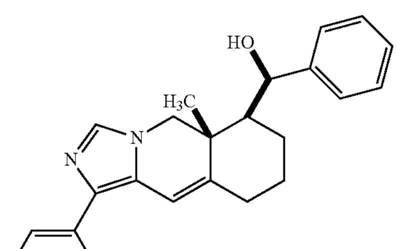 | 3.04 | 371.3 | 1 |
| 15 (±) | 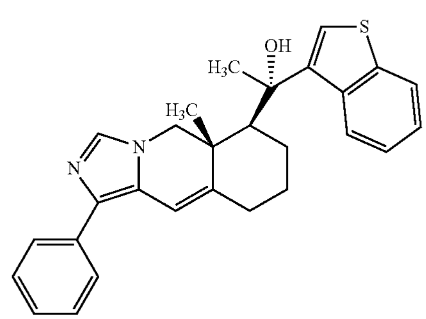 | 3.42 | 441.4 | 8 |

TABLE 1-continued

| Example No. | Structure | LC Retention Time (Min.)/Column* | LC-MS [M + H]+ | Procedure of Example |
|---|---|---|---|---|
| 16 (±) | 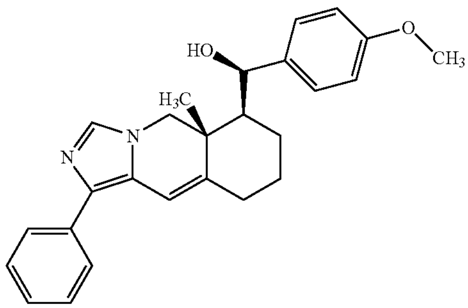 | 3.01 | 401.4 | 1 |
| 17 (±) | 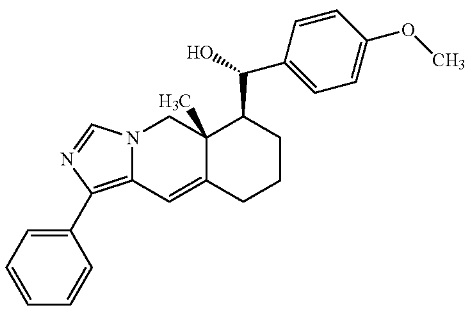 | 3.20 | 401.4 | 1 |
| 18 (±) | 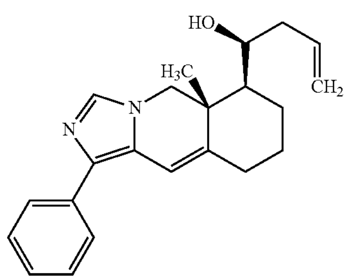 | 2.75 | 335.4 | 1 |
| 19 (±) | 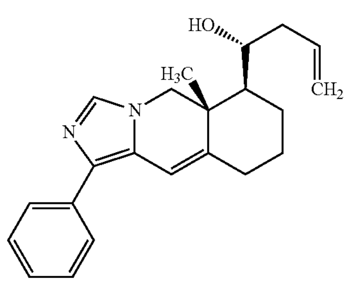 | 2.94 | 335.3 | 1 |
| 20 (±) | 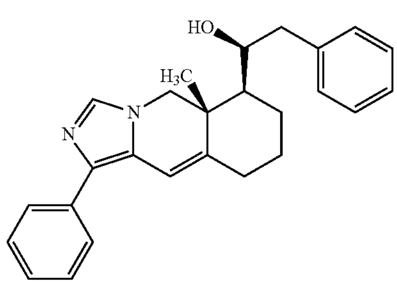 | 3.03 | 385.4 | 1 |

TABLE 1-continued

| Example No. | Structure | LC Retention Time (Min.)/Column* | LC-MS [M + H]+ | Procedure of Example |
|---|---|---|---|---|
| 21 (±) | 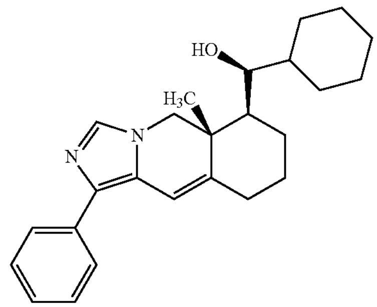 | 3.21 | 377.5 | 1 |
| 22 (±) | 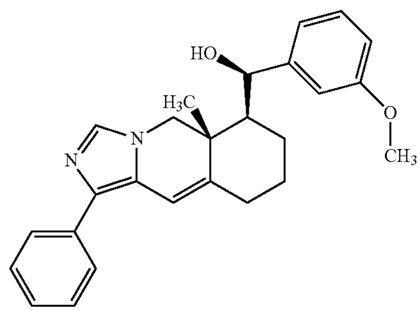 | 3.01 | 401.3 | 1 |
| 23 (±) | 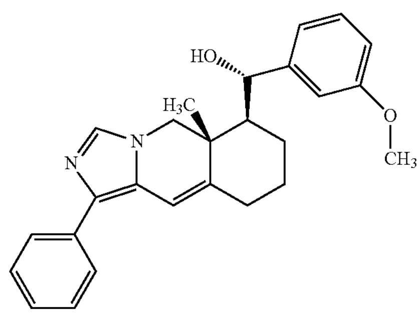 | 3.15 | 401.3 | 1 |
| 24 (±) | 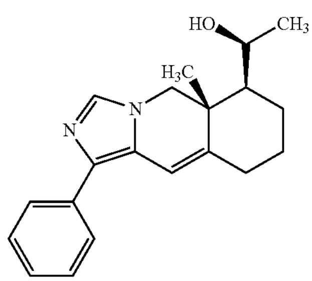 | 2.44 | 309.3 | 1 |
| 25 (±) | 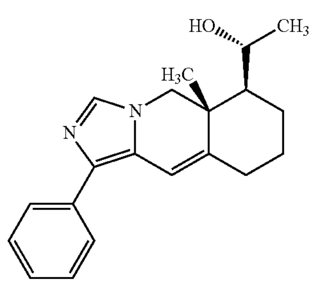 | 2.64 | 309.3 | 1 |

TABLE 1-continued

| Example No. | Structure | LC Retention Time (Min.)/Column* | LC-MS [M + H]+ | Procedure of Example |
|---|---|---|---|---|
| 26 | 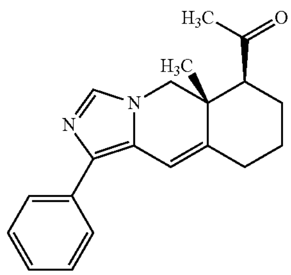 | 2.35 | 307.4 | 1 |
| 27 Enantiomer 1 | 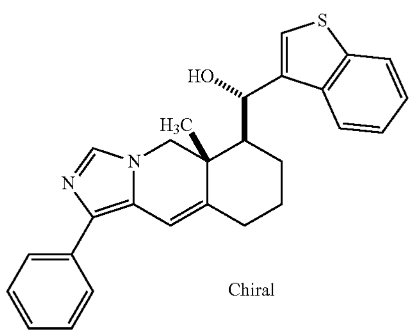 | 3.40 | 371.3 | 8 |
| 28 Enantiomer 2 | 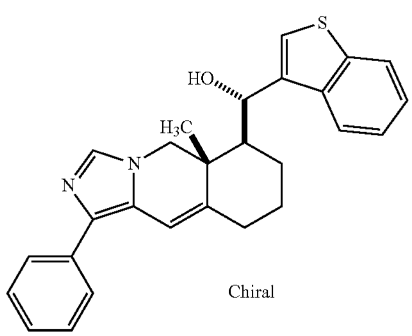 | 3.40 | 427.3 | 8 |
| 29 Enantiomer 1 | 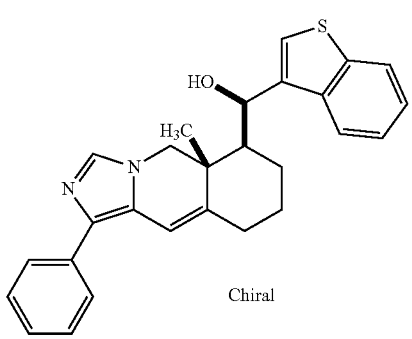 | 3.04 | 371.3 | 8 |

TABLE 1-continued

| Example No. | Structure | LC Retention Time (Min.)/Column* | LC-MS [M + H]+ | Procedure of Example |
|---|---|---|---|---|
| 30 Enantiomer 2 | 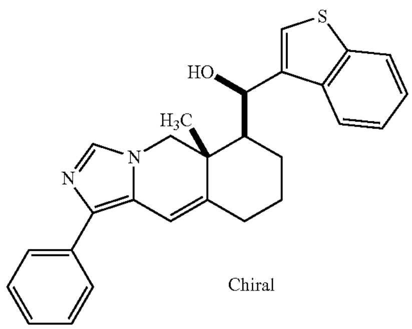 | 3.04 | 427.3 | 8 |
| 31 Enantiomer 1 | 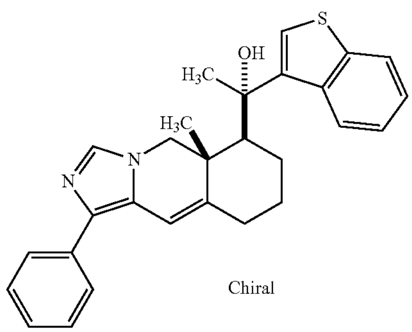 | 3.42 | 441.2 | 8 |
| 32 Enantiomer 2 | 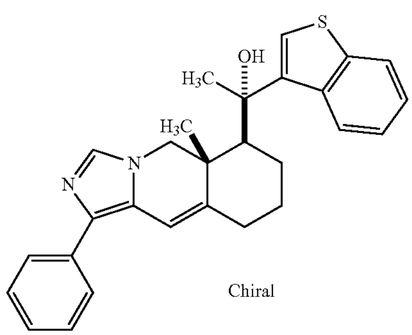 | 3.42 | 441.2 | 8 |
| 33 (±) | 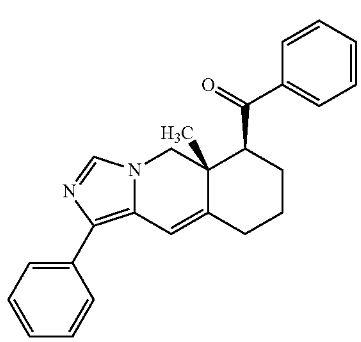 | 2.85 | 369.3 | 1 |

TABLE 1-continued

| Example No. | Structure | LC Retention Time (Min.)/Column* | LC-MS [M + H]⁺ | Procedure of Example |
|---|---|---|---|---|
| 34 (±) | 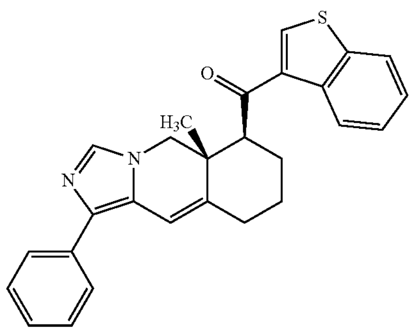 | 3.20 | 425.3 | 8 |
| 35 (±) | 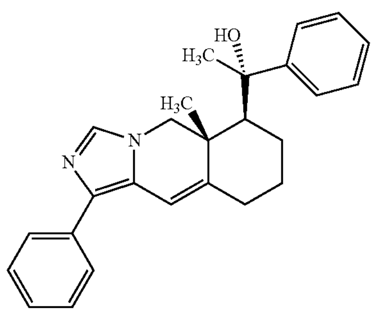 | 3.23 | 385.3 | 1 |
| 36 (±) | 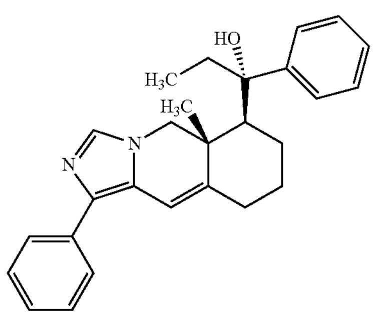 | 3.25 | 399.3 | 1 |
| 37 (±) | 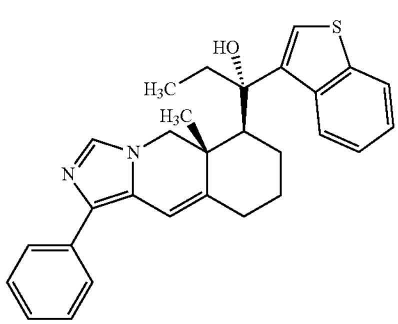 | 3.25 | 455.3 | 8 |

TABLE 1-continued

| Example No. | Structure | LC Retention Time (Min.)/Column* | LC-MS [M + H]⁺ | Procedure of Example |
|---|---|---|---|---|
| 38 (±) | 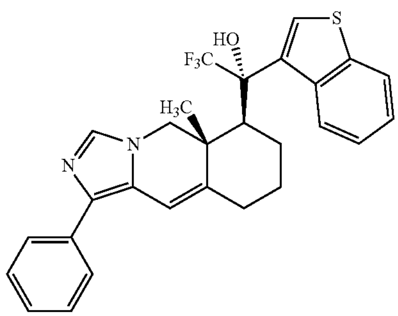 | 3.43 | 495.2 | 8 |
| 39 Enantiomer 1 | 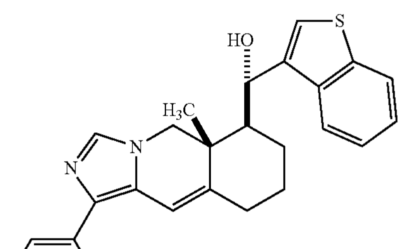 | 3.41 | 445.3 | 8 |
| 40 Enantiomer 2 | 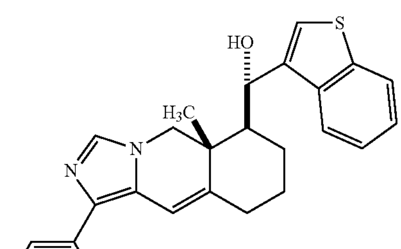 | 3.39 | 445.3 | 8 |
| 41 Enantiomer 1 | 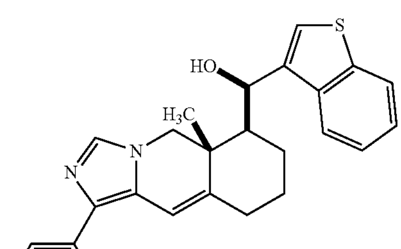 | 3.34 | 445.3 | 8 |

TABLE 1-continued
| Example No. | Structure | LC Retention Time (Min.)/Column* | LC-MS [M + H]+ | Procedure of Example |
|---|---|---|---|---|
| 42 Enantiomer 2 | 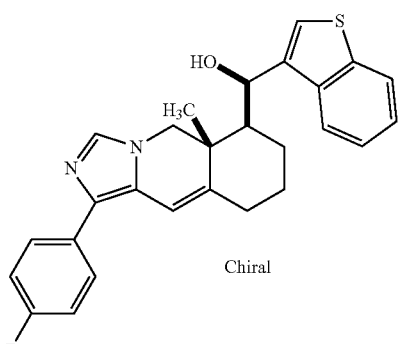 Chiral | 3.33 | 445.3 | 8 |
| 43 Enantiomer 1 | 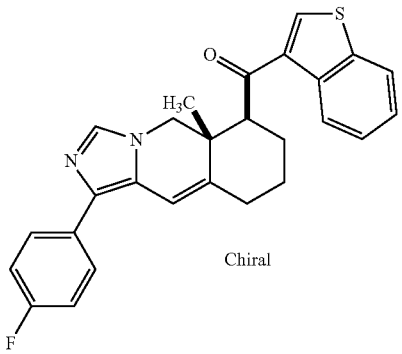 Chiral | 3.19 | 443.3 | 8 |
| 44 Enantiomer 2 | 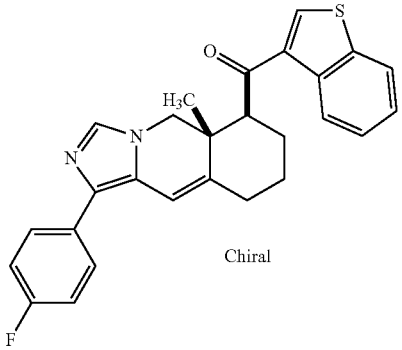 Chiral | 3.19 | 443.3 | 8 |
| 45 Enantiomer 1 | 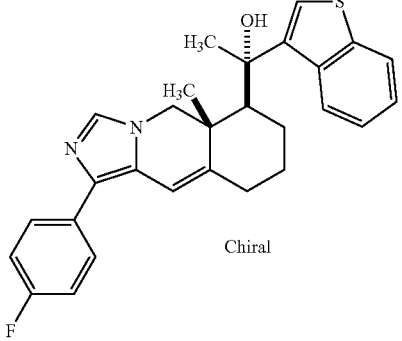 Chiral | 3.44 | 459.3 | 8 |

TABLE 1-continued
| Example No. | Structure | LC Retention Time (Min.)/Column* | LC-MS [M + H]+ | Procedure of Example |
|---|---|---|---|---|
| 46 Enantiomer 2 | 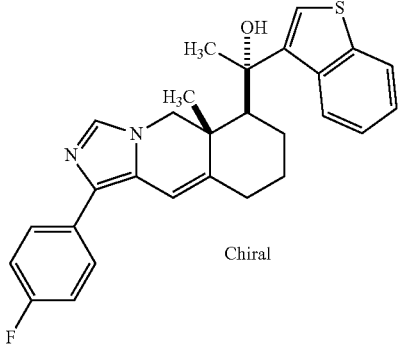 Chiral | 3.43 | 459.3 | 8 |
| 47 | 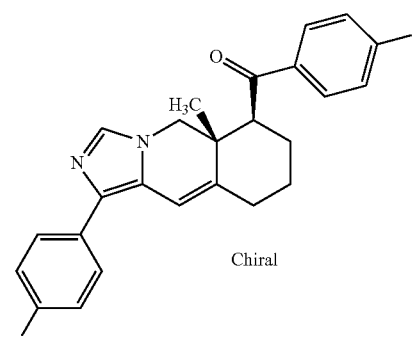 Chiral | 3.43 | 405.4 | 1 |
| 48 | 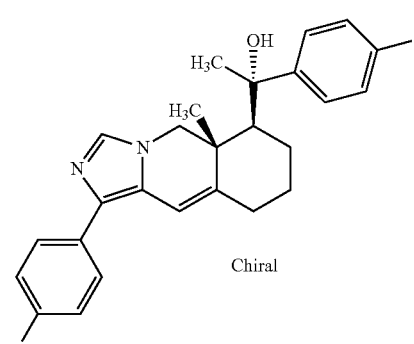 Chiral | 3.24 | 421.4 | 1 |
| 49 | 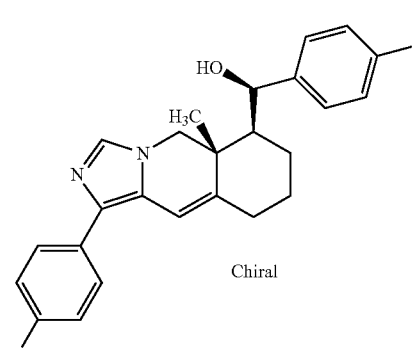 Chiral | 3.11 | 407.4 | 1 |

TABLE 1-continued
| Example No. | Structure | LC Retention Time (Min.)/Column* | LC-MS [M + H]+ | Procedure of Example |
|---|---|---|---|---|
| 50 | 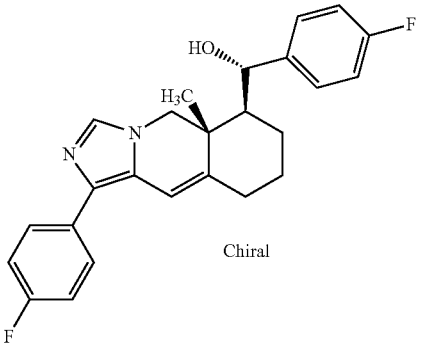 | 3.21 | 407.4 | 1 |
| 51 | 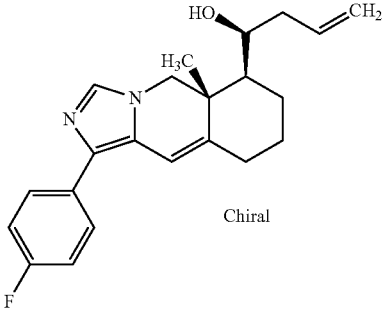 | 2.80 | 353.4 | 1 |
| 52 | 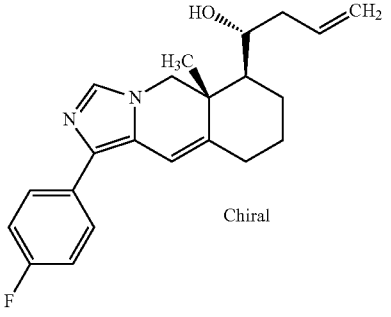 | 2.97 | 353.4 | 1 |
| 53 | 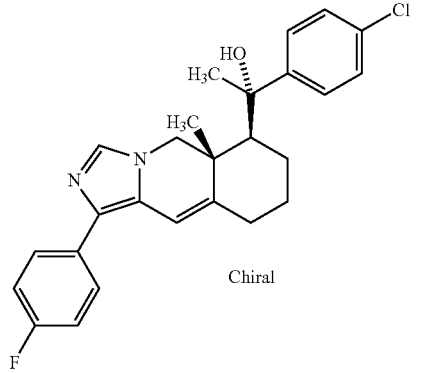 | 3.40 | 437.3 | 1 |

TABLE 1-continued
| Example No. | Structure | LC Retention Time (Min.)/Column* | LC-MS [M + H]⁺ | Procedure of Example |
|---|---|---|---|---|
| 54 | 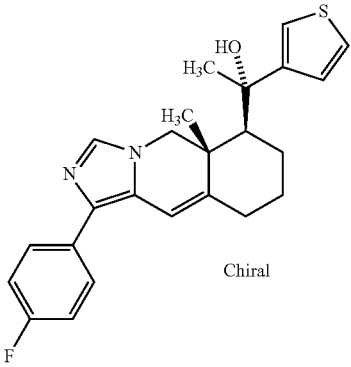<br>Chiral | 3.14 | 409.3 | 1 |
| 55 | 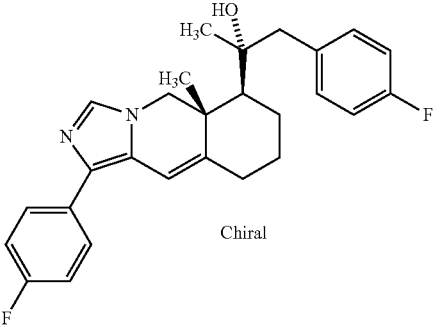<br>Chiral | 3.45 | 435.4 | 1 |
| 56 | 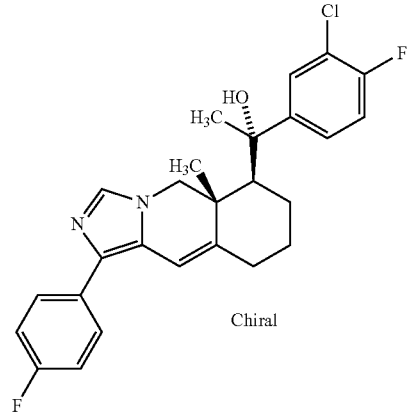<br>Chiral | 3.40 | 455.5 | 1 |
| 57 | 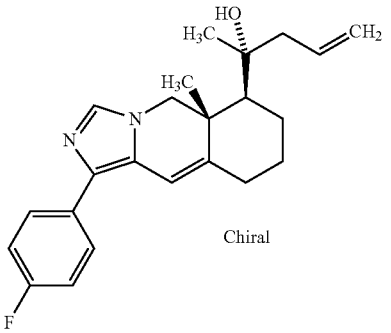<br>Chiral | 3.17 | 367.4 | 1 |

TABLE 1-continued
| Example No. | Structure | LC Retention Time (Min.)/Column* | LC-MS [M + H]+ | Procedure of Example |
|---|---|---|---|---|
| 58 | 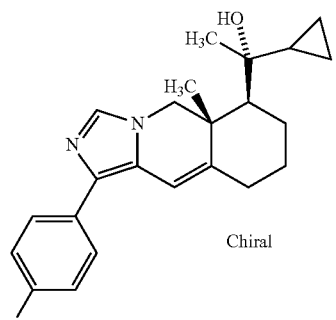 | 3.14 | 367.4 | 1 |
| 59 | 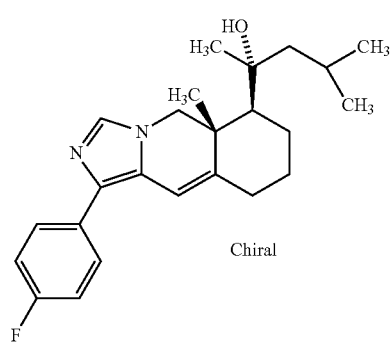 | 3.39 | 383.3 | 1 |
| 60 | 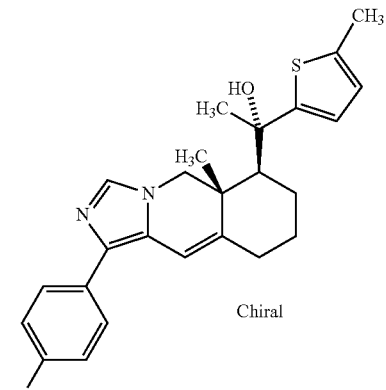 | 3.36 | 423.1 | 1 |
| 61 | 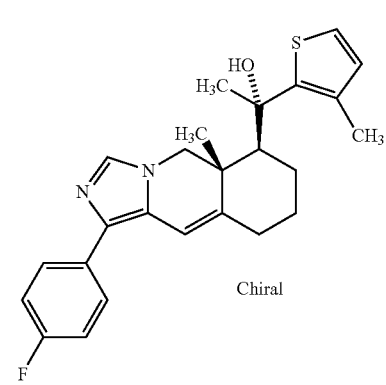 | 3.26 | 423.2 | 1 |

TABLE 1-continued
| Example No. | Structure | LC Retention Time (Min.)/Column* | LC-MS [M + H]+ | Procedure of Example |
|---|---|---|---|---|
| 62 | 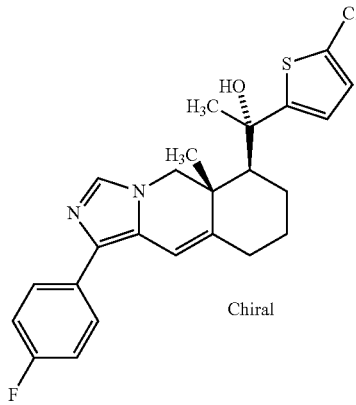 Chiral | 3.40 | 443.1 | 1 |
| 63 | 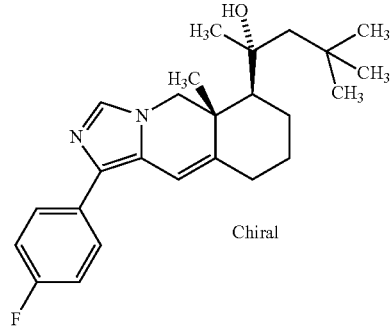 Chiral | 3.51 | 397.3 | 1 |
| 64 | 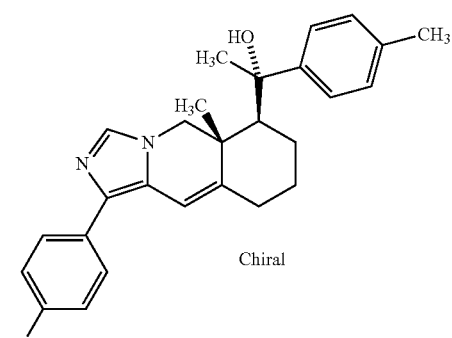 Chiral | 3.37 | 417.2 | 1 |
| 65 | 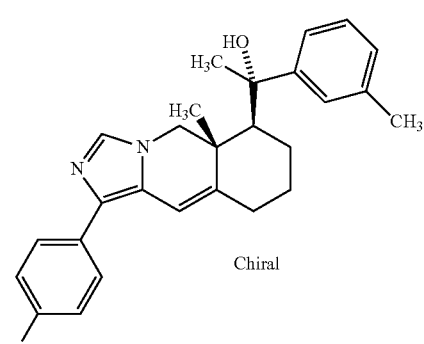 Chiral | 3.31 | 417.2 | 1 |

TABLE 1-continued
| Example No. | Structure | LC Retention Time (Min.)/Column* | LC-MS [M + H]+ | Procedure of Example |
|---|---|---|---|---|
| 66 | 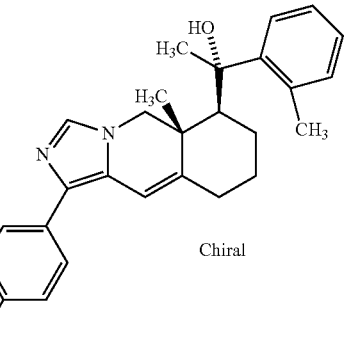 Chiral | 3.32 | 417.2 | 1 |
| 67 | 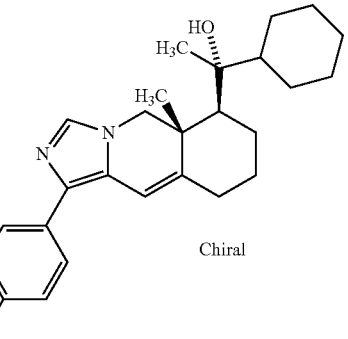 Chiral | 3.59 | 409.2 | 1 |
| 68 | 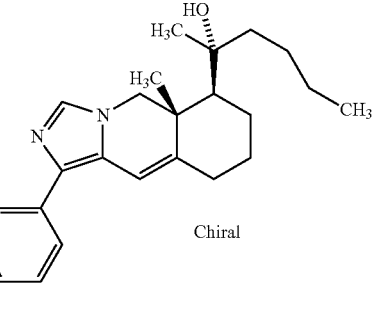 Chiral | 3.41 | 383.2 | 1 |
| 69 | 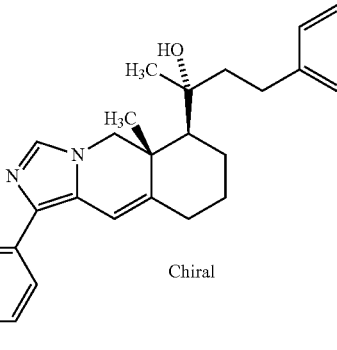 Chiral | 3.43 | 431.2 | 1 |

TABLE 1-continued
| Example No. | Structure | LC Retention Time (Min.)/Column* | LC-MS [M + H]+ | Procedure of Example |
|---|---|---|---|---|
| 70 | 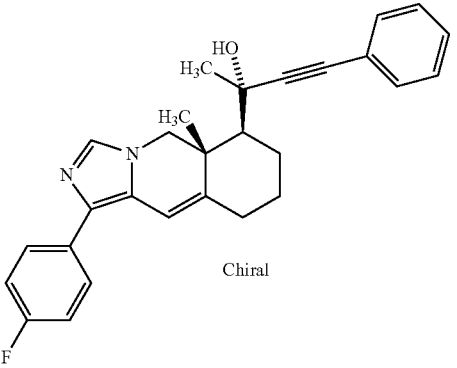 Chiral | 3.43 | 427.2 | 1 |
| 71 | 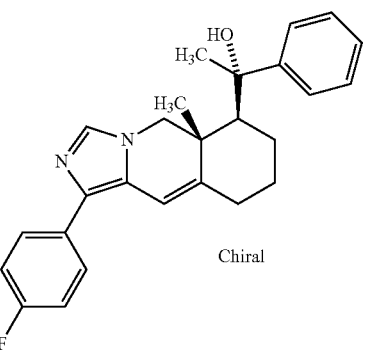 Chiral | 3.19 | 403.2 | 1 |
| 72 | 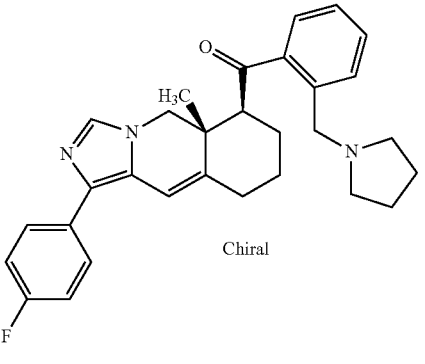 Chiral | 2.00 | 470.2 | 1 |
| 73 | 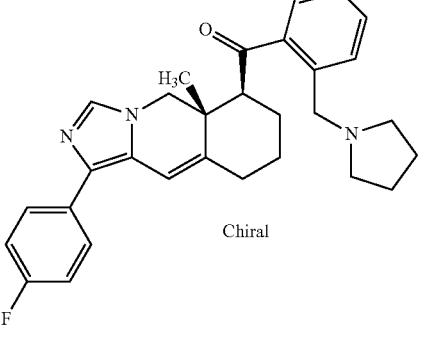 Chiral | 2.38 | 486.2 | 1 |

TABLE 1-continued
| Example No. | Structure | LC Retention Time (Min.)/Column* | LC-MS [M + H]⁺ | Procedure of Example |
|---|---|---|---|---|
| 74 | 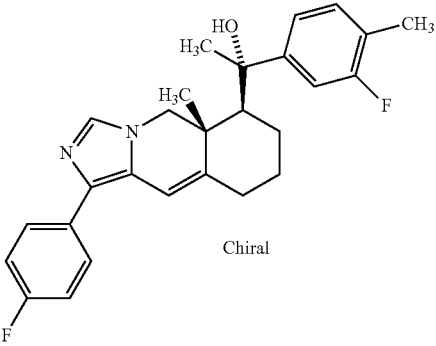 Chiral | 3.40 | 435.2 | 1 |
| 75 | 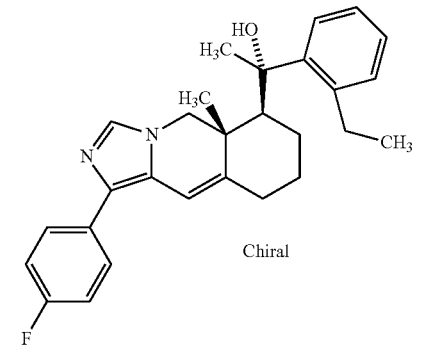 Chiral | 3.40 | 431.2 | 1 |
| 76 | 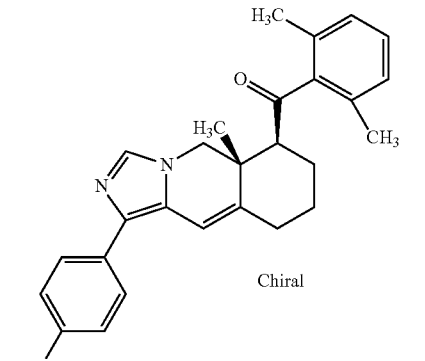 Chiral | 3.10 | 415.2 | 1 |
| 77 | 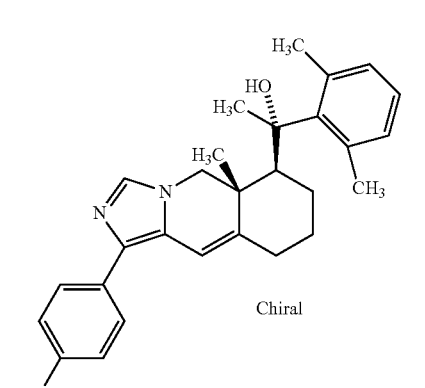 Chiral | 3.42 | 417.3 | 1 |

TABLE 1-continued
| Example No. | Structure | LC Retention Time (Min.)/Column* | LC-MS [M + H]+ | Procedure of Example |
|---|---|---|---|---|
| 78 | 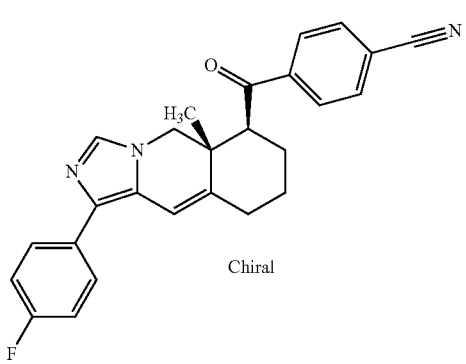 Chiral | 2.75 | 412.2 | 3 |
| 79 | 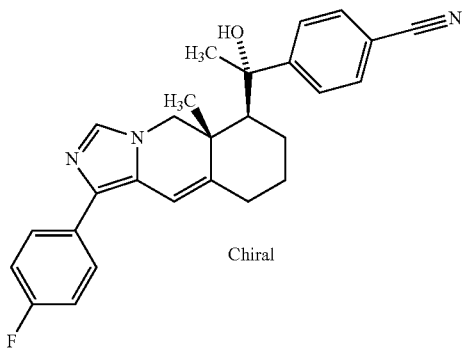 Chiral | 3.00 | 428.1 | 3 |
| 80 | 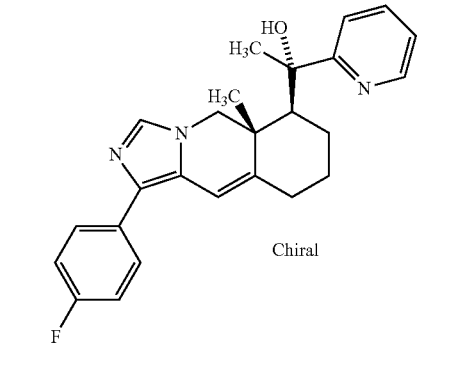 Chiral | 2.01 | 404.1 | 3 |
| 81 | 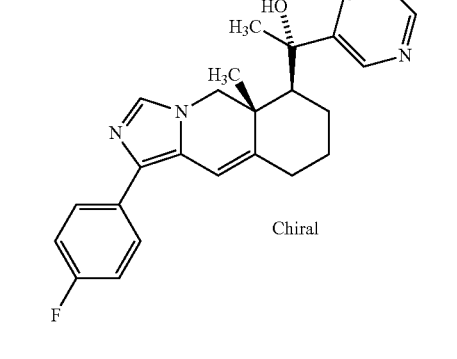 Chiral | 1.95 | 404.1 | 3 |

TABLE 1-continued
| Example No. | Structure | LC Retention Time (Min.)/Column* | LC-MS [M + H]+ | Procedure of Example |
|---|---|---|---|---|
| 82 | 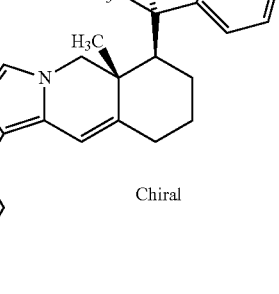 | 1.96 | 404.1 | 3 |
| 83 | 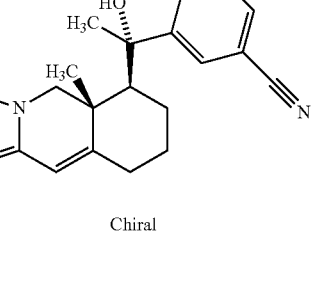 | 2.98 | 428.3 | 3 |
| 84 | 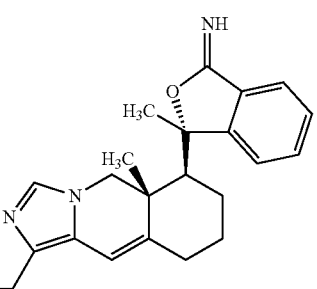 | 1.91 | 428.3 | 3 |
| 85 | 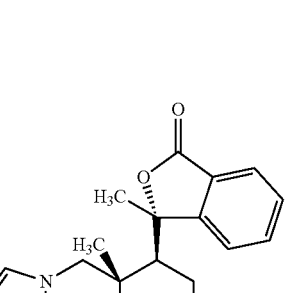 | 2.74 | 429.3 | 3 |

TABLE 1-continued
| Example No. | Structure | LC Retention Time (Min.)/Column* | LC-MS [M + H]+ | Procedure of Example |
|---|---|---|---|---|
| 86 | 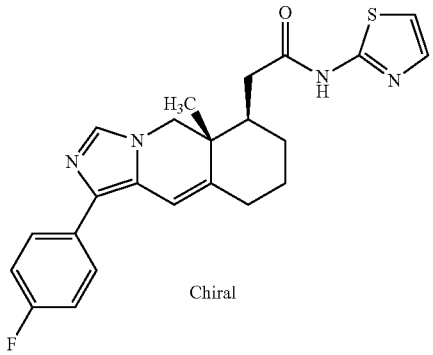<br>Chiral | 2.77 | 423.2 | 6 |
| 87 | 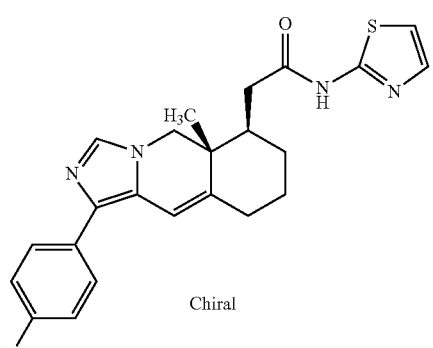<br>Chiral | 2.09 | 409.2 | 5 |
| 88 | 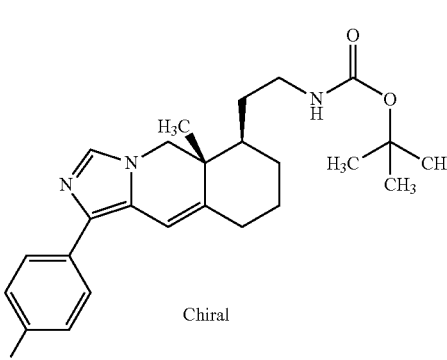<br>Chiral | 3.05 | 426.3 | 7 |
| 89 | 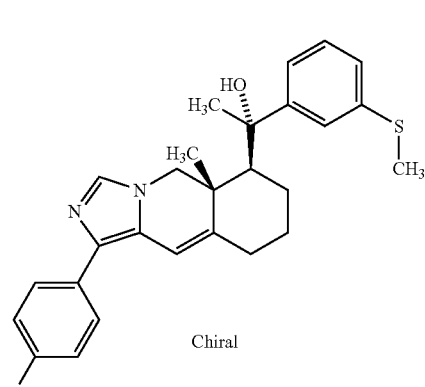<br>Chiral | 3.28 | 449.2 | 8 |

TABLE 1-continued
| Example No. | Structure | LC Retention Time (Min.)/Column* | LC-MS [M + H]+ | Procedure of Example |
|---|---|---|---|---|
| 90 | 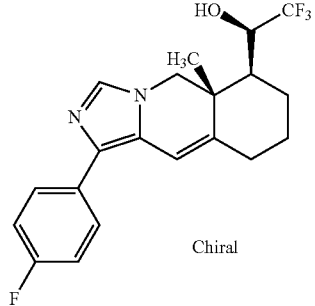 Chiral | 2.73 | 381.3 | 10 |
| 91 | 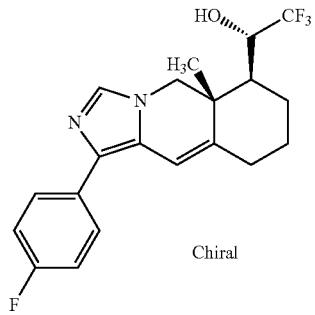 Chiral | 2.84 | 381.2 | 10 |
| 92 | 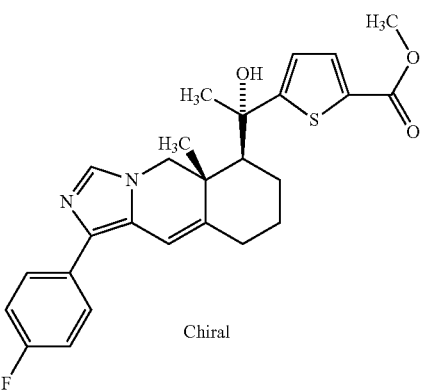 Chiral | 3.13 | 467.1 | 3 |
| 93 | 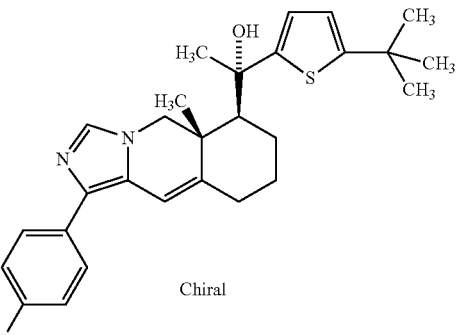 Chiral | 3.10 | 467.1 | 9 |

TABLE 1-continued
| Example No. | Structure | LC Retention Time (Min.)/Column* | LC-MS [M + H]+ | Procedure of Example |
|---|---|---|---|---|
| 94 | 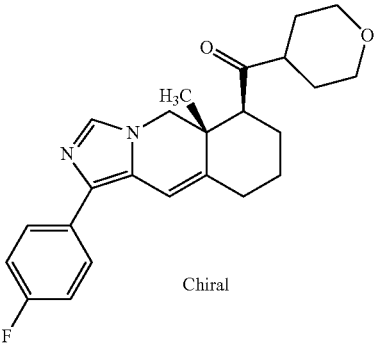 Chiral | 2.50 | 395.3 | 8 |
| 95 | 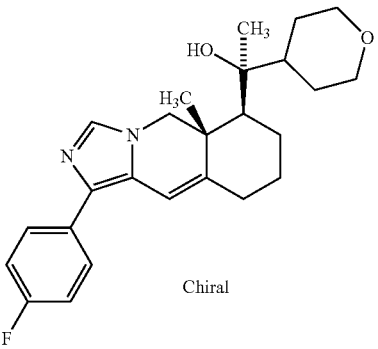 Chiral | 2.61 | 411.3 | 8 |
| 96 | 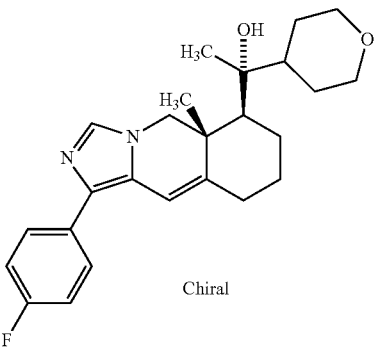 Chiral | 2.93 | 411.3 | 8 |
| 97 | 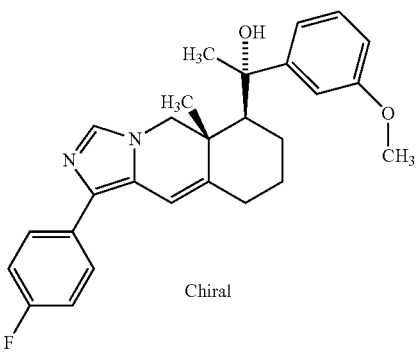 Chiral | 3.13 | 433.2 | 1 |

TABLE 1-continued
| Example No. | Structure | LC Retention Time (Min.)/Column* | LC-MS [M + H]+ | Procedure of Example |
|---|---|---|---|---|
| 98 | 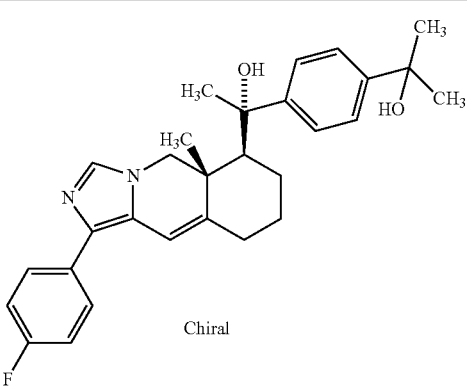 Chiral | 3.08 | 461.2 | 9 |
| 99 | 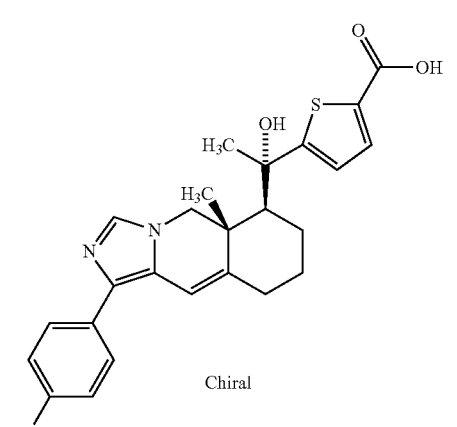 Chiral | 2.94 | 453.1 | 3 |
| 100 | 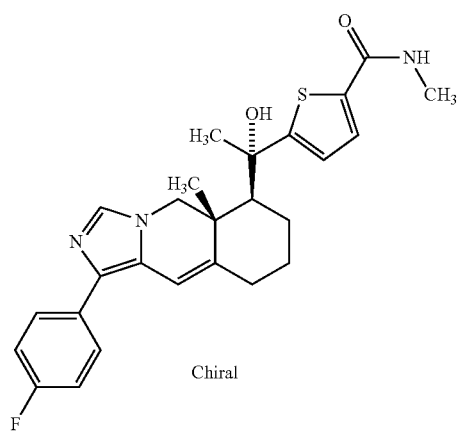 Chiral | 2.80 | 466.1 | 3 |
*HPLC conditions:
Column: YMC S5 CombiScreen ODS column 4.6 × 50 mm
Solvents: 10-90% aqueous methanol over 4 minutes containing 0.2% phosphoric acid.
Flow rate: 4 mL/min,
Detection: UV at 220 nm.

Example 101

1-(4-Fluorophenyl)-5a-methyl-6-vinyl-5,5a,6,7,8,9-hexahydroimidazo[1,5-b]isoquinolin-6-ol

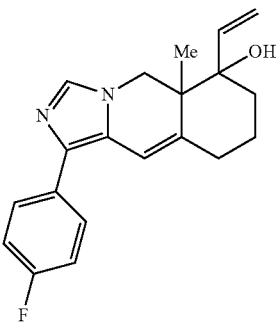

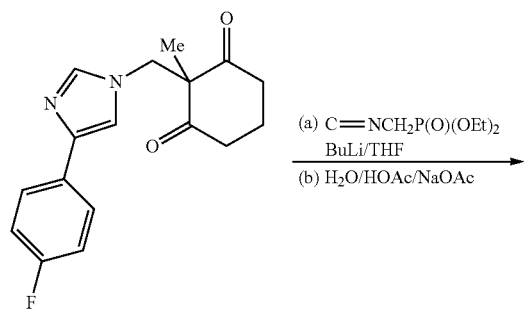

(a) C≡NCH₂P(O)(OEt)₂ BuLi/THF
(b) H₂O/HOAc/NaOAc

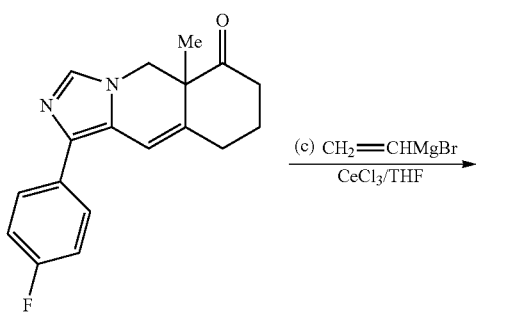

(c) CH₂═CHMgBr CeCl₃/THF

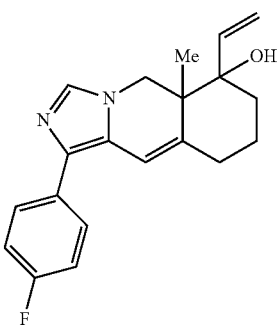

(a) To a stirred solution of diethyl isocyanomethylphosphonate (0.19 mL, 1.2 mmol) in anhydrous THF (4 mL) was added n-butyl lithium solution (2.5 M in hexanes, 0.48 mL, 1.2 mmol) dropwise at −50 to −60° C. under argon. The mixture was stirred at the same temperature for 30 min before a solution of 2-((4-(4-fluorophenyl)-1H-imidazol-1-yl)methyl)-2-methylcyclohexane-1,3-dione (Example 1, step d, 430 mg, 1.4 mmol) in anhydrous THF (30 mL) was added at −70° C. The mixture was stirred at the same temperature for 2 hr, at −20° C. for 2 hr, and at RT for 2 hr. The mixture was concentrated under reduced pressure, dissolved in ethyl acetate, filtered through a silica gel pad which was then rinsed with ethyl acetate. The filtrate was concentrated under reduced pressure to give a solid which was used as such for the subsequent step without further purification.

(b) The above solid was mixed with sodium acetate (0.48 g), acetic acid (2 mL), and water (2 mL) and heated at 170° C. in a CEM microwave reactor under nitrogen for 30 min. The reaction mixture was concentrated under reduced pressure to remove solvents. The residue was made basic using saturated aqueous sodium bicarbonate solution (15 mL), and extracted with ethyl acetate (4×3 mL). The combined organic solutions were dried (Na₂SO₄) and concentrated. Silica gel flash chromatography (10-100% ethyl acetate in hexanes) gave 1-(4-fluorophenyl)-5a-methyl-5,5a,8,9-tetrahydroimidazo[1,5-b]isoquinolin-6(7H)-one (92 mg, 0.23 mmol, 19% yield). MS found: (M+H)⁺=297.2.

(c) To anhydrous cerium(III) chloride (274 mg, 1.1 mmol) was added anhydrous THF (4 mL) under nitrogen. The mixture was stirred at RT for 30 min before vinylmagnesium bromide (1.1 mL, 1.1 mmol) was added dropwise at −78° C. under a nitrogen atmosphere. The reaction mixture was stirred at −78° C. for 30 min before a solution of 1-(4-fluorophenyl)-5a-methyl-5,5a,8,9-tetrahydroimidazo[1,5-b]isoquinolin-6(7H)-one (step a, 66 mg, 0.22 mmol) in anhydrous THF (2 mL) was added dropwise at the same temperature. The reaction mixture was stirred at −78° C. for 30 min and at RT for 1 hr. Concentrated aqueous ammonium hydroxide (1.5 mL) was added. The solid was filtered off through a celite pad and washed with ethyl acetate (3×2 mL). The organic filtrate was dried (Na₂SO₄), concentrated under reduced pressure, and dissolved in methanol (2 mL). Purification using reverse phase HPLC (YMC S5 20×100 mm, 10 min. run, solvent A: 10% MeOH: 90% H₂O: 0.1% TFA, solvent B: 90% MeOH, 10% H₂O, 0.1% TFA) gave 1-(4-fluorophenyl)-5a-methyl-6-vinyl-5,5a,6,7,8,9-hexahydroimidazo[1,5-b]isoquinolin-6-ol (40 mg, 0.12 mmol, 55% yield) as a glassy solid (after neutralization using saturated aqueous sodium bicarbonate solution and extraction with ethyl acetate). MS found: (M+H)⁺=325.2.

¹H NMR (400 MHz, chloroform-d) δ ppm 8.05 (br. s., 1H) 7.69-7.76 (m, 2H) 7.16 (t, J=8.56 Hz, 2H) 6.49 (d, J=1.76 Hz, 1H) 6.13 (dd, J=17.37, 10.83 Hz, 1H) 5.45 (d, J=17.12 Hz, 1H) 5.19 (d, J=11.08 Hz, 1H) 4.28 (d, J=13.60 Hz, 1H) 3.97 (d, J=13.35 Hz, 1H) 2.47-2.63 (m, 1H) 2.41 (dd, J=15.74, 4.66 Hz, 1H) 2.06-2.16 (m, 1H) 1.78-1.89 (m, 1H) 1.59-1.71 (m, 2H) 1.34 (s, 3H).

Examples 102 to 103

The following examples were prepared according to the general procedure described in Example 101.

TABLE 2

| Example No. | Structure | LC Retention Time (Min.)/Column* | LC-MS [M + H]+ | Procedure of Example |
|---|---|---|---|---|
| 102 (±) | 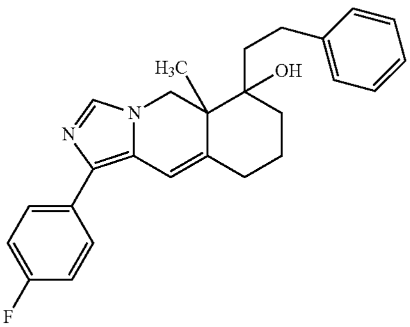 | 3.06 | 403.2 | 102 |
| 103 (±) | 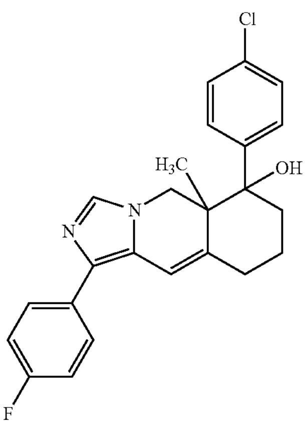 | 2.97 | 409.2 | 102 |

*HPLC conditions:
Column: YMC S5 CombiScreen ODS column 4.6 × 50 mm
Solvents: 10-90% aqueous methanol over 4 minutes containing 0.2% phosphoric acid,
Flow rate: 4 mL/min,
Detection: UV at 220 nm.

Example 104

1'-(4-Fluorophenyl)-5,5,5a'-trimethyl-5a',7',8',9'-tetrahydro-5'H-spiro[[1,3]dioxane-2,6'-imidazo[1,5-b]isoquinoline]

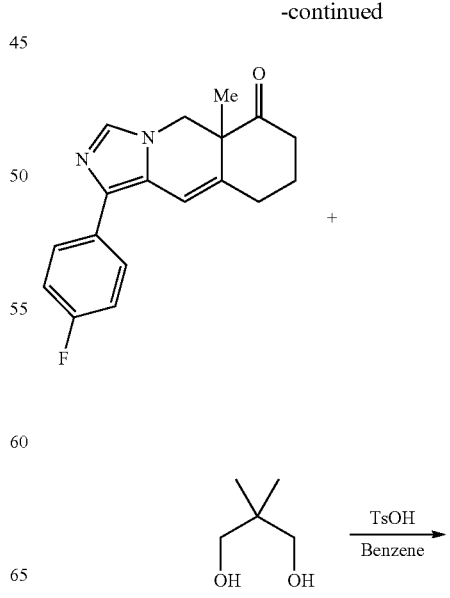

-continued

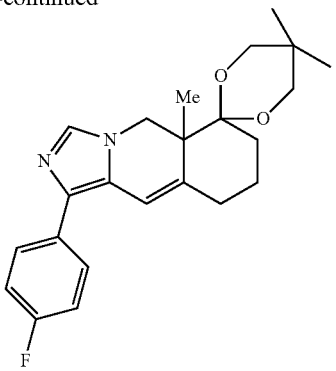

(a) A stirred mixture of 1-(4-fluorophenyl)-5a-methyl-5,5a,8,9-tetrahydroimidazo[1,5-b]isoquinolin-6(7H)-one (Example 101, step b, 11 mg, 0.037 mmol), 2,2-dimethylpropane-1,3-diol (12 mg, 0.11 mmol), p-toluenesulfonic acid monohydrate (9.6 mg, 0.056 mmol), and anhydrous benzene (15 mL) was heated using a azeoptrope setup over 2 hr. The mixture was then concentrated and dissolved in MeOH (2 mL). Purification using reverse phase HPLC (YMC S5 20×100 mm, 10 min. run, solvent A: 10% MeOH: 90% H$_2$O: 0.1% TFA, solvent B: 90% MeOH, 10% H$_2$O, 0.1% TFA) gave 1'-(4-fluorophenyl)-5,5,5a'-trimethyl-5a',7',8',9'-tetrahydro-5'H-spiro[[1,3]dioxane-2,6'-imidazo[1,5-b]isoquinoline] as a TFA salt (13 mg, 0.026 mmol, 71% yield).

MS found: (M+H)$^+$=383.3. $^1$H NMR (400 MHz, MeOD) δ ppm 8.92 (s, 1H) 7.60-7.66 (m, 2H) 7.30 (t, J=8.69 Hz, 2H) 6.47 (s, 1H) 4.91 (d, J=13 Hz, 1H) 4.38 (d, J=13.35 Hz, 1H) 3.89 (d, J=11.58 Hz, 1H) 3.76 (d, J=11.33 Hz, 1H) 3.41 (dd, 1H) 3.36 (dd, J=11.33, 2.52 Hz, 1H) 2.84-2.91 (m, 1H) 2.45-2.62 (m, 2H) 1.71-1.79 (m, 1H) 1.50-1.64 (m, 2H) 1.26 (s, 3H) 1.22 (s, 3H) 0.78 (s, 3H).

BIOLOGICAL ACTIVITY DATA

The AP-1 activity of Examples 1 to 104 is given where the AP-1 EC$_{50}$ is less than 1 uM. Accompanying AP-1 maximum inhibition values are also given. Where the AP-1 EC50 is greater than 1 uM and/or the maximal inhibition is less than 20%, the glucocorticoid receptor (GR) binding affinity (Ki) is given.

The data presented below were obtained using the assays referred to in the table and described herein in the ASSAY section supra.

| Example No. | GR (Ki, nM) (GR Binding Assay (I)$^a$) | AP-1 EC$_{50}$, nM (Cellular Trans-repression Assay) | AP-1 Max % inh (Cellular Trans-repression Assay) |
|---|---|---|---|
| 1 | | 21.43 | 38.08 |
| 2 | 69.82 | | |
| 3 | | 267.30 | 29.48 |
| 4a | 111.40 | | |
| 4b | 214.50 | | |
| 5 | | 97.97 | 22.59 |
| 6 | 7.13 | | |
| 7 | 95.71 | | |
| 8a | 2.12 | | |
| 8b | | 236.10 | 40.74 |
| 9 | | 144.40 | 34.30 |
| 10 | | 30.94 | 31.27 |
| 11 | 68.21 | | |
| 12 | 86.34 | | |
| 13 | >1154.00 | | |
| 14 | 65.00 | | |
| 15 | | 145.30 | 42.73 |
| 16 | 90.07 | | |
| 17 | 93.39 | | |
| 18 | 26.89 | | |
| 19 | 22.32 | | |
| 20 | 18.28 | | |
| 21 | 20.22 | | |
| 22 | 94.40 | | |
| 23 | 57.54 | | |
| 24 | 363.80 | | |
| 25 | 201.50 | | |
| 26 | >1154.00 | | |
| 27 | 9.09 | | |
| 28 | 492.80 | | |
| 29 | >1154.00 | | |
| 30 | 22.48 | | |
| 31 | | 181.10 | 41.16 |
| 32 | >1154.00 | | |
| 33 | >1154.00 | | |
| 34 | >1154.00 | | |
| 35 | 6.40 | | |
| 36 | 8.71 | | |
| 37 | 208.60 | | |
| 38 | 111.30 | | |
| 39 | 129.70 | | |
| 40 | 7.85 | | |
| 41 | >1154.00 | | |
| 42 | 36.07 | | |
| 43 | >1154.00 | | |
| 44 | >1154.00 | | |
| 45 | 73.25 | | |
| 46 | 1.43 | | |
| 47 | 878.20 | | |
| 48 | | 11.93 | 35.60 |
| 49 | 35.31 | | |
| 50 | 29.74 | | |
| 51 | 7.38 | | |
| 52 | 8.67 | | |
| 53 | | 63.23 | 44.64 |
| 54 | | 4.67 | 42.67 |
| 55 | | 84.19 | 53.72 |
| 56 | | 19.31 | 39.57 |
| 57 | | 56.60 | 55.86 |
| 58 | | 36.80 | 35.81 |
| 59 | 9.67 | | |
| 60 | | 31.33 | 48.34 |
| 61 | | 11.60 | 58.76 |
| 62 | | 5.48 | 61.21 |
| 63 | | 31.52 | 47.46 |
| 64 | | 4.26 | 41.86 |
| 65 | | 9.75 | 46.70 |
| 66 | | 4.60 | 42.10 |
| 67 | | 1.99 | 44.30 |
| 68 | | 33.87 | 40.78 |
| 69 | 47.16 | | |
| 70 | 59.85 | | |
| 71 | | 3.02 | 32.50 |
| 72 | >1154.00 | | |
| 73 | 87.08 | | |
| 74 | | 14.31 | 34.51 |
| 75 | | 41.64 | 47.06 |
| 76 | 207.10 | | |
| 77 | 8.41 | | |
| 78 | | | |
| 79 | 3.42 | | |
| 80 | 7.09 | | |
| 81 | 2.29 | | |
| 82 | 0.69 | | |
| 83 | | 19.20 | 35.61 |
| 84 | 201.30 | | |
| 85 | 177.20 | | |
| 86 | 67.10 | | |
| 87 | 38.34 | | |
| 88 | 11.37 | | |

-continued

| Example No. | GR (Ki, nM) (GR Binding Assay (I)$^a$) | AP-1 EC$_{50}$, nM (Cellular Trans-repression Assay) | AP-1 Max % inh (Cellular Trans-repression Assay) |
|---|---|---|---|
| 89 |  | 20.78 | 45.30 |
| 90 | 103.10 |  |  |
| 91 | 85.50 |  |  |
| 92 |  | 24.71 | 47.38 |
| 93 |  | 9.83 | 42.52 |
| 94 | 343.80 |  |  |
| 95 | 210.80 |  |  |
| 96 |  | 56.45 | 42.00 |
| 97 |  | 95.03 | 39.56 |
| 98 | 4.45 |  |  |
| 99 |  | 471.80 | 43.87 |
| 100 |  | 572.80 | 30.66 |
| 101 | 754.80 |  |  |
| 102 | 19.66 |  |  |
| 103 | 216.30 |  |  |
| 104 |  | 877.30 | 32.42 |

What is claimed is:

1. A compound of formula (I):

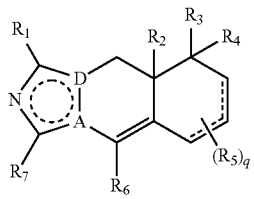

(I)

or enantiomers, diastereomers, or pharmaceutically-acceptable salts thereof, wherein:

- - - is a single bond or double bond;

one of A and D is —N— and the other of A and D is —C—;

$R_1$ is hydrogen, $C_{1-3}$alkyl, $C_{2-3}$alkenyl, $C_{2-3}$alkynyl, cyclopropyl, halogen, —CH$_2$F, CHF$_2$, —CF$_3$, —CN, $C_{1-3}$alkoxy, —NR$_d$R$_e$, —C(O)OR$_d$, or —C(O)NR$_d$R$_e$;

$R_2$ is hydrogen or $C_{1-3}$alkyl;

$R_3$ is hydrogen, OH, F, Cl, or $C_{1-3}$alkyl;

$R_4$ is i) hydrogen, ii) $C_{1-3}$alkyl optionally substituted with OH, F, or phenyl, iii) $C_{2-4}$alkenyl or $C_{2-4}$alkynyl, iv) aryl or aryl substituted with one or more of halogen, $C_{1-3}$alkyl, methoxy, and/or —CN, v) —CR$_a$R$_b$R$_c$, —C(O)R$_c$, —(CH$_2$)$_p$C(O)NHR$_c$, —(CH$_2$)$_p$NHR$_c$, —(CH$_2$)$_p$NHC(O)OR$_c$, or —(CH$_2$)$_p$NHC(O)NHR$_c$, wherein p is zero, 1, 2, or 3, vi) —CR$_a$R$_b$R$_c$ wherein R$_b$ and R$_c$ together with the carbon atom to which they are attached form a 1- or 2-ring heterocycle having at least one heteroatom selected from N, O, and S, or $R_3$ and $R_4$ together with the carbon atom to which they are attached, form a 5- to 7-membered saturated heterocyclic ring having 1 to 2 heteroatoms independently selected from N, O, and S, or vii)

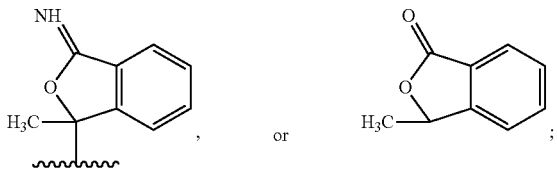

each $R_5$ is independently $C_{1-4}$alkyl, $C_{1-4}$haloalkyl, $C_{3-6}$cycloalkyl, $C_{2-4}$alkenyl, $C_{2-4}$alkynyl, F, Cl, —CN, $C_{1-3}$alkoxy, and/or —OCF$_3$;

$R_6$ is hydrogen, $C_{1-4}$alkyl, $C_{1-4}$haloalkyl, $C_{3-6}$cycloalkyl, $C_{2-4}$alkenyl, $C_{2-4}$alkynyl, F, Cl, —CN, $C_{1-3}$alkoxy, or —OCF$_3$;

$R_7$ is aryl or heterocyclo optionally substituted with one or more of $C_{1-3}$alkyl, $C_{1-3}$haloalkyl, $C_{1-3}$alkoxy, CN, and/or halogen;

$R_a$ is hydrogen, $C_{1-3}$alkyl, or $C_{1-3}$alkyl substituted with OH or F;

$R_b$ is hydrogen, OH, $C_{1-3}$alkyl, $C_{1-3}$alkoxy, or $C_{1-3}$alkyl substituted with OH or F;

$R_c$ is:

i) $C_{1-5}$alkyl optionally substituted with OH, aryl, or haloaryl, ii) $C_{1-3}$haloalkyl, $C_{3-6}$cycloalkyl, or $C_{2-4}$alkenyl, iii) $C_{2-4}$alkynyl optionally substituted with aryl, iv) aryl optionally substituted with one or more of halogen, methoxy, —S(O)(C$_{1-3}$alkyl), —S(O)$_2$(C$_{1-3}$alkyl), —CN, $C_{1-3}$alkyl, $C_{1-3}$hydroxyalkyl, $C_{1-3}$haloalkyl, saturated heterocyclo, and/or —S—(C$_{1-3}$alkyl), v) 1- or 2-ring aryl or heteroaryl optionally substituted with one or more of $C_{1-4}$-alkyl, halogen, —C(O)OH, —C(O)O(C$_{1-3}$alkyl), —C(O)NH(C$_{1-3}$alkyl), or —C(O)N(C$_{1-3}$alkyl)$_2$, or vi) tetrahydropyranyl;

$R_d$ is hydrogen or $C_{1-3}$alkyl;

$R_e$ is hydrogen or $C_{1-3}$alkyl; and q is zero, 1, 2, or 3.

2. A compound according to claim 1 of formula (Ia) or (Ib):

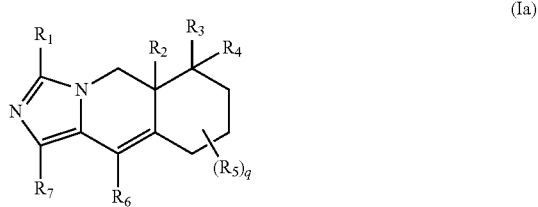

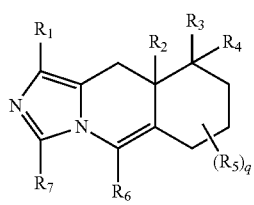

or enantiomers, diastereomers, or pharmaceutically-acceptable salts thereof.

3. A compound according to claim 2 of formula (Ic):

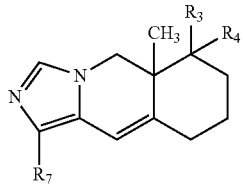

(Ic)

or enantiomers, diastereomers, or pharmaceutically-acceptable salts thereof, wherein:

$R_3$ is hydrogen or OH;

$R_4$ is
  i) hydrogen,
  ii) $C_{1-3}$alkyl optionally substituted with OH or phenyl,
  iii) $C_{2-4}$alkenyl,
  iv) phenyl optionally substituted with Cl,
  v) —$CR_aR_bR_c$, —$C(O)R_c$, —$(CH_2)_pC(O)NHR_c$, —$(CH_2)_pNHR_c$, —$(CH_2)_pNHC(O)OR_c$, or —$(CH_2)_pNHC(O)NHR_c$, wherein p is zero, 1, 2, or 3, or
  vi)

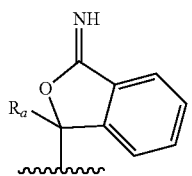

or ;

$R_a$ is hydrogen, methyl, ethyl, or —$CF_3$;

$R_b$ is hydrogen, OH, or methoxy; and $R_c$ is:
  i) $C_{1-5}$alkyl optionally substituted with phenyl or fluorophenyl,
  ii) $C_{1-3}$-fluoroalkyl, $C_{3-6}$cycloalkyl, or $C_{2-4}$alkenyl,
  iii) $C_{2-4}$alkynyl optionally substituted with phenyl,
  iv) phenyl optionally substituted with one or more of F, Cl, methoxy, —$S(O)CH_3$, —$S(O)_2CH_3$, —CN, $C_{1-3}$alkyl, —$SCH_3$, and/or $C_{1-3}$alkyl substituted with OH or pyrrolidinyl,
  v) tetrahydropyranyl, pyridinyl, pyrimidinyl, thiazolyl, thiadiazolyl, or thianaphthenyl, or
  vi) thiophenyl optionally substituted with $C_{1-4}$alkyl, Cl, —C(O)OH, —$C(O)OCH_3$, —$C(O)NHCH_3$, or —$C(O)N(CH_3)_2$; or $R_3$ and $R_4$ together with the carbon atom to which they are attached, form a 5- to 7-membered saturated heterocyclic ring having 1 to 2 heteroatoms independently selected from N, O, and S; and $R_7$ is unsubstituted aryl or aryl substituted with halogen.

4. A compound according to claim 3, or enantiomers, diastereomers, or pharmaceutically-acceptable salts thereof, wherein:

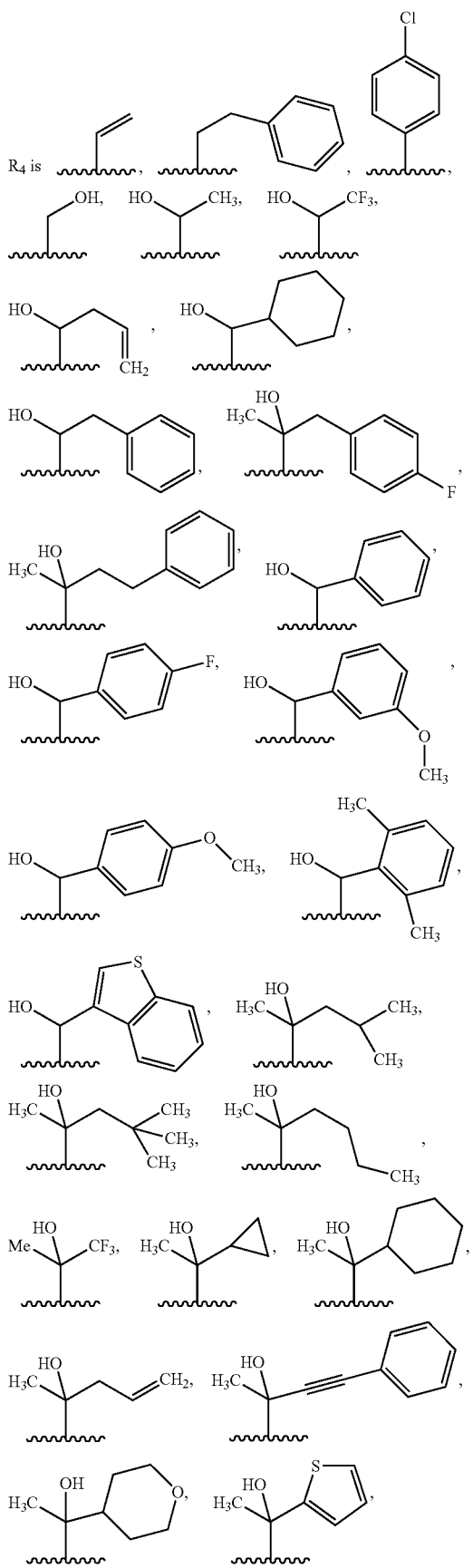

127
-continued
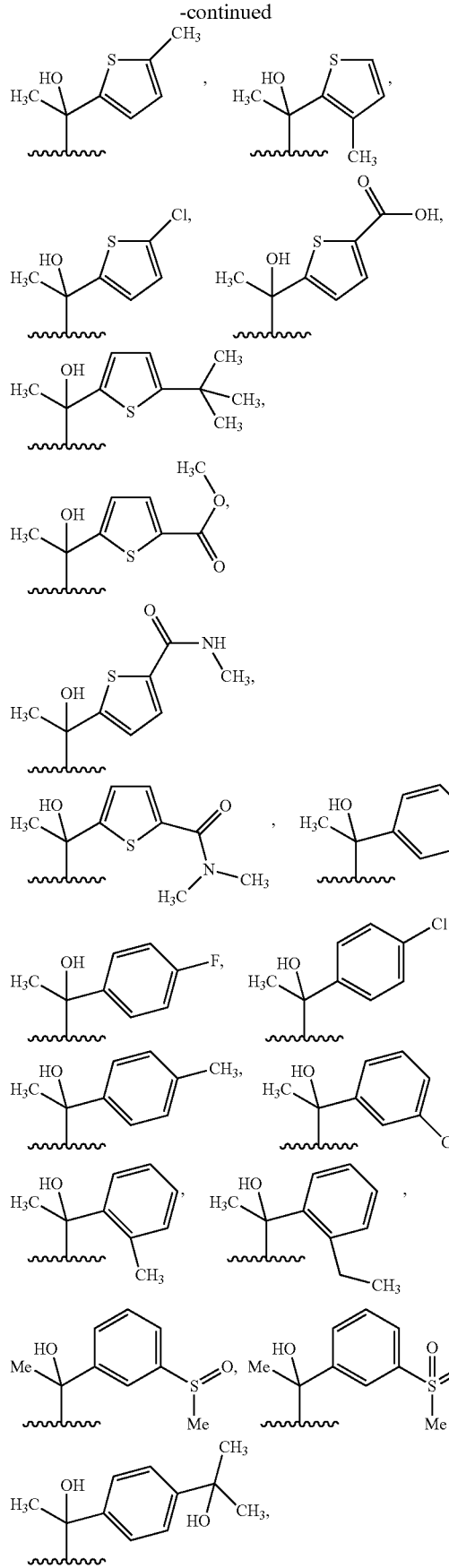
128
-continued
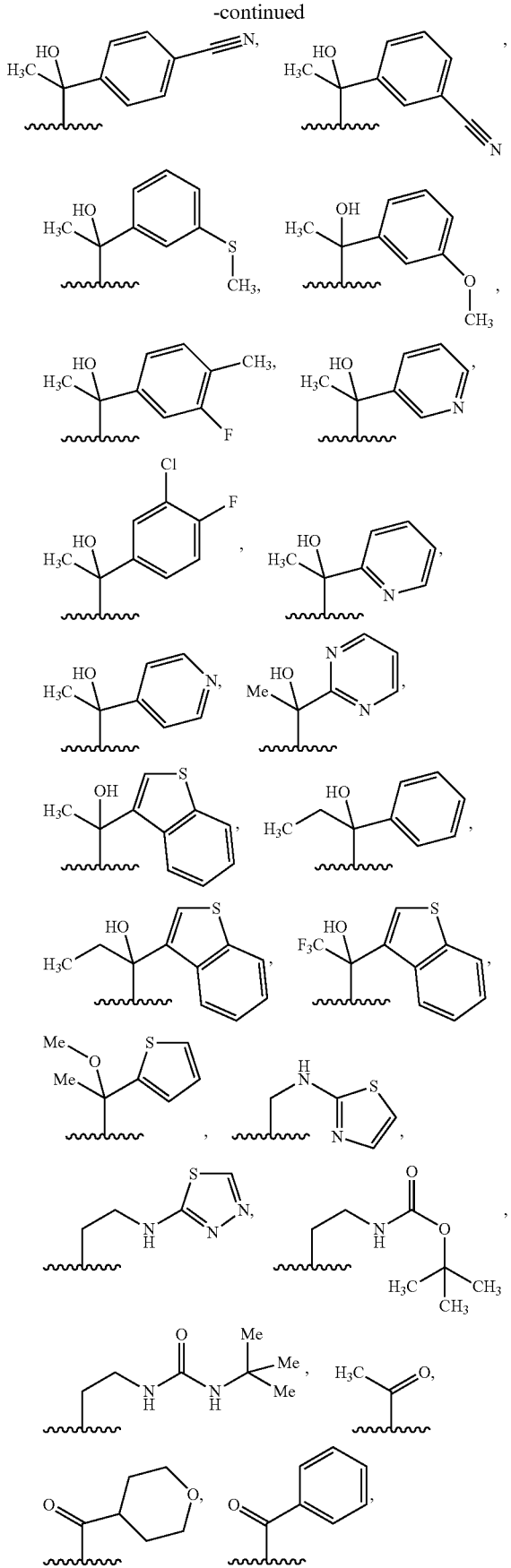

-continued

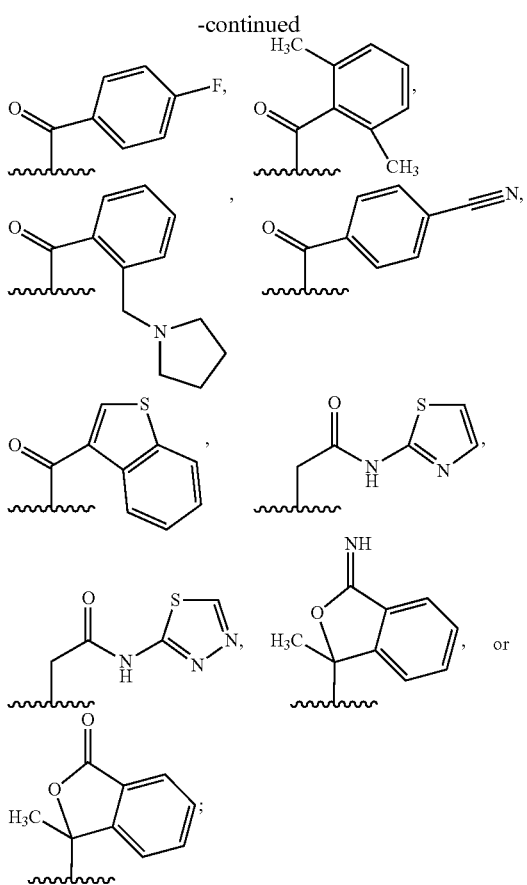

or $R_3$ and $R_4$ together are:

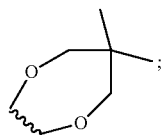

and $R_7$ is phenyl or fluorophenyl.

5. A pharmaceutical composition comprising a compound according to claim 1, or an enantiomer, diastereomer, or pharmaceutically-acceptable salt thereof; and a pharmaceutically-acceptable carrier.

6. A pharmaceutical composition according to claim 5 further comprising an immunosuppressant, an anticancer agent, an anti-viral agent, an anti-inflammatory agent, an anti-fungal agent, an anti-biotic, an anti-vascular hyperproliferation agent, an anti-depressant agent, a lipid-lowering agent, a lipid modulating agent, an antidiabetic agent, an anti-obesity agent, an antihypertensive agent, a platelet aggregation inhibitor, and/or an antiosteoporosis agent, wherein the antidiabetic agent is 1, 2, 3 or more of a biguanide, a sulfonyl urea, a glucosidase inhibitor, a PPAR γ agonist, a PPAR α/γ dual agonist, an SGLT2 inhibitor, a DP4 inhibitor, an aP2 inhibitor, an insulin sensitizer, a glucagon-like peptide-1 (GLP-1), insulin and/or a meglitinide, wherein the anti-obesity agent is a beta 3 adrenergic agonist, a lipase inhibitor, a serotonin (and dopamine) reuptake inhibitor, a thyroid receptor agonist, an aP2 inhibitor and/or an anorectic agent, wherein the lipid lowering agent is an MTP inhibitor, an HMG CoA reductase inhibitor, a squalene synthetase inhibitor, a fibric acid derivative, an upregulator of LDL receptor activity, a lipoxygenase inhibitor, or an ACAT inhibitor, wherein the antihypertensive agent is an ACE inhibitor, angiotensin II receptor antagonist, NEP/ACE inhibitor, calcium channel blocker and/or β-adrenergic blocker.

7. A method for reducing, ameliorating or partially or completely alleviating symptoms of a disease or disorder comprising administering to a patient afflicted with such disease, a therapeutically effective amount of a compound according to claim 1, or an enantiomer, diastereomer, or pharmaceutically-acceptable salt thereof; wherein said disease or disorder is selected from a metabolic disease and an inflammatory or immune disease which is selected from asthma, inflammatory bowel disease, multiple sclerosis, psoriasis, psoriatic arthritis, rheumatoid arthritis, systemic lupus erythematosis, transplant rejection, Type I diabetes, Type II diabetes, juvenile diabetes, and obesity.

* * * * *

UNITED STATES PATENT AND TRADEMARK OFFICE
CERTIFICATE OF CORRECTION

| | | |
|---|---|---|
| PATENT NO. | : 8,309,730 B2 | |
| APPLICATION NO. | : 12/741597 | |
| DATED | : November 13, 2012 | |
| INVENTOR(S) | : T. G. Murali Dhar et al. | |

It is certified that error appears in the above-identified patent and that said Letters Patent is hereby corrected as shown below:

On the Title Page:

Item (54), line 4, and in the Specifications, Column 1, line 4, change "ACITIVITY" to -- ACTIVITY --.

In the Claims:

Claim 1:

Column 123, line 67, after "or", insert

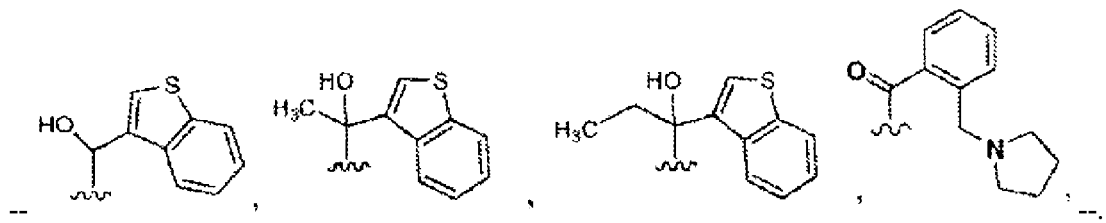

Column 124, line 37, change "$C_{1-4}$-alkyl," to -- $C_{1-4}$alkyl, --.

Column 124, line 43, change "$R_c$" to -- $R_e$ --.

Claim 3:

Column 125, line 46, change "$C_{1-3}$-fluoroalkyl," to -- $C_{1-3}$fluoroalkyl, --.

Signed and Sealed this
Twenty-eighth Day of May, 2013

Teresa Stanek Rea
*Acting Director of the United States Patent and Trademark Office*